(12) United States Patent
Kizhakkedathu et al.

(10) Patent No.: US 8,637,008 B2
(45) Date of Patent: *Jan. 28, 2014

(54) POLYMERS FOR REVERSING HEPARIN-BASED ANTICOAGULATION

(75) Inventors: Jayachandran N. Kizhakkedathu, New Westminster (CA); Rajesh A. Shenoi, Vancouver (CA); Cedric J. Carter, Vancouver (CA); Donald E. Brooks, Vancouver (CA)

(73) Assignee: University of British Columbia, Vancouver, B.C (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/458,899

(22) Filed: Apr. 27, 2012

(65) Prior Publication Data
US 2012/0308546 A1 Dec. 6, 2012

Related U.S. Application Data

(63) Continuation of application No. 13/504,841, filed as application No. PCT/CA2011/050603 on Sep. 27, 2011.

(60) Provisional application No. 61/492,299, filed on Jun. 1, 2011.

(51) Int. Cl.
*A61K 38/45* (2006.01)
*C12N 5/078* (2010.01)
*B01D 15/04* (2006.01)

(52) U.S. Cl.
USPC ............................... 424/94.5; 435/2; 210/679

(58) Field of Classification Search
None
See application file for complete search history.

(56) References Cited

U.S. PATENT DOCUMENTS

| | | | |
|---|---|---|---|
| 4,800,016 A | 1/1989 | Yang | |
| 5,614,494 A * | 3/1997 | Wakefield et al. | 514/13.7 |
| 2006/0204472 A1 | 9/2006 | Paleos et al. | |
| 2008/0064810 A1 | 3/2008 | Sellergren et al. | |

FOREIGN PATENT DOCUMENTS

| | | |
|---|---|---|
| CA | 2271132 | 5/1998 |
| CA | 2272944 | 6/1998 |
| CA | 2285151 | 4/2000 |
| CA | 2539301 | 3/2005 |
| WO | WO 96/35954 | 11/1996 |
| WO | WO 2005/028422 | 3/2005 |

OTHER PUBLICATIONS

Cushing et al., Reversal of Heparin-induced increases in aPTT in the rat by PM102, a novel heparin antagonist, Eur. J. Pharmacol. 2010, vol. 635, p. 165-170.*
Kizhakkedathu et al., Blood compatibility of novel water soluble hyperbranched polyglycerol-based multivalent cationic polymers and their interaction with DNA, Biomaterials, 2006, vol. 27, p. 5377-5390.*
Feng et al., Host-Guest Chemistry of Dendrimer-Drug Complexes 5. Insight into the design of formulations for noninvasive delivery of heparin revealed by isothermal titration calorimetry and NMR studies, J. Phy. Chem. B, 2010, vol. 114, p. 11017-11026.*
Jain et al., Pharmaceutical and biomedical potential of PEGylated dendrimers, Current Pharmaceutical design, 2007, 13, p. 415-429.*
Cajio et al, In silico design of polymeric antidote for anticoagulant fondaparinux, J. Medical Biological Engineering, 2011, vol. 31, pp. 129-134, Published Apr. 2011.*
U.S. Appl. No. 13/504,841, filed Apr. 27, 2012, Kizhakkedathu et al.
File History of U.S. Appl. No. 13/504,841, filed Apr. 27, 2012.
Preliminary Amendment filed on Apr. 27, 2012, in U.S. Appl. No. 13/504,841.
Breillat et al., (1984) Hemocompatibility Studies—Quantification of Serum Complement Activation by Polymeric Membranes and Materials, ASAIO J 7(2), 57-63.
Cajiao, A, et al (2010) In Silico Design of Polymeric Antidote for Anticoagulant Fondaparinux. Journal of Medical and Biological Engineering, 31(2), 129-134.
Chang, L-C, et al. (2001) Low molecular weight protamine (LMWP) as nontoxic heparin/low molecular weight heparin antidote (II): In vitro evaluation of efficacy and toxicity. AAPS Pharmsci 3(2) article 18.
Chang, L-C, et al. (2005) PEG-modified protamine with pharmacological/pharmaceutical properties as a potential protamine substitute: Synthesis and in vitro evaluation. Bioconj Chem 16, 147-155.
Crampton, H, et al (2007) Dendrimers as drug delivery vehicles: non-covalent interactions of bioactive compounds with dendrimers. Polym Int.56(4): 489-496.
Fabian, I, Aronson, M. (1980) Polycations as possible substitutes for protamine in heparin neutralization. Thrombosis Res 17, 239-247.
Fischer, W, et al. (2010) Dendridic polyglycerols with oligoamine shells show low toxicity and high siRNA transfection efficiency in vitro. Bioconj Chem 21, 1744-1752.
Horrow, J.C. (1985) Protamine: A Review of its Toxicity, Anesth Analg. 64:348-61.
International Search Report of International Patent Application No. PCT/CA2011/050603, mailed on Feb. 20, 2012, filed on Sep. 27, 2011.
Jantova et al. (1991) Biomedical Polymers Differ in Their Capacity to Activate Complement, Complement and Inflammation 8:61.
Kainthan et al. (2006) Biocompatibility Testing of Branched and Linear Polyglycidol, Biomacromolecules 7(3):703-709.
Kainthan et al. (2007) In vivo biological evaluation of high molecular weight hyperbranched polyglycerols, Biomaterials 28(32): 4779-4787.

(Continued)

*Primary Examiner* — Daniel Sullivan
*Assistant Examiner* — Ping Cao
(74) *Attorney, Agent, or Firm* — Knobbe, Martens, Olson & Bear LLP

(57) ABSTRACT

Embodiments presented herein relate to various polymers. Some of the polymer embodiments are heparin binding polymers. Some embodiments of the heparin binding polymers can be employed to bind to heparin for methods such as separating, purifying, removing, and/or isolating heparin and heparin like molecules.

20 Claims, 50 Drawing Sheets

(56) References Cited

OTHER PUBLICATIONS

Kidane et al. (1999) Complement Activation by PEO-Grafted Glass Surfaces, J Biomed Mate Res 48:640.

Kimmel et al. (1998) Adverse Events after Protamine Administration in Patients Undergoing Cardiopulmonary Bypass: Risks and Predictors of Under-Reporting, J Clin Epidemiol. 51:1-10.

Kizhakkedathu et al. (2005) Water-Soluble Nanoparticles from Random Copolymer and Oppositely Charged Surfactant, $3^a$, Nanoparticles of Poly(ethylene glycol)-Based Cationic Random Copolymer and Fatty Acid Salts, Macromol Biosci. 5(6):549:558.

Lamba et al. (1999) In vitro investigation of the blood response to medical grade PVC and the effect of heparin on the blood response, Biomaterials 21:89-96.

Lim et al. (1993) Effects of oligoethylene oxide monoalkyl(aryl) alcohol ether grafting on the surface properties and blood compatibility of a polyurethane, Biomaterials 14(7):537-545.

Makris et al. (2000) 'Blood Doping' with Recombinant Erythropoietin (rhEPO) and Assessment of Functional Iron Deficiency in Healthy Volunteers, Br J. Haematol. 108:883-888.

Mecca, T, et al. (2006) Polycationic calix[8]arenes able to recognize and neutralize heparin. Org Biomol Chem 4, 3763-3768.

Nair et al. (2007) Biodegradable polymers as biomaterials, Prog Polymer Sci. 32(8-9):762-798.

Nisha et al. (2004) Complexes of Poly(ethylene glycol)-Based Cationic Random Copolymer and Calf Thymus DNA: A Complete Biophysical Characterization, Langmuir 20(6):2386-2396.

Nisha et al. (2004) Water-Soluble Complexes from Random Copolymer and Oppositely Charged Surfactant, 2. Complexes of Poly(ethylene glycol)-Based Cationic Random Copolymer and Bile Salts, Langmuir 20(20):8468-8475.

Payne et al. (1987) Complement activation by hydroxyethylmethacrylate-ethylmethacrylate coplymers, J Biomed Mater Res 21:843.

Shastri et al. (1997) Complement Activation by Heparin-Protamine Complexes During Cardiopulmonary Bypass: Effect of C4A Null Allele, Cardiovasc Surg. 114(3):482-8.

Turk et al., (2004) Dendritic Polyglycerol Sulfates as New Heparin Analogues and Potent Inhibitors of the Complement System, Bioconjugate Chem., vol. 15, pp. 162-167.

Written Opinion of International Patent Application No. PCT/CA2011/050603, mailed on Feb. 20, 2012, filed on Sep. 27, 2011.

Restriction Requirement received in U.S. Appl. No. 13/504,841, dated Dec. 5, 2012.

Response to Restriction Requirement filed on Dec. 10, 2012 in U.S. Appl. No. 13/504,841.

Feng et al., "Host-Guest Chemistry of Dendrimer-Drug Complexes. 5. Insights into the Design of Formulations for Noninvasive Delivery of Heparin Revealed by Isothermal Titration Calorimetry and NMR Studies," J. Phys. Chem. B, 2010, pp. 11017-11026, vol. 114.

Brooks et al., "Hydrophovically derivatized hyperbranched polyglycerol as a human serum albumin substitute," Biomaterials, 2008, vol. 29, p. 1693-1704.

Frey et al., "Controlled synthesis of hyperbranched polyglycerols by ring-opening multibranching polymerization," Macromolecules, 1999, 32, 4240-4246.

Frey et al., "Hyperbranched polyglycerols: from the controlled synthesis of biocompatible polyether polyols to multipurpose applications," Accounts of Chemical Research, 2010, vol. 43, p. 129-141.

Haag et al., "Dendrtic Polyglycerols for Biomedical Applications," Adv Mater, 2010, vol. 22, p. 190-218.

Huck et al., Hyerbranched polyglycidol on Si/SiO2 surfaces via surface initiated polymerization, Macromolecules, 2003, 36, 5088-5093.

Vannucchi et al., "Complexing of Heparin with phosphatidylcholine," Biochem. J., 1985, vol. 227, p. 64.

Notice of Allowance dated Jun. 4, 2013, received in U.S. Appl. No. 13/504,841.

\* cited by examiner

General structure of Unfractionated Heparin (UFH) and Low Molecular Weight heparins (LMWHs)

Fondaparinux

Idraparinux

| FIG.2B-1 | FIG.2B-2 | FIG.2B-3 |
|---|---|---|
| | FIG.2B-4 | |

*FIG.13A*
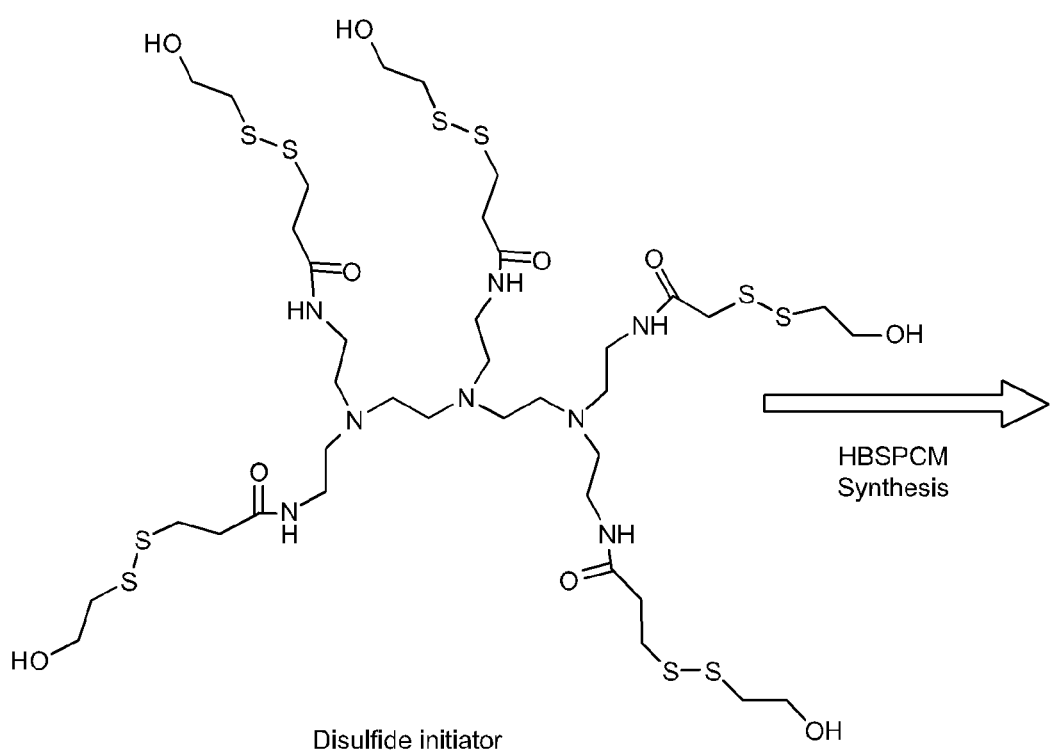
Disulfide initiator
HBSPCM Synthesis
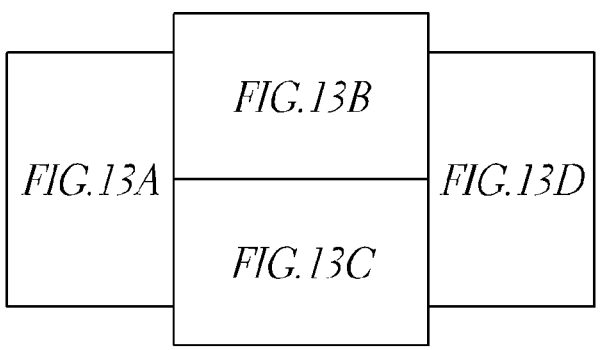
*FIG. 13*

US 8,637,008 B2

POLYMERS FOR REVERSING HEPARIN-BASED ANTICOAGULATION

REFERENCE TO RELATED APPLICATIONS

This application is a continuation of U.S. application Ser. No. 13/504,841, filed Apr. 27, 2012, which was the U.S. National Phase entry under 35 U.S.C. §371 of International Application PCT/CA2011/050603, filed Sep. 27, 2011, entitled "POLYMERS FOR REVERSING HEPARIN-BASED ANTICOAGULATION," which claims priority to U.S. Provisional Application Ser. No. 61/492,299, filed Jun. 1, 2011, the entireties of which are incorporated herein by reference.

TECHNICAL FIELD

The present embodiments relates to novel polymers that bind to heparin, heparin derivatives and heparinoids and methods for making such polymers.

BACKGROUND

Heparin is an anionic compound involved in a variety of biological processes including blood coagulation. Heparin derivatives used in current clinical anticoagulation therapy include unfractionated heparin (UFH), low molecular weight heparin (LMWH), ultra low molecular weight heparin (UL-MWH) and the synthetic pentasccharide derivatives fondaparunix and idraparinux.

Heparinoids can be naturally occurring and synthetic highly-sulfated polysaccharides of similar structure to heparin. Heparinoid preparations have been used for a wide range of applications including as anticoagulant and anti-inflammatories and they have been claimed to have hypolipidemic properties.

Heparin neutralization, which can be desired when a subject is given too much heparin, can be achieved, for example, via protamine or through filtration of the blood through an extracorporeal device.

SUMMARY

Some embodiments provided herein relate to heparin binding polymers. In some embodiments, the polymer has a first dendritic polyol and one or more cationic moieties attached to the first dendritic polyol.

In some embodiments, a heparin binding device is provided. The device can have a support and a heparin binding polymer immobilized on the support. The heparin binding polymer can have a first dendritic polyol and one or more cationic moieties attached to the first dendritic polyol.

In some embodiments, a method of making a heparin binding polymer is provided. The method can include combining a glycidol and a PEG-epoxide, methylating the glycidol and the PEG-epoxide to form a hyperbranched polyglycerol, tosylating the hyperbranched polyglycerol to form a tosylated hyperbranched polyglycerol, and coupling the tosylated hyperbranched polyglycerol with at least one amine group, thereby making a heparin binding polymer.

In some embodiments, a method of counteracting heparin in a subject is provided. The method can include administering a heparin binding polymer to a subject. The heparin binding polymer can include a first dendritic polyol and one or more cationic moieties attached to the first dendritic polyol. The heparin binding polymer binds to heparin and thereby counteracts heparin in the subject.

In some embodiments, a method of processing a subject's blood is provided. The method can include providing a heparin binding device. The device can include a support and a heparin binding polymer immobilized on the support. The heparin binding polymer can include a first dendritic polyol and one or more cationic moieties attached to the first dendritic polyol. The method can further include withdrawing blood from a subject, contacting the blood to the heparin binding polymer, and returning at least part of the blood to the subject, thereby processing the subject's blood.

In some embodiments, a method of concentrating heparin is provided. The method can include providing a support and a heparin binding polymer immobilized on the support. The heparin binding polymer can include a first dendritic polyol and one or more cationic moieties attached to the first dendritic polyol. The method can further include contacting a first fluid including heparin with the heparin binding polymer and flowing the fluid off of the heparin binding polymer. This can thereby concentrate heparin.

In some embodiments, a heparin binding composition is provided. The composition can include a first heparin binding polymer having a first dendritic polyol and one or more cationic moieties attached to the first dendritic polyol. The composition can further include a pharmaceutically acceptable carrier.

In some embodiments, a heparin binding macromolecule is provided. The macromolecule can include a hyperbranched polyglycidol core, at least one polyvalent cation attached to the hyperbranched polyglycidol core, and at least one protective moiety attached to the hyperbranched polyglcidol core.

In some embodiments, a heparin composition is provided. The composition can include heparin and a heparin binding polymer. The heparin binding polymer can include a first dendritic polyol and one or more cationic moieties attached to the first dendritic polyol.

In some embodiments, a kit is provided. The kit can include a first container including heparin and a second container including a heparin binding polymer. The heparin binding polymer can include a first dendritic polyol and one or more cationic moieties attached to the first dendritic polyol.

In some embodiments, the heparin binding polymer can be used for binding and drug delivery of anionic drug molecules such as heparins, synthetic pentasaccharide anticoagulants, low and ultra low molecular weight heparins or methatrexate or similar compounds. The foregoing summary is illustrative only and is not intended to be in any way limiting. In addition to the illustrative aspects, embodiments, and features described above, further aspects, embodiments, and features will become apparent by reference to the drawings and the following detailed description.

In some embodiments, a controlled release delivery device is provided. The device can include a surface and a heparin binding polymer attached to the surface. The heparin binding polymer can include a first dendritic polyol and one or more cationic moieties attached to the first dendritic polyol. The controlled release delivery device can also include heparin. In some embodiments, the heparin is bound to the heparin binding polymer.

In some embodiments, a controlled release heparin composition is provided. The composition can include a heparin binding polymer. The heparin binding polymer can include a first dendritic polyol and one or more cationic moieties attached to the first dendritic polyol. The controlled release heparin composition can also include heparin. In some embodiments, the heparin is bound to the heparin binding polymer.

DETAILED DESCRIPTION

Figure 1A:
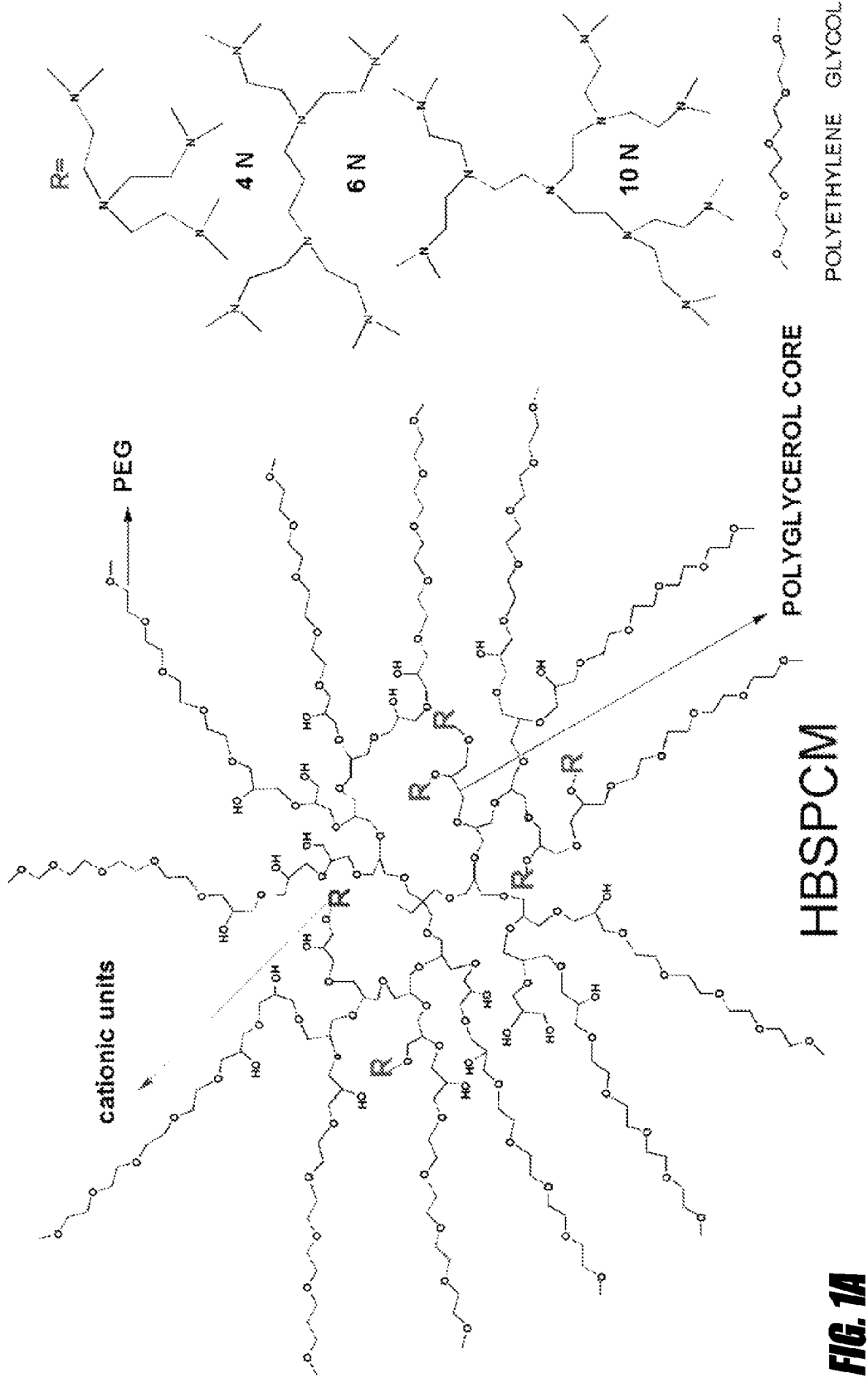
FIG. 1A depicts a schematic representation of some embodiments of a heparin binding synthetic polyvalent cationic macromolecule with different amine groups (R=tetra-amine (4 nitrogens), hexa-amine (6 nitrogens) and deca-amine (10 nitrogens).

A complication and health concern associated with the use of heparin and its derivatives for anticoagulation therapy is bleeding. Antidotes are needed to reverse the effects of heparin or its derivatives to avoid bleeding complications while maintaining sufficient levels of the anticoagulant to prevent thrombosis. Apart from bleeding complications, neutralization of anticoagulant drugs following major surgical procedures can be useful to prevent postoperative complications.

The only antidote available for UFH approved by the U.S. Food and Drug Administration (FDA) is protamine. There are numerous disadvantages to using protamine as a heparin antidote, including its narrow window for therapeutic dosage, poorer outcomes for blood transfusions and the lack of a reliable method for the quantification of protamine in blood. Protamine is associated with a number of anaphylactic adverse drug reactions (Horrow et al. 1985 Anesth Analg: 64:348-61; Kimmel et al. 1998 J Clin Epidemiol. 51:1-10).

Biospecific polybases, including polypeptides, synthetic peptides and cationic polymers, can bind and neutralize heparin and heparin derivatives to overcome the disadvantages of protamine and other antidotes. As disclosed herein, the efficiency of neutralization of heparin and heparin derivatives depends on the net charge, charge density and molecular structure of polybases.

Provided herein are various molecules and compositions that can be used for binding to heparin. It has been discovered that a class of biocompatible hyperbranched polyol polymers have the ability to bind to heparin and heparin derivatives and, in some embodiments, to act as an antidote to heparin-based anticoagulation therapy. In some embodiments, the molecules are hyperbranched polyether polyol polymers. It is understood by the present inventors that this new use is distinct from other uses of hyperbranched polyether polyols, including their use as carriers, drug delivery vehicles or modulating an energy substrate. In some embodiments, the molecules include a dendritic polyol attached to one or more cationic moieties. As described in greater detail below, in some embodiments, such molecules can be employed to purify and/or isolate heparin, among other uses.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure provides a general set of definitions (which can include various embodiments) of terms that are relevant to some of the embodiments. The disclosure then provides a detailed set of embodiments and examples. While various sections of the disclosure include headings, these headings are not to be interpreted in a limiting manner, and are present merely for the sake of convenience.

DEFINITIONS AND EMBODIMENTS

Any terms not directly defined herein shall be understood to have all the meanings commonly associated with them as understood within the art. Certain terms are discussed below, or elsewhere in the specification, to provide additional guidance to the practitioner in describing the devices, methods and the like of various embodiments, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments herein.

As used herein, a "HPG polymer" refers to a hyperbranched polyether polyol, including hyperbranched polyglycerol (HPG) and heparin-binding synthetic polyvalent cationic macromolecules (HBSPCMs). Various methods for synthesizing and modifying HPG polymers are described herein, and in the literature. Initiating species can include polyols and polyamine. In some embodiments, HPG polymers can be further derivatized with alkyl groups, polyethylene glycol groups, amine groups, sulfate groups, carbohydrates, peptides, amino acids and the like.

As used herein, a "HBSPCM polymer" or "HBSPCM" refers to a heparin-binding synthetic polyvalent cationic macromolecule. Various methods for synthesizing and modifying HBSPCM polymers are described herein. In some embodiments, the core of the HBSPCM polymer can include a HPG polymer. The core of the HBSPCM can be capped with short chain polyethylene glycols (PEGS) to create a macromolecule.

The term "heparin binding polymer" is generic to both "HPG polymer" and "HBSPCM polymer".

"Subject", as used herein, refers to an entity to receive the molecule, compound, treatment, etc. In some embodiments, the subject is a human patient, human test subject, a primate, or other mammal, such as a rat, mouse, dog, cat, cow, pig, sheep, monkey or the like.

As used herein, a "pharmaceutically acceptable excipient" includes any and all solvents, dispersion media, coatings, antibacterial, antimicrobial or antifungal agents, isotonic and absorption delaying agents, and the like that are physiologically compatible. The excipient may be suitable for intravenous or intraarterial administration. The excipient can include sterile aqueous solutions or dispersions for extemporaneous preparation of sterile injectable solutions or dispersion. Examples of sterile aqueous solutions include saline, Ringer's lactate or other solutions as may be known in the art. Use of such media in the preparation of a medicament is known in the art.

As used herein, a "pharmacologically effective amount" of a medicament refers to using an amount of a medicament present in such a concentration to result in a therapeutic level of drug delivered over the term that the drug is used. This can be dependent on mode of delivery, time period of the dosage, age, weight, general health, sex and diet of the subject receiving the medicament.

In some embodiments, HPG polymers can be administered to a subject to neutralize the effect of heparin or heparin derivatives on the subject. As used herein, the term "neutralize" includes, in its various grammatical forms (e.g., "neutralized", "neutralization", "neutralizing", etc.), binding to in any capacity, immobilize, counteract, change, alter, modify.

The term "heparin" as used herein is generic to both traditional, naturally occurring forms of heparin, as well as heparin derivatives and/or artificial forms of heparin. Heparin is a glycosaminoglycan and acts as an anticoagulant. The molecule has a negative charge density. Some forms of heparin have average molecular weights from 2 kDa to 30 kDa, such as between 12 kDa and 15 kDa. FIG. 1B depicts some embodiments of heparin. Low molecular weight embodiments of heparin include enoxaparin, dalteparin, fondaparinux, tinzaparin and ultra low molecular weight embodiments of heparin include semuloparin. Heparin sulfate is included within the genus of the term "heparin".

LMWH is enzymatically or chemically modified UFH with high bioavailability, predictable pharmacokinetics and dose-response and therefore has a lower risk of bleeding complications. Fondaparinux and idraparinux are synthetic versions of the pentasaccharide moiety responsible for anti-factor Xa activity in UFH and LMWH. However, the anticoagulant activity of LMWHs, fondaparinux and idraparinux cannot be fully neutralized with a currently available antidote (Makris et al. 2000 Br J. Haematol. 108:884-5). Ultra low molecular weight heparin such as semuloparin has high anti-factor Xa and residual anti-factor II a activities and is currently under development for treatment of venous thromboembolism (VTE) and Cancer therapy.

The term "polyol" as used herein denotes an alcohol including two or more hydroxyl groups. This includes diols, triols, tetrols, etc.

Figure 1B:
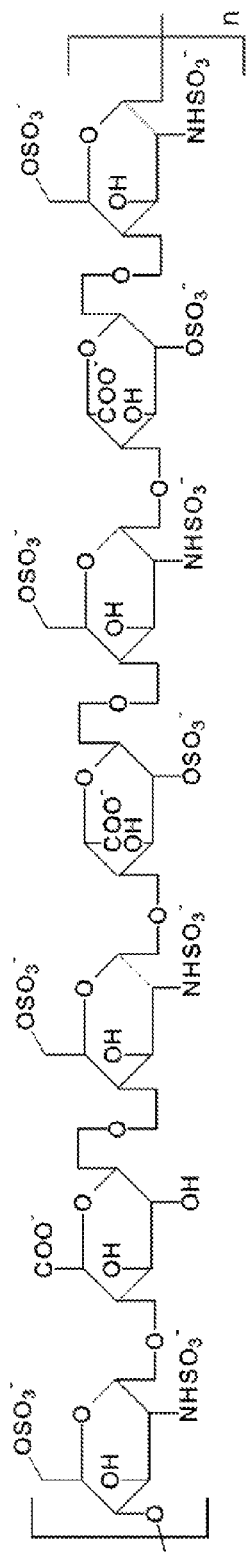
FIG. 1B depicts various forms of heparin.
Figure 1B:
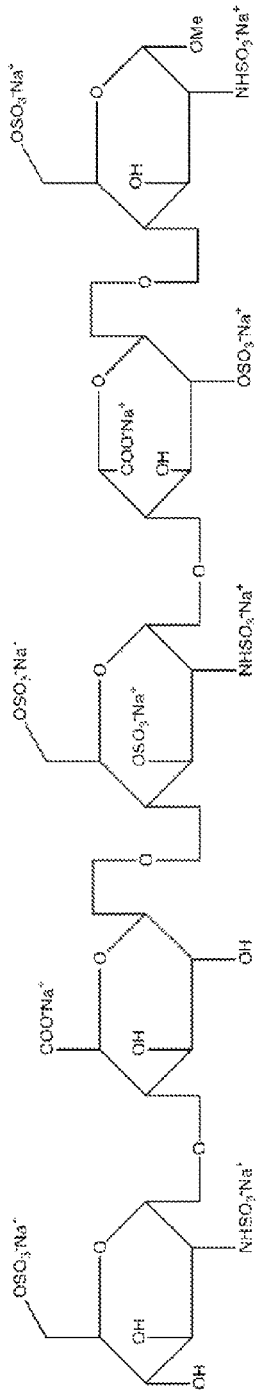
Figure 1B:
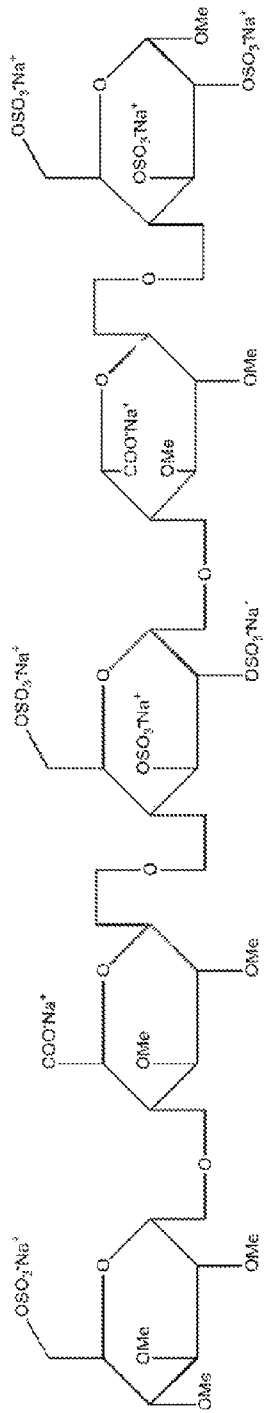
Figure 2A:
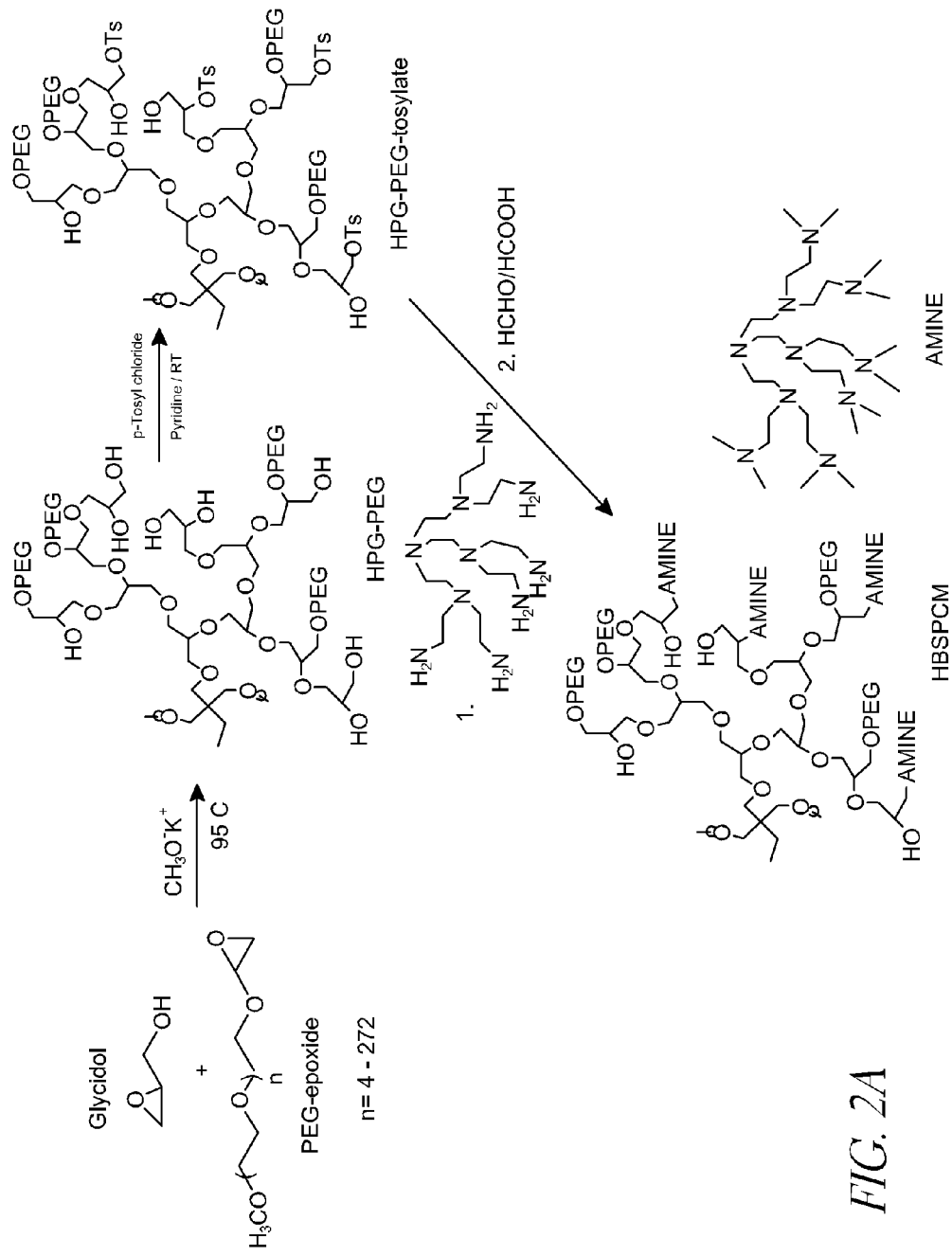
FIG. 2A is a depiction of some embodiments for the synthesis of heparin and heparin-derivative binding polymers with high charge density.
Figure 2B:
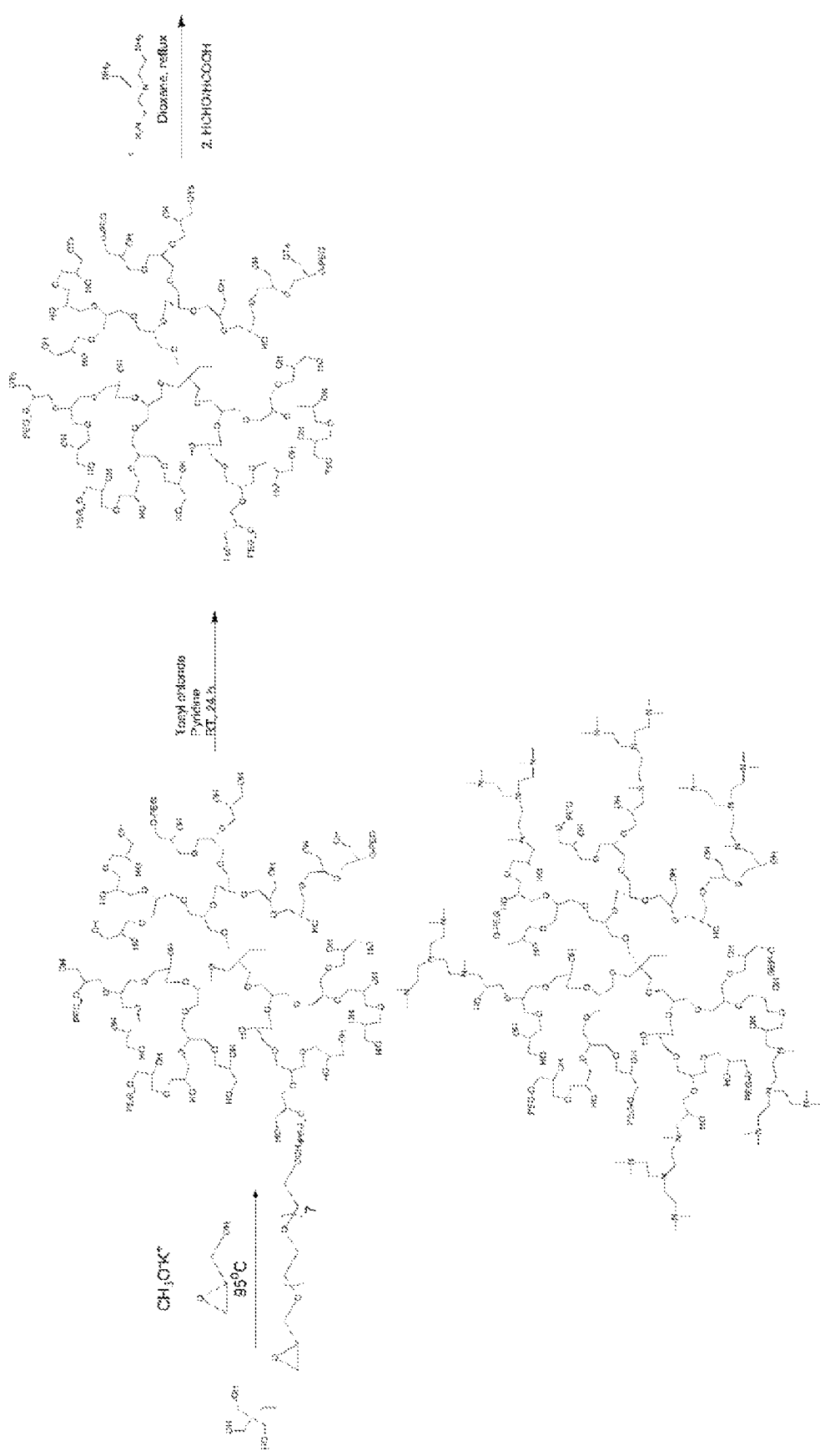
FIG. 2B is a depiction of some embodiments of the synthesis of heparin and heparin-derivative binding polymer with high charge density. The embodiment employs MPEG-400 and an amine with four nitrogen atoms.

The term "dendritic" when used in regard to polymers denotes a branching, tree-like structure (see, e.g., FIG. 1A or FIG. 2A). In some embodiments, dendritic polymers can have a large number of end functional groups and have low melt and solution viscosities.

The term "cationic moiety" denotes a chemical moiety that has a positive charge.

The term "protective moiety" denotes a chemical moiety that can assist in reducing non-specific interactions between a polyglycerol core and/or polyvalent cationic groups and chemicals other than heparin. Examples include, for example, polyethylene glycol.

The term "polyethylene glycol" or "PEG" denotes an oligomer and/or polymer of ethylene oxide and encompasses, for example, polyethylene oxide (PEO) and polyoxyethylene (POE).

The term "polyether polyol" denotes a polyol that has the ether functional group in the chain.

The term "hyperbranched" in reference to polymers denotes a polymer having 3 or more chain ends. In some embodiments, hyperbranched polymers are not perfectly branched. In some embodiments, hyperbranched polymers can be prepared in a one-step procedure. In some embodiments, hyperbranched polymers are molecular constructs having a branched structure, generally around a core. In some embodiments, their structure generally lacks symmetry, the base units or monomers used to construct the hyperbranched polymer can be of diverse nature and their distribution is non-uniform. In some embodiments, the branches of the polymer can be of different natures and lengths. In some embodiments, the number of base units, or monomers, can be different depending on the different branching. In some embodiments, while at the same time being asymmetrical, hyperbranched polymers can have: a branched structure, around a core, successive generations or layers of branching, and a layer of end chains. In some embodiments, the chain ends can be connected to cationic moieties and/or protective moieties. In some embodiments, there are three to 100,000 chain ends, e.g., 3-50,000, 3-20,000, 3-10,000, 3-5,000, or 100-1000.

Figure 13B:
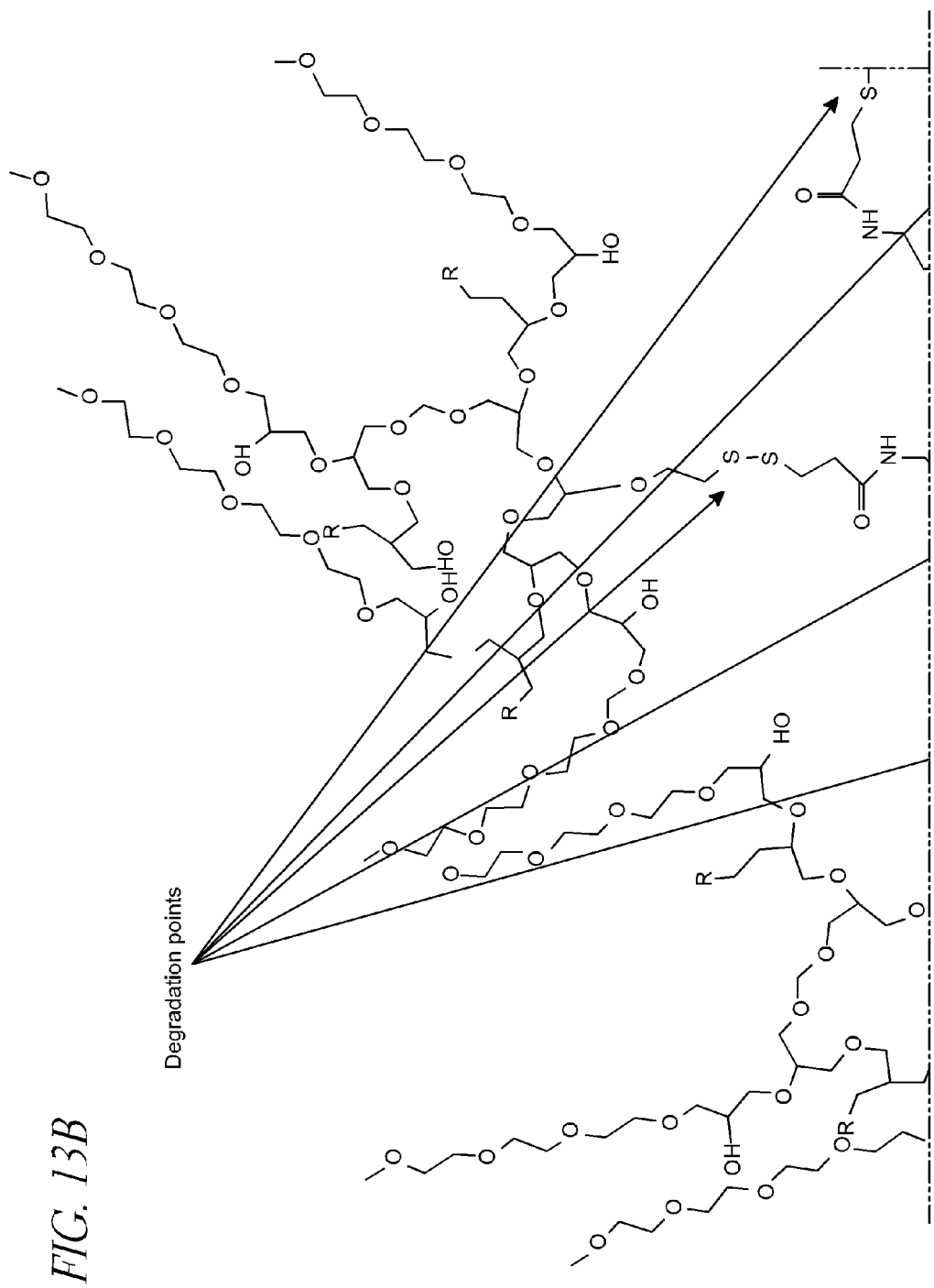
FIG. 13 is a synthetic scheme for disulfide-containing heparin binding synthetic polyvalent cationic macromolecule (HBSPCM).
Figure 13C:
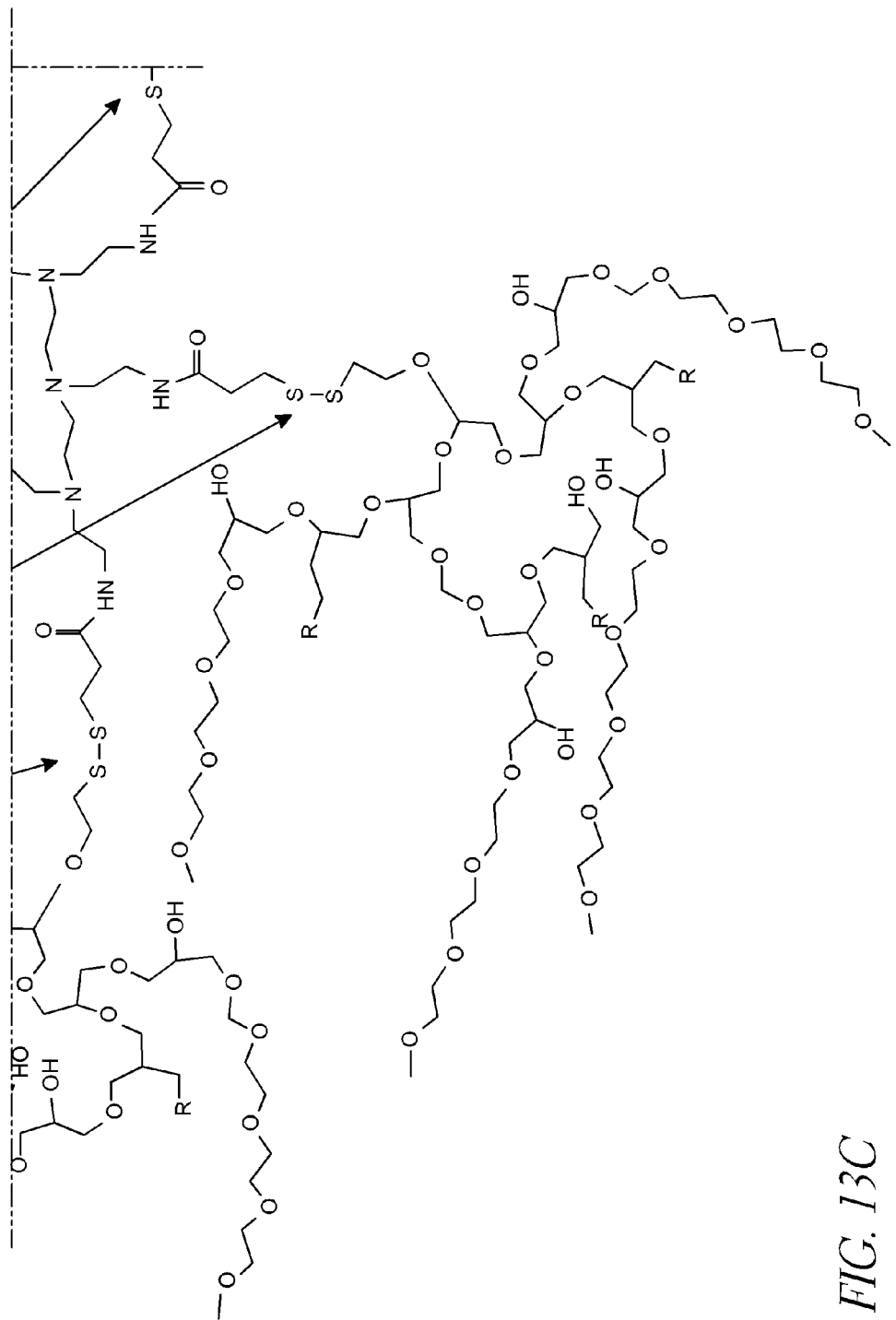
Figure 13D:
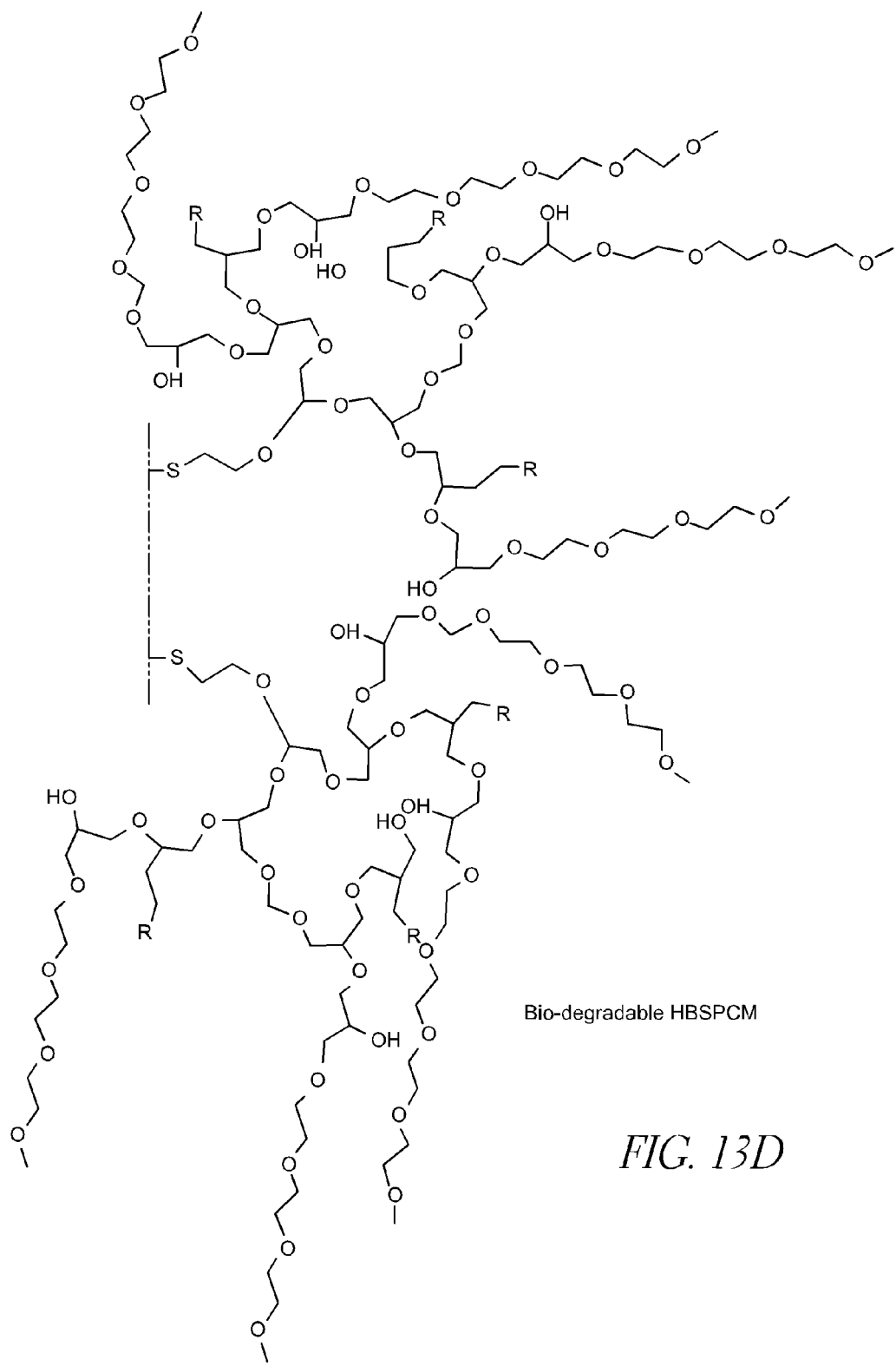

The term "cleavage site" denotes a bond that can be selectively cleaved over the remaining section of the polymer backbone. Cleavage sites include, for example, disulfide bonds and ketal groups (see, e.g., FIG. 13. and FIG. 14).

The term "ketal" group denotes a compound that includes the general Formula: Ia:

Formula (Ia)

$R^1$ and $R^2$ can be an alkyl or aryl.

An "amine" denotes an organic compound and/or functional group that include a basic nitrogen with a lone pair.

The term "alkyl," as used herein, means any unbranched or branched, substituted or unsubstituted, saturated hydrocarbon, with $C_1$-$C_{12}$ unbranched, saturated, unsubstituted hydrocarbons, including, e.g., methyl, ethyl, isobutyl, and tert-butylpropyl, and pentyl.

The term "alkoxy" refers to any unbranched, or branched, substituted or unsubstituted, saturated or unsaturated ether, including $C_1$-$C_6$ unbranched, saturated, unsubstituted ethers. Dimethyl, diethyl, methyl-isobutyl, and methyl-tert-butyl ethers also included. The term "cycloalkoxy" refers to any non-aromatic hydrocarbon ring, including those having five to twelve atoms in the ring.

The "number average molecular weight" or "Mn" is the ordinary arithmetic mean or average of the molecular weights of the individual macromolecules. It can be determined by measuring the molecular weight of n polymer molecules, summing the weights, and dividing by n.

The phrase "degree of pegylation" denotes the fraction of the total end-functional (hydroxyl) groups of the macromolecule that has been modified with polyethylene glycol (PEG).

A glycidol is an organic compound that includes both an epoxide and alcohol functional groups linked by a methylene ($CH_2$) group or $(CH_2)_n$ where n=2-10.

The term "hydrodynamic radius" denotes a theoretical hydrodynamic radius $R_{hyd}$. $R_{hyd}$ is defined by:

$$\frac{1}{R_{hyd}} \stackrel{def}{=} \frac{1}{N^2} \left\langle \sum_{i \neq j} \frac{1}{r_{ij}} \right\rangle$$

where $r_{ij}$ is the distance between subparticles i and j, and where the angular brackets $\langle \ldots \rangle$ represent an ensemble average.

General Embodiments

Heparin Binding Molecules

In some embodiments, the heparin binding molecule is a heparin binding polymer. In some embodiments, the heparin binding polymer can include a first dendritic polyol and one or more cationic moieties attached to the first dendritic polyol. In some embodiments the heparin binding polymer can include a first linear polyol and one or more cationic moieties attached to the first linear polyol.

In some embodiments, the heparin binding polymer can further include a protective moiety covalently attached to the first dendritic polyol. In some embodiments, the protective moiety includes polyethylene glycol (e.g., as shown in FIG. 1A). In some embodiments, a new layer of polyglycerol can be a protective moiety. In some embodiments, the protective moiety can be a biocompatible polymer such as polyvinyl pyrolidone, carbohydrate polymers, polypeptides, linear polyglycerol, polymers and copolymers of PEG acrylates and methacrylates, PEG acrylamide and methacrylamides.

In some embodiments, the heparin binding polymer is a polyether polyol. In some embodiments, the heparin binding polymer is a carbohydrate polymers, linear polyglycerol, polypeptides, branched or linear polymers and copolymers of PEG acrylates and methacrylates, PEG acrylamide and methacrylamides.

In some embodiments, the polyether polyol can be hyperbranched. In some embodiments, the degree of branching in the range of 0.0 to 0.95, for example, in the range of 0.0, 0.05, 0.1 to 0.9, 0.2-0.7, 0.4-0.65, or about 0.5. In some embodiments, the heparin binding polymer is a hyperbranched polyglycerol or a linear polyglycerol.

In some embodiments, the heparin binding polymer can include a polyether polyol, which can be attached to a support. In some embodiments, the heparin binding polymer is attached to the support via a disulfide bond. In some embodiments, the polymer is attached to the support via an acetal bond or a ketal bond. The support can be any material to which the molecule can be attached. In some embodiments, the support can be a bead or a flat surface.

In some embodiments, the heparin binding polymer includes a core unit that includes a $C_{1-18}$ alkyl substituted with two or more of $—OR^1$. In some embodiments, each $R^1$ is independently selected from at least one of: a hydrogen, a cationic moiety, and a polymer segment having monomer units represented by Formula (III):

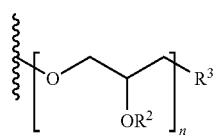

(III)

n can be an integer from 1 to 10,000 (or 0 to 10,000). Each $R^2$ can be independently selected from: a hydrogen, carbon, a cationic moiety, $R^1$, and a polymer segment represented by Formula (IV):

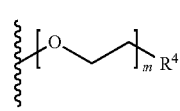

(IV)

m can be an integer from 1 to 10,000 or 0 to 10,000.

Each $R^3$ can be independently selected from: an oxygen cationic moiety, a hydroxyl, and a polymer segment represented by Formula (IV). m can be an integer from 1 to 10,000 (or 0 to 10,000) and each $R^4$ can be a $C_{1-6}$ alkoxy.

In some embodiments, the core unit is represented by Formula (V):

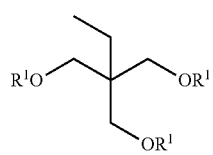

(V)

In some embodiments, the cationic moiety includes Formula (VI):

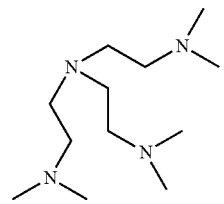

(VI)

wherein the heparin binding polymer includes an average of 4 to 250 cationic moieties. In some embodiments, the heparin binding polymer includes an average of 1, 2, 4, 5, 16, 20, 24, 23, 8, 11, 16, or 36 cationic moieties. In some embodiments, the polymer segment can be represented by Formula (IV):

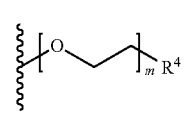

(IV)

and includes a polyethylene glycol having a size of 400 Da.

In some embodiments, the number average molecular weight (Mn) of the polymer segment represented by Formula (IV) is about 400 Da. In some embodiments, the average molecular weight (Mn) of the polymer segment represented by Formula (IV) is between 50 and 40,000 Da, for example 100 to 800, 200 to 700, 300 to 600, 300 to 500, or 350 to 450.

In some embodiments, the heparin binding polymer has a degree of PEGylation that is from about 5% to about 95%. In some embodiments, the polymer has a degree of PEGylation that is from about 20% to about 40%.

In some embodiments, the cationic moiety is selected from at least one of the group of: Formula (VI), Formula (VII), and Formula (VIII)

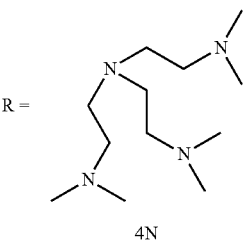

(VI)

4N

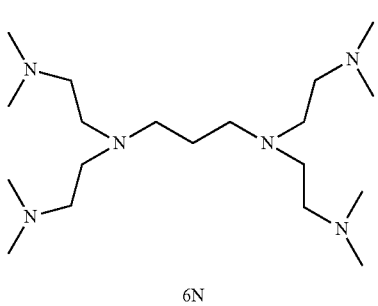

(VII)

6N

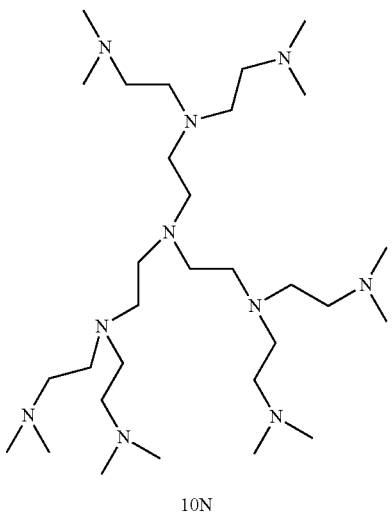

(VIII)

10N

In some embodiments, the heparin binding polymer is at least one of: JNK-4, JNK-5, JNK-6, JNK-3, JNK-7, JNK-8, JNK-9, JNK-10, JNK-11, and any combination thereof.

In some embodiments, the heparin binding molecule is a hyperbranched polyether polyol, which can be a hyperbranched polyglycerol (HPG).

In some embodiments, the hyperbranched polyether polyol polymer structure is a synthetic polycationic dendritic polymer based on HPG capped with short chain polyethylene glycols (PEGs) to create a macromolecule.

In some embodiments, the hyperbranched polyether polyol can further include one or more tetra (4 nitrogens) amine groups. In some embodiments, the hyperbranched polyether polyol can include one or more hexa (6 nitrogens), octa (8 nitrogens), or deca (10 nitrogens) amine groups.

In some embodiments, the hyperbranched polyether polyol can be of varying molecular weights of varying charge to optimize the reversal of anticoagulation due to a specific heparin species, such as low molecular weight heparin, or to otherwise optimize the administration of the polymer to a subject.

In some embodiments, the heparin binding polymer is the polymer shown in FIG. 1A. In some embodiments, the heparin binding polymer shown in FIG. 1A lacks the PEG groups in FIG. 1A (and thus would not be a "macromolecule" as the term is used herein). In some embodiments, one can employ a polymer that lacks PEG for heparin neutralization. In some embodiments, the heparin binding polymer is part of a macromolecule (as shown in FIG. 1A and FIG. 3).

In some embodiments, the heparin binding polymer has one or more R groups that includes 4, 6, 8, or 10 nitrogens. In some embodiments, each R group of the heparin binding polymer has 1, 2, 3, 4, 5, 6, 7, 8, 9, 10, 11, 12, 13, 14, 15, 16, 17, 18, 19, 20, 22, 25, 30 or more nitrogens, including any range defined between any two of the preceding values and any range greater than any one of the preceding values.

In some embodiments, all of the R groups for a particular heparin binding polymer are the same. In some embodiments, a single heparin binding polymer can have different types and/or sizes of R groups. In some embodiments, a single heparin binding polymer can have two or more of 4N, 6N, 8N and 10N R groups. In some embodiments, the R groups are cationic groups. In some embodiments, the spacer between the nitrogen atoms in the R groups can be $(CH_2)_n$ where n=1 to 10 (e.g., 1, 2, 3, 4, 5, 6, 7, 8, 9, or 10) or the spacer can have a cyclic aliphatic structure.

In some embodiments, heparin binding polymers and/or hyperbranched polyglycidols (HPGs) can be synthesized using various methods known in the art (Kainthan et al. 2006 Biomacromolecules. 7(3):703-709; Kainthan et al. 2007 Biomaterials. 28(32): 4779-4787). In some embodiments, the heparin binding polymers and/or hyperbranched polyglycidol polymer is a heparin-binding synthetic polyvalent cationic macromolecule (HBSPCM), e.g., as shown in FIG. 1A. In such embodiments, the HBSPCM can incorporate multiple high binding cationic units (R) attached on a dendritic HPG core, and can be capped with short chain polyethylene glycols (PEGs) to generate a polyvalent cationic macromolecule, as shown in FIG. 1A. In some embodiments, the cationic unit (R) is a methylated tetramine with four cationic amine groups per cationic units (R=4N) and will produce high binding affinity for heparin and heparin derivatives. FIG. 3 is a graphical interpretation of one embodiment with a HPG core on which polyvalent cationic groups are attached (C) and capped with a protective barrier to non-specific interactions. In some embodiments, the protective barrier is composed of short chain PEGs of approximately 400 Da each. The presence of a protective layer of short chain PEGs on the HBSPCM makes it highly biocompatible.

In some embodiments, the hydroxyl groups on the dendritic HPG core will be used for adding cationic units to the HBSPCM. The number of hydroxyl group is equal to degree of polymerization; e.g., each 74 Da molecular weight will have one hydroxyl group. The design of HBSPCM enables multiple embodiments including, but not limited to, changing the number of cationic units, changing the size of the HPG core (molecular weight) while keeping the PEG chain length constant, and changing the number of PEG chains attached to HPG core.

In some embodiments, the HPG core capped with PEGs is modified in a controlled manner by the covalent attachment of multi-valent cationic groups through a three step synthetic method involving tosylation of hydroxyl groups, coupling with amines (or other cationic groups), and methylation as shown in FIGS. 2A and/or 2B. Possible amine groups include, but are not limited to, tetra-amine, hexa-amine, octa-amine, deca-amine groups, and any other amine groups disclosed herein. The HBSPCM properties such as, but not limited to, molecular weight, molecular weight distribution, PEG content, charge density and plasma residence time can be controlled by methods known in the literature, such as, but not limited to, the anionic ring opening polymerization of glycidol and MPEG-epoxide and similar methods (Kainthan et al. 2006 Biomacromolecules. 7(3):703-709; Nair et al. 2007 Prog Polymer Sci. 32(8-9):762-798; Nisha et al. 2004 Langmuir. 20(6):2386-2396; Nisha et al. 2004 Langmuir. 20(20): 8468-8475; Kizhakkedathu et al. 2005 Macromol. Biosci. 5(6):549-558).

Examples of synthesized HBSPCMs are shown in Tables 1, 2, and 3. Two embodiments, JNK-1 (116 000 Da) and JNK-2 (48 000 Da), have 69 and 28 cationic groups (R; 4 charges/ cationic group), respectively. The hydrodynamic radii of these molecules are in the range of 4 to 10 nm with a PEG content of approximately 75% by weight.

In some embodiments, the interactions between cationic and anionic charges are maximized due to the dendritic nature of the HPG core and PEG caps (maximum surface exposure of charges and multivalent effect). This characteristic has advantages over linear polymers, which cannot maximize surface exposure of charges.

Figure 14A:
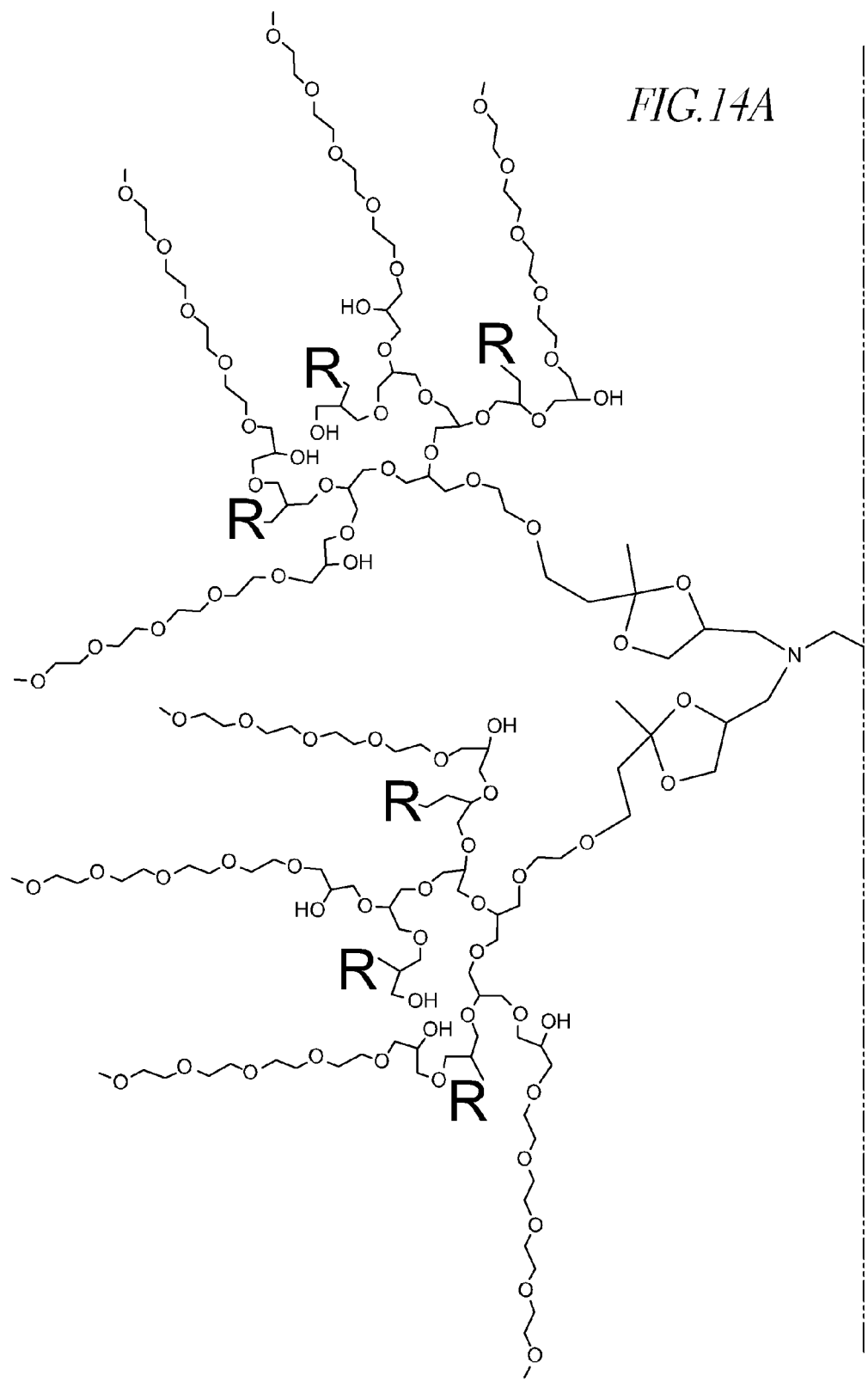
FIG. 14 is a depiction of a structure of a ketal group-containing heparin binding synthetic polyvalent cationic macromolecule (HBSPCM).
Figure 14B:
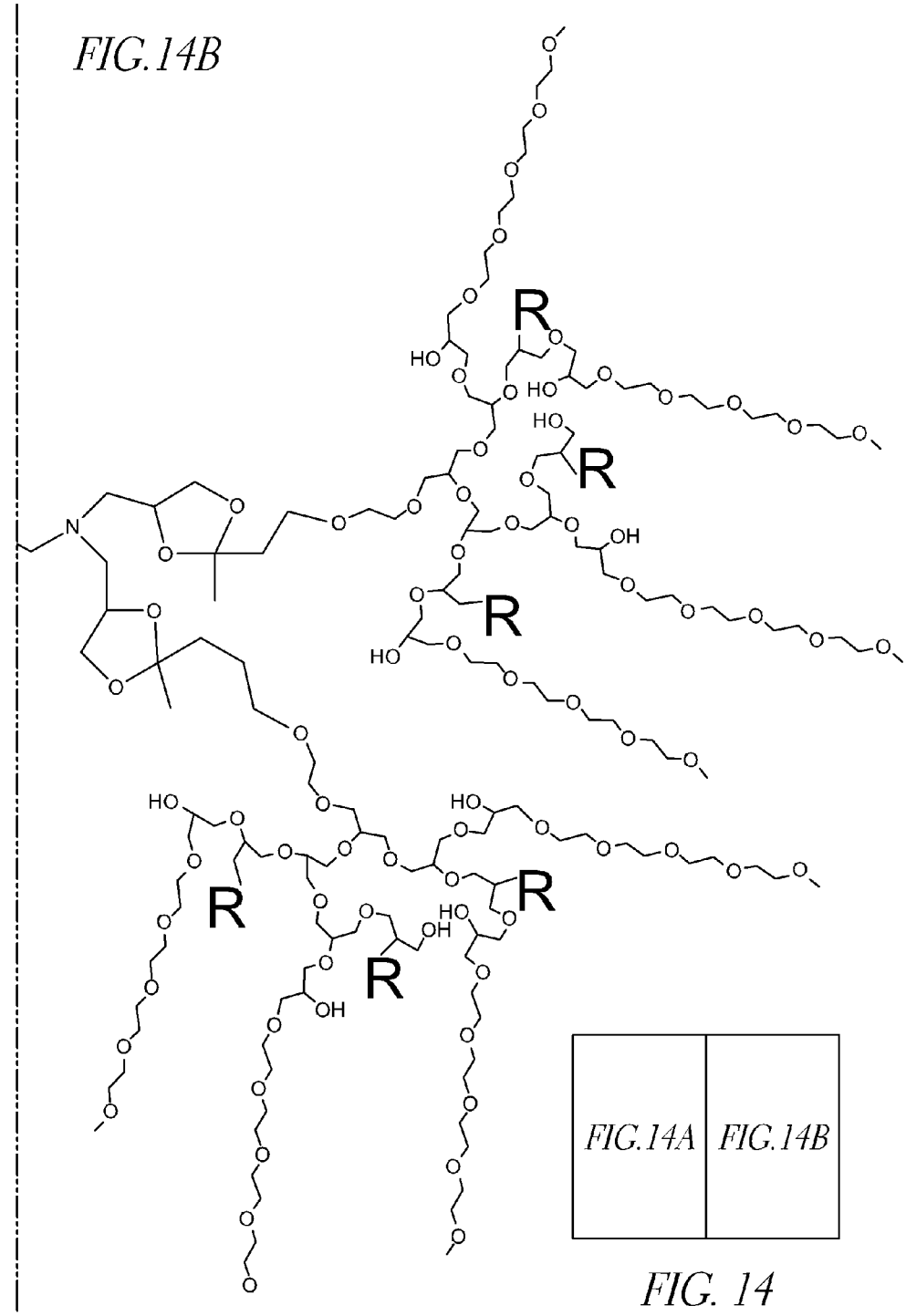
Figure 14:
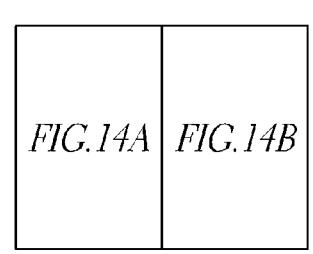

In some embodiments of the technology, biodegradable HBSPCMs are synthesized for optimal clearance of HBSPCM and its complexes from the vascular system and from the body. These HBSPCMs will have precise degradation points. Degradation points can be constructed from one or more elements from the following categories including, but not limited to, disulphide bonds (FIG. 13) and ketal groups (FIG. 14). In one embodiment, the disulfide initiator is prepared by reaction of octa-amine and 2 hydroxy, 2'-carboxy ethylene disulfide (FIG. 14). Since the disulfide bonds are cleaved by glutathione inside the cell, it will stable in vascular system. In another embodiment, ketal groups are cleaved by the pH in endosomes in the cell. Since ketal groups are stable at physiological pH and above, this embodiment of the HBSPCM will be stable in blood as well as during the chemical modification.

TABLE 1

CHARACTERISTICS OF JNK-1 AND JNK-2 HBSPCM POLYMERS

| Sample | Molecular weight (Da) | No. cationic units (R) of 4 amines each | Average no. of charges | Zeta potential (mV) | Kb (M-1) [1] | C50 (nM) [1] | Rh (nm) | Blood compatibility at 1 mg/ml |
|---|---|---|---|---|---|---|---|---|
| JNK-1 | 116 700 | 69 | 276 | 11.4 ± 2.9 | 1 108 | 10 | 10 | excellent |
| JNK-2 | 48 000 | 28 | 112 | 11.1 ± 2.1 | ND | ND | 4 | excellent |
| Protamine | ~4500 | — | 21 | ND | ND | ND | ND | poor [3] |
| Tetramine (spermine) | 146 | — | 4 | ND | 3.6 105 | 2788 | ND | poor |
| PEG-based linear cationic polymer [4] | 1.8 106 | — | ND | ND | 1 104 | 100000 | ND | ND |

PEG = polyethylene glycols.
Rh = hydrodynamic radius.
ND = no data.
[1] Binding affinity of polymers for ctDNA (a highly anionic bio-macromolecule) in buffered water (pH 7.2) in the presence of 50 mM NaCl at 25° C.
[3] Showed complement activation, platelet activation, behaved like an anticoagulant, showed massive hemolysis.
[4] Nisha et al. 2004 Langmuir. 20(6): 2386-2396.

Figures 1, 2B:
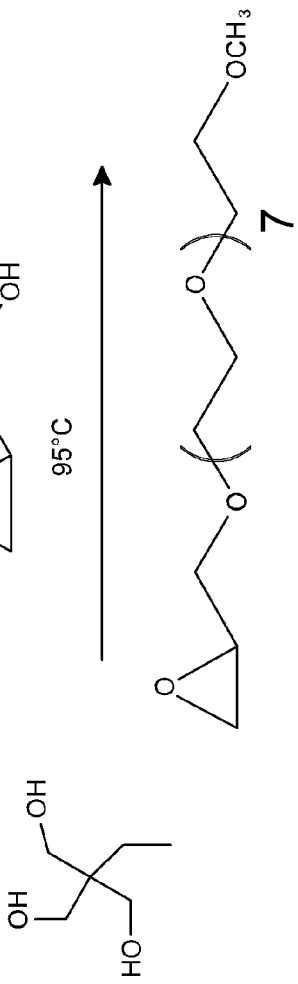
Figures 2, 2B:
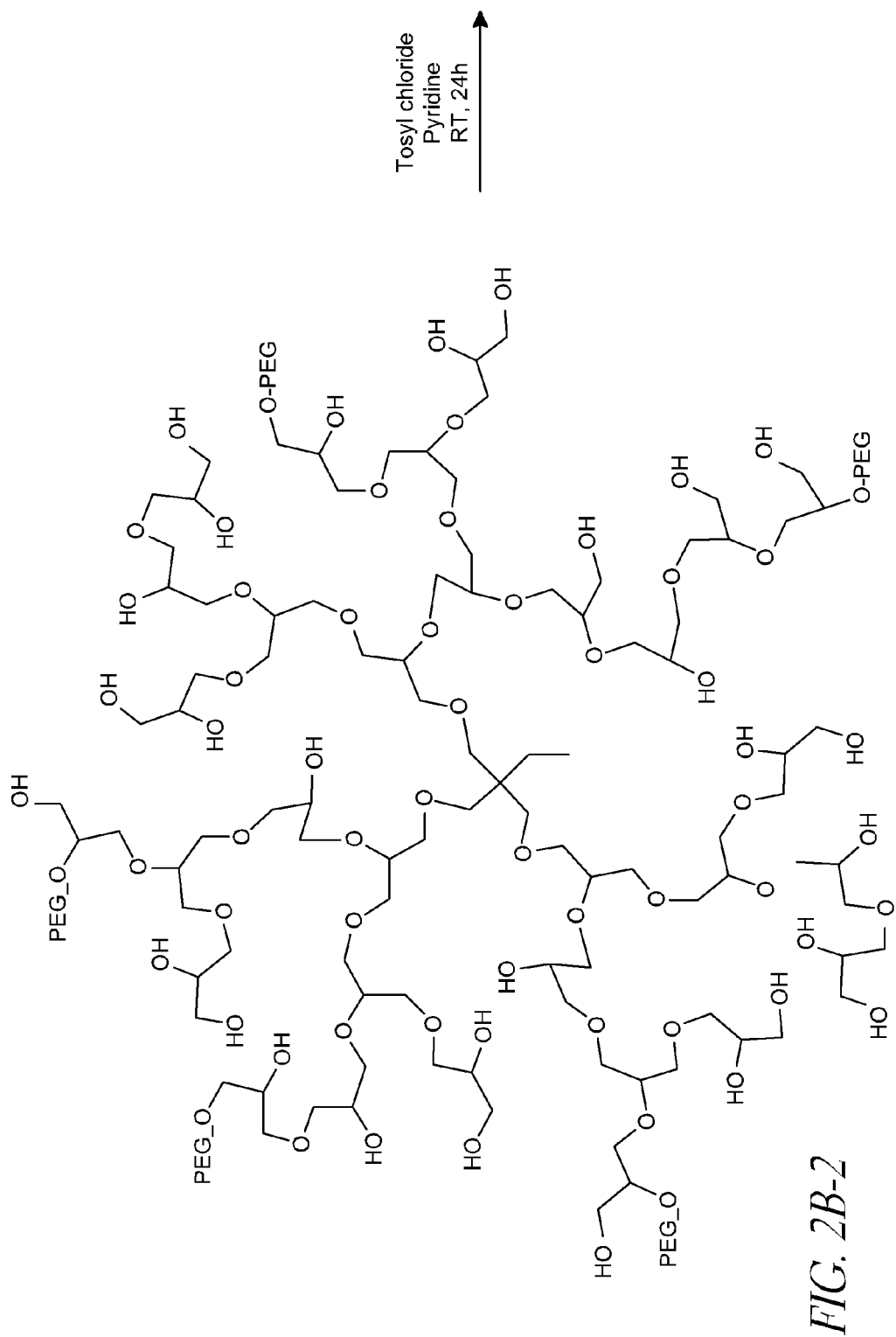
Figures 2, 2B, 3:
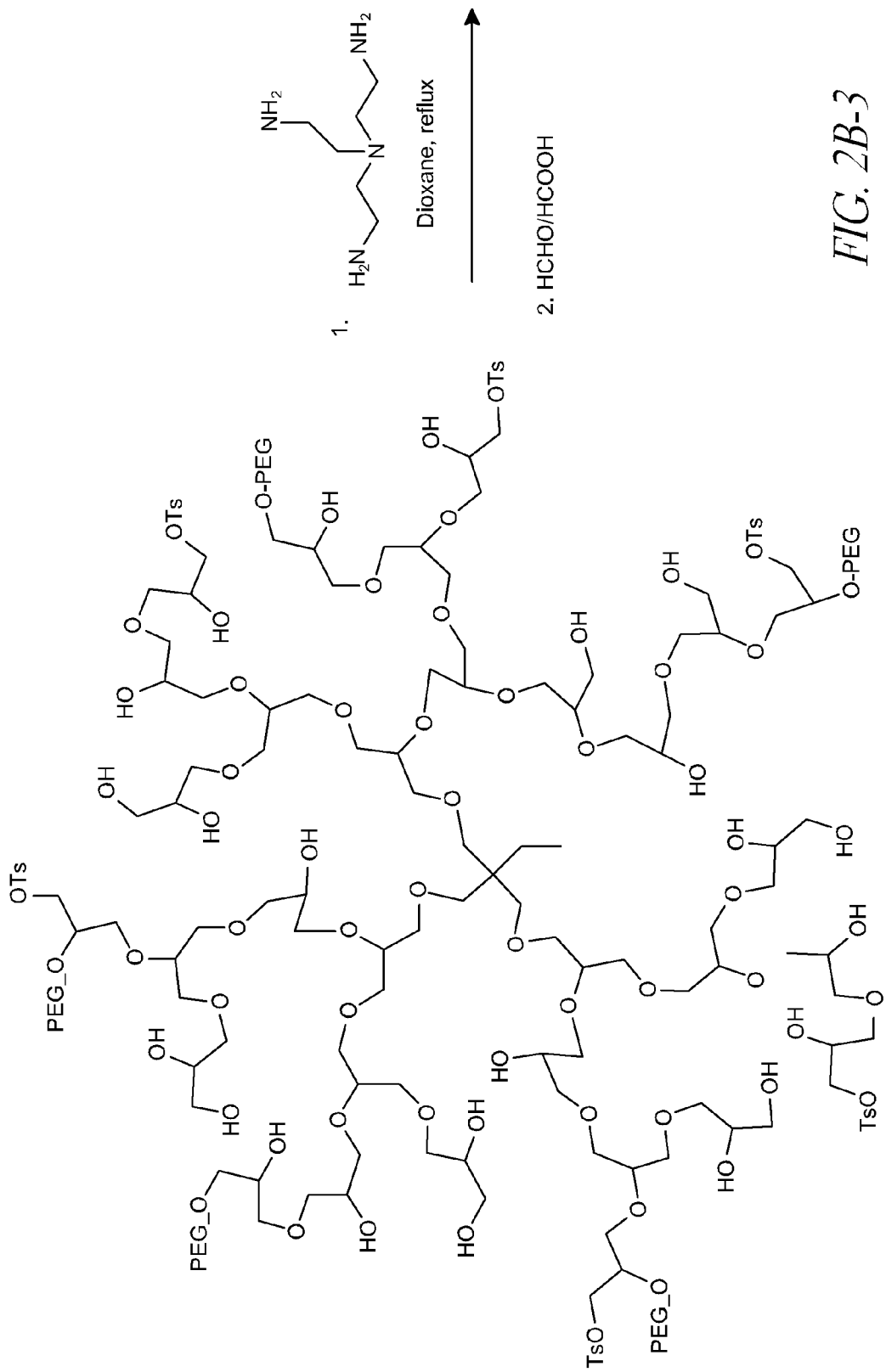
FIG. 3 is a depiction of an embodiment of the design of heparin binding synthetic polyvalent cationic macromolecule (HBSPCM).
Figures 2, 2B, 3, 4:
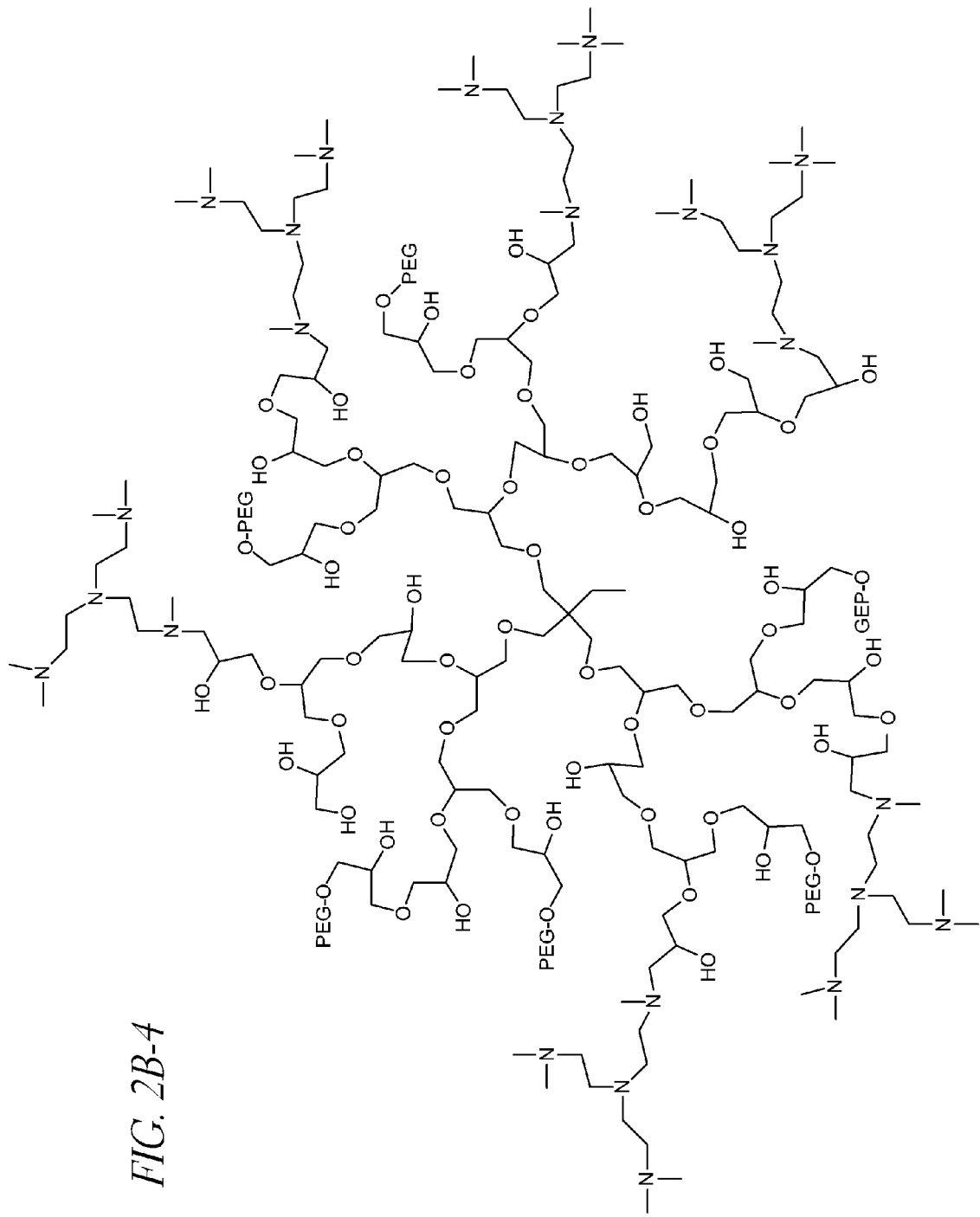
Figure 3:
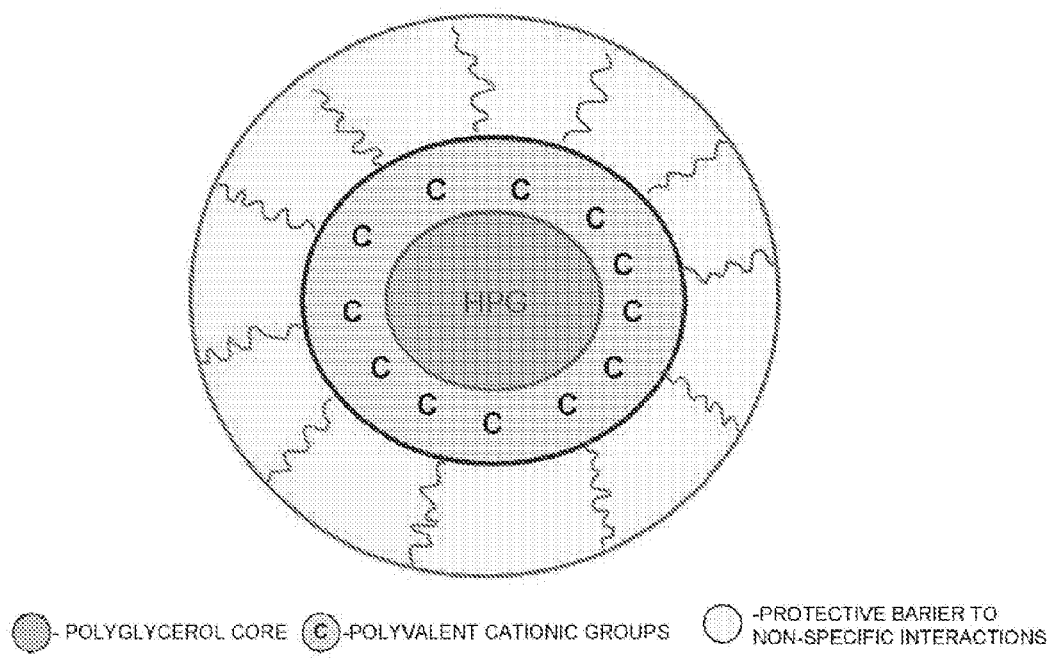

In some embodiments, the binding affinity and charge density of HBSPCMs can be increased by incorporating hexa amine cationic units with six nitrogens per unit instead of tetramine cationic units (FIG. 1). In some embodiments deca amine cationic units with 10 nitrogens per unit instead of tetramine units (FIG. 1) are provided. In some embodiments, the HBSPCM structure is optimized using tosylation of HPG hydroxyl groups for the neutralization of heparin derivatives with a smaller number of negative charges than LMWH or UFH. In some embodiments, the HBSPCM structure is optimized using reductive amination of HPG for the neutralization of heparin derivatives.

In some embodiments, the number of cationic units (R) is lower and varies, each having four cationic amine groups per cationic unit and giving a total charge per polymer of 4×R. For example, the number of cationic units (R) can range from 4 to 24, giving a range of 16 to 96 for charges per polymer. Table 2 lists the characteristics of such polymers, each with a molecular weight of 23 kDa, that have been synthesized in some embodiments with different numbers of R groups, and hence charge per polymer, as well as different amine contents. In some situations, JNK-8 can be considered a control because it is a HBSPCM polymer without methylation of the amines, whereas in the other HBSPCM polymers in Table 2 the primary amine groups are dimethylated.

TABLE 2

CHARACTERISTICS OF HBSPCMS AT 23,000 G/MOL WITH DIFFERENT CHARGES

| | No. cationic units (R) of 4 amines each | Average no. of charges per polymer | Average amine content (% N) |
|---|---|---|---|
| JNK-4 | 4 | 16 | 3.0 |
| JNK-5 | 5 | 20 | 5.0 |
| JNK-6 | 16 | 64 | 13 |
| JNK-3 | 20 | 80 | 17 |
| JNK-7 | 24 | 96 | 21 |
| JNK-8 (Control) | 23 | 92 | 17.5 |

In some embodiments, the molecular weight of the HBSPCMs is varied in addition to the number of charges per polymer. For example, Table 3 lists three additional polymers (JNK-9, JNK-10 and JNK-11) with molecular weights of 9, 10, and 16 kDa, respectively, and number of charges per polymer of 32, 44 and 64, respectively.

TABLE 3

CHARACTERISTICS OF HBSPCMS WITH DIFFERENT MOLECULAR WEIGHTS

| Sample | Molecular weight (Da) | Average No. cationic units (R) of 4 amines each | Average no. of charges per polymer | Average amine content (% N) |
|---|---|---|---|---|
| JNK-9 | 9 000 | 8 | 32 | 16.4 |
| JNK-10 | 10 000 | 11 | 44 | 20.9 |
| JNK-11 | 16 000 | 16 | 64 | 19.6 |

Cationic Groups

In some embodiments, the heparin binding polymer further includes a cationic moiety. In some embodiments, the cationic moiety includes an amine group. In some embodiments, the cationic moiety can be arginine, secondary amine and primary amine groups, and/or N-methylated lysine. In some embodiments, the amine is covalently attached to the polyol. In some embodiments, the cationic moiety includes an arginine. In some embodiments, the amine group is a tetra-amine group, hexa-amine group, and/or a deca-amine group.

In some embodiments, the heparin binding polymer includes 1-300 cationic moieties, for example 2-200, 3-150, 4-100, 5-50, 6-40, or 7-30. In some embodiments, the heparin binding polymer has 1 to 100 cationic moieties, for example, 2, 3, 4, 5, 6, 7, 8, 9, 10, 15, 20, 25, 30, 35, 40, 50, 60, 70, 80, 90, or 99 charges, including any amount between any of the two preceding values. In some embodiments, the polymer has 4 to 23 cationic moieties. In some embodiments, the polymer has 16 to 92 cationic charges.

Cleavage Sites

In some embodiments the heparin binding polymer can include one or more cleavage site within the polymer. In some embodiments, there are 1, 2, 3, 4, 5, 6, 7, 8, 9, 10, 15, 20, 25, 30, 40, 50, 60, 80, 100, or 200, including any range greater than any of the preceding values and any range defined between any two of the preceding values. In some embodiments, there are 1-10 cleavage sites. In some embodiments, the heparin binding polymer includes a second dendritic polyol, where the at least one cleavage site links the first dendritic polyol to the second dendritic polyol.

In some embodiments, the cleavage site can be a disulfide bond. In some embodiments the heparin binding polymer includes at least two sulfurs that form a disulfide bond. In some embodiments, the two sulfurs are part of the structure of Formula (I):

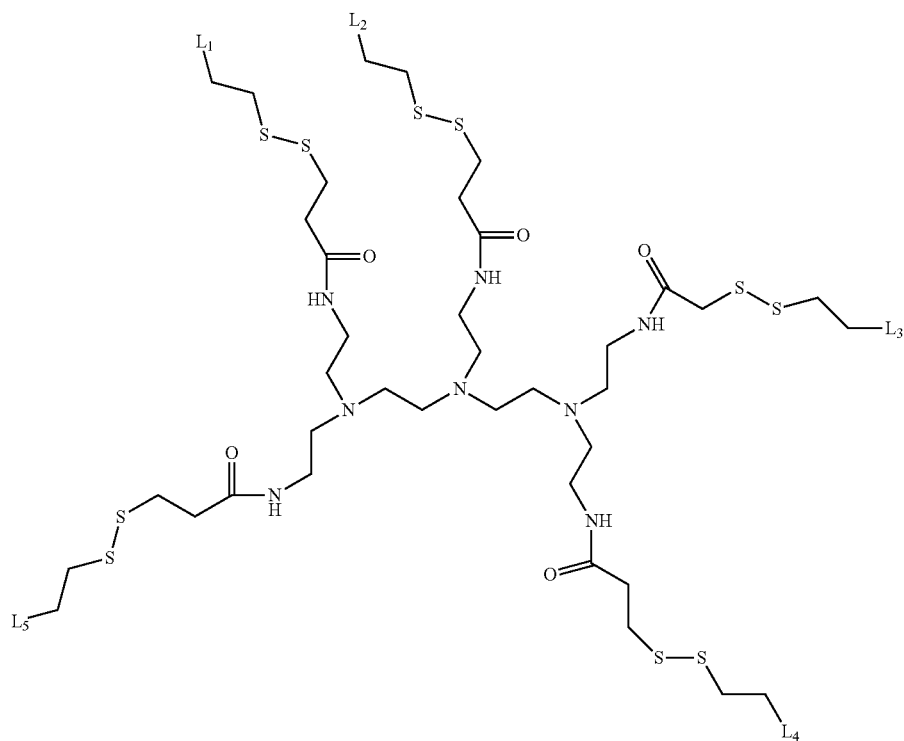

where $L_1$ can be a first dendritic polyol, $L_2$ can be a second dendritic polyol, $L_3$ can be a third dendritic polyol, $L_4$ can be a fourth dendritic polyol, and $L_5$ can be a fifth dendritic polyol.

In some embodiments, the heparin binding polymer can include at least one ketal group. In some embodiments there are 1, 2, 3, 4, 5, 6 7, 8, 9, 10, 12, 15, 20, 25, 30, 50, 80, 100 or more ketal groups and/or disulfide bonds in the heparin binding polymer. In some embodiments, the ketal group is part of the structure of Formula (II):

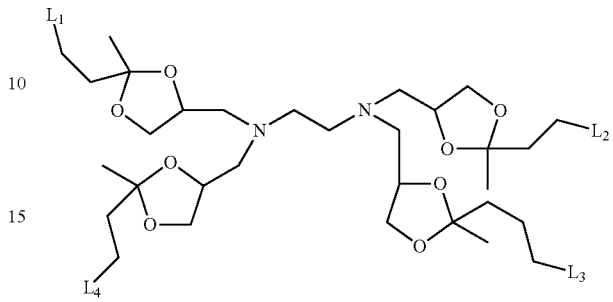

$L_1$ can be a first dendritic polyol. $L_2$ can be a second dendritic polyol. $L_3$ can be a third dendritic polyol. $L_4$ can be a fourth dendritic polyol.

In some embodiments, the hyperbranched polyether polyol can further include one or more ketal groups. In some embodiments, the hyperbranched polyether polyol containing one or more ketal groups is degraded to form smaller polymers of lower molecular weight. In some embodiments, the cleavage group can be that shown in FIG. 13. In some embodiments, the cleavage group can be that shown in FIG. 14.

In some embodiments, the hyperbranched polyether polyol can include one or more disulphide bonds. In some aspects, the hyperbranched polyether polyol containing one or more disulphide bonds is degraded to form smaller polymers of lower molecular weight.

Compositions and Pharmaceutical Formulations of Heparin Binding Polymers

In some embodiments, compositions including at least one HPG or heparin binding polymer can be administered at a pharmacologically effective amount in a pharmaceutically acceptable excipient to a subject previously administered with heparin, unfractionated heparin and/or a heparin derivative. Examples of heparin derivatives include, but are not limited to, unfractionated heparin, low molecular weight heparins, ultra low molecular weight heparins, fondaparinux, idraparinux, heparinoids and the like.

In some embodiments, a composition including at least two HPG polymers can be administered to a subject at a pharmacologically effective amount in a pharmaceutically acceptable excipient previously administered with heparin or a heparin derivative. The HPG polymers can have different molecular weights, different functional groups, different PEG group sizes, different charge density and the like, as described herein and known in the art. Additionally, other agents can be coadministered with at least one HPG polymer. Examples of such agents may include protamine, protamine derivatives, pharmaceutical excipients, and the like.

In some embodiments, a heparin binding composition is provided. The composition can include a first heparin binding polymer and a pharmaceutically acceptable carrier. In some embodiments, the composition can include a first heparin binding polymer and an anionic therapeutic agent (e.g. heparins, methetrexate, insulin) for the controlled drug delivery. The heparin binding polymer can be any of the heparin binding polymer embodiments disclosed herein. In some embodiments, the heparin binding polymer includes a first dendritic polyol and one or more cationic moieties attached to the first dendritic polyol. In some embodiments, the composition further includes a second heparin binding polymer. The second heparin binding polymer can be different from the first heparin binding polymer. In some embodiments, the composition can include a protamine, a protamine derivative, or a combination thereof.

In some embodiments, the first heparin binding polymer is present in a unit dose. In some embodiments, the unit dose of the first heparin binding polymer is between 10 mg per kg of subject to be treated and 200 mg per kg of subject to be treated. In some embodiments, the subject weighs between 1 kg and 200 kg, for example, between 5 kg and 150 kg, between 10 kg and 100 kg, or between 20 kg and 90 kg. In some embodiments, the composition includes between 100 mg and 40 g of the first heparin binding polymer, for example, between 500 mg and 20 g, between 1 g and 15 g, between 2 g and 10 g, or between 2 g and 5 g of the first heparin binding polymer.

In some embodiments, the heparin binding polymer can be prepared in a mixture with a pharmaceutically acceptable carrier and/or excipient. Therapeutic compositions can be administered intravenously, subcutaneously, topically or via catheters When administered systemically, therapeutic compositions can be sterile, pyrogen-free and in a parenterally acceptable solution having due regard for pH, isotonicity, and stability. These conditions are known to those skilled in the art. In some embodiments, dosage formulations of the compounds are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in Remington's Pharmaceutical Sciences (18$^{th}$ ed, Mack Publishing Company, Easton, Pa., 1990). For example, dissolution or suspension of the active compound in a vehicle such as water or naturally occurring vegetable oil like sesame, peanut, or cottonseed oil or a synthetic fatty vehicle like ethyl oleate or the like can be employed. Buffers, preservatives, antioxidants and the like can be incorporated according to accepted pharmaceutical practice.

In some embodiments, a heparin composition is provided. The heparin composition can include heparin and a heparin binding polymer. The heparin binding polymer can include a first dendritic polyol and one or more cationic moieties attached to the first dendritic polyol. In some embodiments, the heparin composition further includes blood or plasma. In some embodiments, the blood is human blood or the plasma is human plasma. In some embodiments, the heparin is selected from the group of low molecular weight heparin, fondaparinux, idraparinux, heparinoid, and any combination thereof.

In some embodiments, a method of making a heparin binding polymer is provided. The method can include polymerizing a glycidol and a methylated PEG-epoxide, to form a hyperbranched polyglycerol, tosylating the hyperbranched polyglycerol to form a tosylated hyperbranched polyglycerol, and coupling the tosylated hyperbranched polyglycerol with at least one amine group, thereby making a heparin binding polymer.

In some embodiments, the amine group is coupled to the polymer through a primary amino group. In some embodiments, following the coupling, the amino groups are methylated. In some embodiments, the amine group is a tetra-amine group, a hexa-amine group, or a deca-amine group. In some embodiments, the tosylating process occurs in the presence of pyridine and at room temperature. In some embodiments, it occurs between 20 and 30° C. In some embodiments, the polymerization process occurs at about 95 degrees C. In some embodiments, it occurs between about 95° C. to 120° C. and employs potassium methoxide. In some embodiments, it can employ potassium tert-butoxide, sodium hydride, or sodium naphthalide instead of potassium tert-butoxide, for example.

In some embodiments, molecules having cleavable bonds (HBSPCM polymer with biodegradable disulfide linkages) from an initiator with disulfide linkages. This disulfide containing initiator can be prepared, in some embodiments, by the reaction of the octamine with 2-hydroxy, 2'-carboxy ethylene disulfide. HBSPCM polymer with biodegradable ketal linkages can be prepared, in some embodiments, by using an initiator containing ketal groups. This initiator can be prepared, in some embodiments by first reacting ethylene diamine with 4 equivalents of glycidol, followed by reaction with 4-hydroxy-2-butanone.

Macromolecule

The term "macromolecule" as used herein denotes the presence of a protective substance associated with the polyol core and/or cationic group. The term heparin binding polymer encompasses various macromolecules and is a broader genus to the possible types of macromolecules that can employ heparin binding polymers. Examples of macromolecules are shown in FIG. 1A and FIG. 3.

In some embodiments, the macromolecule includes a protective barrier (although it need not actually surround or completely surround the core and/or cationic groups in all embodiments.

In some embodiments, the heparin binding macromolecule includes a hyperbranched polyglycidol core, at least one polyvalent cation attached to the hyperbranched polyglycidol core, and at least one protective moiety attached to the hyperbranched polyglycidol core. In some embodiments, this protective moiety includes polyethylene glycol.

In some embodiments, the macromolecule has a polyethelene glycol content between 50 and 95% by weight, e.g., 60-80%. In some embodiments the macromolecule has a polyethelene glycol content between 55% and 90%, 60% and 85%, 65% and 80%, 70% or 80% by weight. In some embodiments the macromolecule has a polyethelene glycol content of about 75% by weight.

In some embodiments, the polyvalent cation includes an amine group (such as one or more of those shown in FIG. 1A). In some embodiments, the amine group includes a methylated amine. In some embodiments, the amine can include an alkylated amine. In some embodiments, the amine group includes a methylated tetra-amine group, a methylated hexa-amine group, or a methylated deca-amine group. In some embodiments, the macromolecule has a hydrodynamic radius of about 4 nm and about 10 nm.

Any of the other embodiments disclosed herein (such as the presence of particular cationic groups, cleavage sites, etc.), can be used in combination with any of the macromolecule embodiments.

Devices, Kits, Compositions, and Ex Vivo Techniques

In some embodiments, a heparin binding device is provided. The device can include a support and a heparin binding polymer immobilized on the support. In some embodiments, the heparin binding polymer is any of the heparin binding polymers and/or macromolecules described herein. In some embodiments, the heparin binding polymer includes a first dendritic polyol and one or more cationic moieties attached to the first dendritic polyol.

In some embodiments, the support includes a surface of one or more beads. In some embodiments, the support includes metal, plastic, glass, or ceramic. In some embodiments, the support is a material that is biocompatible. In some embodiments, the material can be polyurethane, PVC, silicone, etc.

In some embodiments, the device also includes a fluid flow path configured to allow a fluid to flow through the fluid flow path while coming in contact with the heparin binding polymer on the support.

In some embodiments, the device also includes a pump configured to pump blood through the fluid flow path. In some embodiments, the pump is a peristaltic pump.

In some embodiments, the support upon or in which the heparin binding polymer is associated is, or is part of, a removable cartridge. In some embodiments, the removable cartridge allows for the replacement of one set of heparin binding polymers with a different set. In some embodiments, the cartridge allows for the ready replacement of a used set of heparin binding polymers with a new set of polymers.

In some embodiments, the support is part of the removable cartridge. In some embodiments, the support in the cartridge is configured so as to allow the support to be exposed to a fluid in the fluid flow path. In some embodiments, the heparin binding polymer is attached to a surface of the cartridge. In some embodiments, the removable cartridge, when engaged with the device, forms part of the flow path or an outer surface of the flow path. In some embodiments, the cartridge is configured such that the fluid flows over the support section of the cartridge. In some embodiments, the cartridge is configured such that the fluid flows through the support section of the cartridge (e.g., the support can be a filter or screen). In some embodiments, the cartridge is configured such that the fluid flows around and/or to the side of the support section of the cartridge (e.g., the support can be a structure that is inserted into the flow path itself).

In some embodiments, the device will include blood when in use. In some embodiments, the blood is mammalian, such as human, pig, horse, cow, mouse, etc.

In some embodiments, the fluid flow path includes a first inlet, through which unprocessed blood can enter the flow path, and an outlet, through which processed blood can exit the heparin binding device.

In some embodiments, the device includes a reservoir in fluid communication with a second inlet. In some embodiments, the reservoir includes one or more plasma constituents. In some embodiments, the reservoir includes one or more blood constituents. In some embodiments, the plasma constituents or the blood constituents include a non-heparin molecule that binds to the heparin binding polymer. In some embodiments, the reservoir contains a medicine for the treatment of at least one of the following: acute coronary syndrome, atrial fibrillation, cardiac bypass, extracorporeal membrane oxygenation, pancreatitis, wounds, hemofiltration, inflammation, cancer and burns.

In some embodiments, the device includes tubing, or is the tubing itself, and the inside of the tubing is coated inside with a heparin binding polymer.

In some embodiments, HPG polymers can be used in an extracorporeal circuit having heparin or heparin derivatives induced into the blood for reuse in a subject, where the extracorporeal device contains HPG polymers to neutralize the heparin or heparin derivatives in the blood before returning it to the subject. In some embodiments, the HPG polymers are HBSPCM polymers attached to the part of the extracorporeal device coming into contact with blood.

In some embodiments, a kit is provided. The kit can include a first container that includes heparin and a second container that includes a heparin binding polymer. In some embodiments, the heparin binding polymer includes a first dendritic polyol and one or more cationic moieties attached to the first dendritic polyol. In some embodiments, the amount of heparin binding polymer included is sufficient to bind to the amount of heparin included. In some embodiments, the heparin binding polymer is divided into unit dosage amounts, such that the amount of heparin binding polymer in any single dose amount is sufficient to bind to a standard dose of heparin. In some embodiments, the kit can include a needle and/or tubing for withdrawing blood from a subject. In some embodiments, the kit can include cartridges and/or a device as described herein. In some embodiments, the kit can include one or more syringes. In some embodiments, the syringe is sized so as to be capable of accepting a unit dose of heparin and/or the heparin binding polymer. In some embodiments, a unit dose of the heparin binding polymer is prefilled into the syringe. In some embodiments, the kit includes components for intravenous administration of the polymer. In some embodiments, material for measuring thrombin and/or Ma activity can also be included.

In some embodiments, a controlled release delivery device is provided. The device can include a surface and a heparin binding polymer attached to the surface. The heparin binding polymer can include a first dendritic polyol and one or more cationic moieties attached to the first dendritic polyol. In some embodiments, any of the polymers described herein can be employed. In some embodiments, the controlled release delivery device can also include heparin. In some embodiments, the heparin is bound to the heparin binding polymer. In some embodiments, the type of heparin can be any of the types described herein. In some embodiments, the amount of heparin is adequate for a specific therapeutic use. In some embodiments, the delivery device is adequately sterile for the use of the device in a subject, such as a human or mammal. In some embodiments, the controlled release delivery device allows for an extended release of heparin in a subject. In some embodiments, the controlled release delivery device allows for a lower amount of heparin to be administered to a subject. In some embodiments, the controlled release delivery device allows for relatively localized delivery of heparin. In some embodiments, instead of heparin, an anionic drug, such as methotrexate, phenoxymethyl penicillin, insulin, indomethacin, diclofenac, etc. can be used, thereby providing a controlled release anionic delivery device.

In some embodiments, a controlled release heparin composition is provided. In some embodiments, the composition can include a heparin binding polymer. In some embodiments, the heparin binding polymer can include a first dendritic polyol and one or more cationic moieties attached to the first dendritic polyol. In some embodiments, the controlled release heparin composition can also include heparin. In some embodiments, the heparin is bound to the heparin binding polymer. In some embodiments, the type of heparin can be any of the types described herein. In some embodiments, the amount of heparin is adequate for a specific therapeutic use. In some embodiments, the composition is adequately sterile for its application to a subject, such as a human or mammal. In some embodiments, the controlled release heparin binding composition allows for an extended release of heparin in a subject. In some embodiments, the controlled release heparin binding composition allows for a lower amount of heparin to be administered to a subject. In some embodiments, the controlled release heparin binding composition allows for relatively localized delivery of heparin. In some embodiments, instead of heparin, an anionic drug, such as methotrexate, phenoxymethyl penicillin, insulin, indomethacin, diclofenac, etc. can be used, thereby providing a controlled release anionic drug composition.

Methods of Using Heparin Binding Polymers

In some embodiments, methods are provided for neutralizing heparin, heparin derivatives, and/or heparinoids. The method can include administering a composition having at least one species of heparin binding polymer and/or hyperbranched polyether polyol polymers to a subject. The subject can have had a previous administration of heparin or heparin derivative.

In some embodiments, there is provided a method for neutralizing heparin or heparin derivatives, the method including directing the blood from a subject through an extracorporeal circuit that contains at least one species of heparin binding polymer and/or hyperbranched polyether polyol polymer before returning the blood to the subject for reuse. The subject may have had a previous administration of heparin, heparin derivative and/or heparinoids.

In some embodiments, a method of counteracting heparin in a subject is provided. In some embodiments, the method includes administering a heparin binding polymer to a subject. In some embodiments, the heparin binding polymer includes a first dendritic polyol and one or more cationic moieties attached to the first dendritic polyol. In some embodiments, the heparin binding polymer binds to heparin and thereby counteracts heparin in the subject. In some embodiments, the heparin binding polymer further includes polyethylene glycol covalently attached to the heparin binding polymer. In some embodiments, the cationic moiety is an amine group. In some embodiments, the amine group is a tetra-amine group, a hexa-amine group, or a deca-amine group. In some embodiments, the heparing binding polymer is any one or more of the heparing binding polymers and/or macromolecules provided herein.

In some embodiments, the method can include identifying a subject who has received an excess amount of heparin, wherein the identifying occurs before the heparin binding polymer is administered to the subject. In some embodiments, this can be done by identifying a subject who has received heparin in a clinical setting. In some embodiments, the excess amount of heparin was administered to the subject. In some embodiments, the excess amount of heparin was administered for the maintenance of an intravenous catheter or other hospital or medical care related treatment or service. In some embodiments, the excess amount of heparin was administered to treat one or more of the following: acute coronary syndrome, atrial fibrillation, cardiac bypass, extracorporeal membrane oxygenation, pancreatitis, hemofiltration, cancer therapy, or burns.

In some embodiments, the method includes identifying a subject that would benefit from reducing a level of exogenous heparin that is present in the subject's blood. In some embodiments, the subject will benefit from an accelerated removal of exogenous heparin from the subject.

In some embodiments, the method is performed in vivo. In some embodiments, the method is performed ex vivo. In some embodiments, blood is taken from a subject and heparin is removed from the blood and/or plasma via the heparin binding polymer. In some embodiments, the subject is a human. In some embodiments, the subject is not a human. In some embodiments, the subject is a dog, a cat, a horse, a cow, a pig, a mouse, a rat, a rabbit, a monkey, or a guinea pig.

In some embodiments, the heparin binding polymer can be administered subcutaneously. In some embodiments, the heparin binding polymer can be administered intravenously.

In some embodiments, a method of processing a subject's blood is provided. The method can include providing a heparin binding device. The heparin binding device can be one described herein. In some embodiments, the device can include a support and a heparin binding polymer immobilized on the support. The heparin binding polymer can include a first dendritic polyol and one or more cationic moieties attached to the first dendritic polyol. The method can further include withdrawing blood from a subject, contacting the blood to the heparin binding polymer, and returning at least part of the blood to the subject, thereby processing the subject's blood. In some embodiments, the process is done with and/or to the subject's plasma instead of blood. In some embodiments, the method further includes isolating plasma from the subject, treating the plasma to remove heparin, and then returning the plasma to the same subject and/or a different subject. In some embodiments, the subject's blood contains heparin. In some embodiments, the heparin is exogenous heparin. In some embodiments, the exogenous heparin binds to the heparin binding polymer and is thereby at least partially removed from the subject's blood.

In some embodiments, the method further includes the step of selecting a heparin binding polymer based upon the type of exogenous heparin administered to the subject. In some embodiments, the heparin binding polymer of a particular molecular weight is selected based upon the type of exogenous heparin. In some embodiments, this is done based upon the binding strength and neutralization capacity of the exogenous heparin. In some embodiments, a heparin binding polymer having a particular number of cationic groups is selected based upon the type of exogenous heparin. In some embodiments, the heparin binding polymer works for a majority of heparins or all heparins. In some embodiments, the heparin binding polymer works for negatively charged heparins, including derivatives thereof.

In some embodiments, returning at least part of the blood to the subject further includes fortifying the blood with one or more blood constituents that also bind to the heparin binding polymer. In some embodiments, the fortifying is performed after the blood has contacted the heparin binding polymer. In some embodiments, the blood can be fortified with negatively charged coagulation factors and/or proteins.

In some embodiments, a method of concentrating heparin is provided. In some embodiments, the method includes providing a support and a heparin binding polymer immobilized on the support. The heparin binding polymer can be any of the heparin binding polymers disclosed herein. In some embodiments, the heparin binding polymer includes a first dendritic polyol and one or more cationic moieties attached to the first dendritic polyol. In some embodiments, the method also includes contacting a first fluid that includes heparin with the heparin binding polymer and flowing the fluid off of the heparin binding polymer. This can concentrate the heparin.

In some embodiments, the first fluid includes blood. In some embodiments, the blood is human. In some embodiments, the fluid includes a cell lysate or other fluid from the manufacturing process of manufacturing heparin.

In some embodiments, the method further includes the process of removing the heparin from the heparin binding polymer. In some embodiments, the heparin is removed by flowing a second fluid including an ionic solution over the heparin binding polymer. In some embodiments, the first support is part of an affinity chromatography device. In some embodiments, the first fluid is derived from mucosal tissue from a meat animal. In some embodiments, the mucosal tissue from a meat animal is either porcine intestine, bovine lung, from cell culture, or a combination thereof.

In some embodiments, flowing the fluid off of the heparin binding polymer removes at least one impurity, thereby purifying the heparin.

In some embodiments, heparin binding polymer is used for the controlled delivery of anionic therapeutic agents such as heparins, methetrixate, insulin or similar for the treatments of VTE, cancer, inflammation or diabetes.

In some embodiments, the HBSPCM polymers are stable from −80° C. to 120° C. In some embodiments, heparin solutions are stable in the temperature range 4° C. to body temperature. In some embodiments, the methods can occur in part or in whole within one or both of the above temperature ranges.

In some embodiments, a polymer pad is provided. The polymer pad can be coated with any of the polymers disclosed herein. In some embodiments, this can be used as a controlled delivery platform for heparin based drugs or anionic drugs and/or for the local delivery of heparin. In some embodiments, the heparin binding polymer can be employed as a preventative, and thus can be applied prophylactically. In some embodiments the heparin binding polymers can be employed to treated heparin sulphate related disorders. For example, as a treatment or prophylactic for subjects who overexpress heparin sulphate.

EXAMPLES

Example 1

Synthesis of HPG-PEG-23K Precursor Polymer

The present example outlines a method of producing 23 kDa HBSPCM polymers; the synthesis steps include the following. Firstly, a HPG-PEG-23K precursor polymer was synthesized using the following steps. A three-necked round bottomed flask was cooled under vacuum and filled with argon. To this, 1,1,1-Tris(hydroxymethyl)propane (TMP, 0.480 g) and potassium methylate (25 wt % solution in methanol, 0.440 mL) were added and stirred for 30 minutes. Methanol was removed under vacuum for 4 hours. The flask was heated to 95° C. and glycidol (10 mL) was added over a period of 15 hours. After complete addition of monomer, the reaction mixture was stirred for additional 3 hours. MPEG-epoxide-400 (32 mL) was added over a period of 12 hours. The reaction mixture was stirred for additional 4 hours. The polymer was dissolved in methanol, passed through Amberlite IR-120H resin to remove the potassium ions and twice precipitated from diethyl ether. The polymer was dissolved in water and dialyzed against water using MWCO-1000 membrane for 3 days with periodic changes in water.

Example 2

Synthesis of JNK-5 Polymer

The JNK-5 polymer was synthesized from the HPG-PEG-23K precursor polymer described in the previous paragraph as follows. HPG-PEG-23K (0.5 g) was dissolved in 10 mL of pyridine. To this, p-toluene sulfonyl chloride (0.5 g) was added and stirred at room temperature for 24 hours. Pyridine was removed by rotary evaporation; the polymer was dissolved in 0.1 N HCl and dialyzed overnight. The polymer was isolated by freeze drying. HPG-PEG-Tos-23K-1 (0.4 g; polymer from previous step) and tris(2-aminoethylamine) (2 mL) were dissolved in 1,4-dioxane (10 mL) and refluxed for 24 hours. Dioxane was removed under vacuum, the polymer was dissolved in minimum amount of methanol and precipitated twice from diethyl ether. Polymer was dissolved in water and dialyzed against water using MWCO-1000 membrane for 2 days. The resulting polymer solution was added to a mixture of formaldehyde (3 mL) and formic acid (3 mL) at 0° C. The reaction mixture was refluxed overnight. After cooling to room temperature, the pH of the solution was adjusted to 10 using NaOH and the polymer was extracted with dichloromethane. Dichloromethane was removed under vacuum. The polymer was dissolved in water and dialyzed using MWCO-1000 membrane for 3 days. The yield of JNK-5 polymers was shown to be 0.3 g, and the amine content (by conductometric titration) was 4.8 mol %.

Example 3

Synthesis of JNK-3 Polymer

The HPG-PEG-23k precursor polymer (0.5 g) was dissolved in 10 mL of pyridine. To this, p-toluene sulfonyl chloride (1 g) was added and stirred at room temperature for 24 hours. Pyridine was removed by rotary evaporation; the polymer was dissolved in 0.1 N HCl and dialyzed overnight. The polymer was isolated by freeze drying. HPG-PEG-Tos-23K-2 (0.5 g; polymer from previous step) and tris(2-aminoethylamine) (4 mL) were dissolved in 1,4-dioxane (10 mL) and refluxed for 24 hours. Dioxane was removed under vacuum, the polymer was dissolved in minimum amount of methanol and precipitated twice from diethyl ether. Polymer was dissolved in water and dialyzed against water using MWCO-1000 membrane for 2 days. The resulting polymer solution was added to a mixture of formaldehyde (3 mL) and formic acid (3 mL) at 0° C.

The reaction mixture was refluxed overnight. After cooling to room temperature, the pH of the solution was adjusted to 10 using NaOH and the polymer was extracted with dichloromethane. Dichloromethane was removed under vacuum; the polymer dissolved in water and dialyzed using MWCO-1000 membrane for 3 days. The yield of JNK-3 polymers was shown to be 0.3 g, and the amine content (by conductometric titration) was 16.9 mol %.

Example 4

Synthesis of JNK-4 Polymer

The HPG-PEG-23k precursor polymer (0.5 g) was dissolved in 10 mL of pyridine. To this, p-toluene sulfonyl chloride (0.25 g) was added and stirred at room temperature for 24 hours. Pyridine was removed by rotary evaporation; the polymer was dissolved in 0.1N HCl and dialyzed overnight. The polymer was isolated by freeze drying. HPG-PEG-Tos-23K (0.4 g; polymer from previous step) and tris(2-aminoethylamine) (2 mL) were dissolved in 1,4-dioxane (10 mL) and refluxed for 24 hours. Dioxane was removed under vacuum, the polymer was dissolved in minimum amount of methanol and precipitated twice from diethyl ether. Polymer was dissolved in water and dialyzed against water using MWCO-1000 membrane for 2 days. The resulting polymer solution was added to a mixture of formaldehyde (2 mL) and formic acid (2 mL) at 0° C.

The reaction mixture was refluxed overnight. After cooling to room temperature, the pH of the solution was adjusted to 10 using NaOH and the polymer was extracted with dichloromethane. Dichloromethane was removed under vacuum; the polymer dissolved in water and dialyzed using MWCO-1000 membrane for 3 days. The yield of JNK-4 polymers was shown to be 0.25 g, and the amine content (by conductometric titration) was 3 mol %.

Example 5

Synthesis of JNK-6 and JNK-7 Polymers

The HPG-PEG-23k precursor polymer was used as starting polymer for the synthesis of the JNK-6 and JNK-7 polymers. To change the amine content of the polymer, different amounts of p-toluene sulfonyl chloride were used in the tosylation step. By controlling the amount of tosyl groups incorporated, the amine coupling was changed. All other experimental conditions for synthesis were the same as for the JNK-3 polymer.

Example 6

Synthesis of JNK-8 Polymer

The HPG-PEG-23k precursor polymer was used as starting polymer for the synthesis of the JNK-8 polymers. We followed similar experimental conditions and reagents as for the JNK-3 polymer except the last dimethylation using formaldehyde and formic acid, which was not performed. JNK-8 is a primary amine containing polymer without the dimethylation of amines.

Example 7

Synthesis of JNK-9 Polymer

Firstly, a precursor polymer HpG-PEG-9K was synthesized as follows. A three-necked round bottomed flask was cooled under vacuum and filled with argon. To this, 1,1,1-Tris (hydroxymethyl)propane (TMP, 0.240 g) and potassium methylate (25 wt % solution in methanol, 0.220 mL) were added and stirred for 30 minutes. Methanol was removed under vacuum for 4 hours. The flask was heated to 95 C and glycidol (3 mL) was added over a period of 15 hours. After complete addition of monomer, the reaction mixture was stirred for additional 3 hours. MPEG-epoxide-400 (10 mL) was added over a period of 12 hours. The reaction mixture was stirred for additional 4 hours. The polymer was dissolved in methanol, passed through Amberlite IR120H resin to remove the potassium ions and twice precipitated from diethyl ether. The polymer was fractional precipitated in methanol/ether mixture (1:25 v/v) to obtain HPG-PEG-9k polymer. The polymer was dissolved in water and dialyzed against water using MWCO-1000 membrane for 3 days with periodic changes in water.

Secondly, a precursor polymer HPG-PEG-Amine-9K was synthesized as follows. HPG-PEG-9K (1.0 g) was dissolved in 20 mL of pyridine. To this, p-toluene sulfonyl chloride (5.0 g) was added and stirred at room temperature for 24 hours. Pyridine was removed by rotary evaporation; the polymer was dissolved in 0.1 N HCl and dialyzed overnight. The polymer was isolated by freeze drying. HPG-PEG-Tos-9K (0.65 g; polymer from previous step) and tris(2-aminoethylamine) (3 mL) were dissolved in 1,4-dioxane (25 mL) and refluxed for 24 hours. Dioxane was removed under vacuum; the polymer was dissolved in minimum amount of methanol and precipitated twice from diethyl ether. Polymer was dissolved in water and dialyzed against water using MWCO-1000 membrane for 2 days.

The above polymer solution was added to a mixture of formaldehyde (3 mL) and formic acid (3 mL) at 0° C. The reaction mixture was refluxed overnight. After cooling to room temperature, the pH of the solution was adjusted to 10 using NaOH and the polymer was extracted with dichloromethane. Dichloromethane was removed under vacuum; the polymer dissolved in water and dialyzed using MWCO-1000 membrane for 3 days. The yield was 0.4 g and the amine content (by conductometric titration) was 16.35 mol %.

Example 8

Synthesis of JNK-10 Polymer

Firstly, a precursor polymer HPG-PEG-10K was synthesized as follows. A three-necked round bottomed flask was cooled under vacuum and filled with argon. To this, 1,1,1-Tris (hydroxymethyl)propane (TMP, 0.240 g) and potassium methylate (25 wt % solution in methanol, 0.220 mL) were added and stirred for 30 minutes. Methanol was removed under vacuum for 4 hours. The flask was heated to 95° C. and glycidol (2.5 mL) was added over a period of 15 hours. After complete addition of monomer, the reaction mixture was stirred for additional 3 hours. MPEG-epoxide-400 (9 mL)

was added over a period of 12 hours. The reaction mixture was stirred for additional 4 hours. The polymer was dissolved in methanol, passed through Amberlite IR-120H resin to remove the potassium ions and twice precipitated from diethyl ether. The polymer was fractional precipitated in methanol/ether mixture (1:10 v/v) to obtain HPG-PEG-10k polymer. The polymer was dissolved in water and dialyzed against water using MWCO-1000 membrane for 3 days with periodic changes in water.

Secondly, a precursor polymer HPG-PEG-Amine-10K was synthesized as follows. HPG-PEG-10K (2.4 g) was dissolved in 25 mL of pyridine. To this, p-toluene sulfonyl chloride (8.0 g) was added and stirred at room temperature for 24 hours. Pyridine was removed by rotary evaporation; the polymer was dissolved in 0.1N HCl and dialyzed overnight. The polymer was isolated by freeze drying. HPG-PEG-Tos-10K (2.8 g; polymer from the previous step) and tris(2-aminoethylamine) (8 mL) were dissolved in 1,4-dioxane (25 mL) and refluxed for 24 hours. Dioxane was removed under vacuum; the polymer was dissolved in minimum amount of methanol and precipitated twice from diethyl ether. Polymer was dissolved in water and dialyzed against water using MWCO-1000 membrane for 2 days.

The above polymer solution was added to a mixture of formaldehyde (6 mL) and formic acid (6 mL) at 0° C. The reaction mixture was refluxed overnight. After cooling to room temperature, the pH of the solution was adjusted to 10 using NaOH and the polymer was extracted with dichloromethane. Dichloromethane was removed under vacuum; the polymer dissolved in water and dialyzed using MWCO-1000 membrane for 3 days. The yield was 1 g and the amine content (by conductometric titration) was 20.9 mol %.

Example 9

Synthesis of JNK-11 Polymer

Firstly, a precursor polymer HPG-PEG-16K was synthesized as follows. A three-necked round bottomed flask was cooled under vacuum and filled with argon. To this, 1,1,1-Tris (hydroxymethyl)propane (TMP, 0.240 g) and potassium methylate (25 wt % solution in methanol, 0.220 mL) were added and stirred for 30 minutes. Methanol was removed under vacuum for 4 hours. The flask was heated to 95 C and glycidol (3 mL) was added over a period of 15 hours. After complete addition of monomer, the reaction mixture was stirred for additional 3 hours. MPEG-epoxide-400 (10 mL) was added over a period of 12 hours. The reaction mixture was stirred for additional 4 hours. The polymer was dissolved in methanol, passed through Amberlite IR-120H resin to remove the potassium ions and twice precipitated from diethyl ether. The polymer was fractional precipitated in methanol/ether mixture (1:5 v/v) to obtain HPG-PEG-16k polymer. The polymer was dissolved in water and dialyzed against water using MWCO-1000 membrane for 3 days with periodic changes in water.

Secondly, a precursor polymer HPG-PEG-Amine-16K was synthesized as follows. HPG-PEG-16K (1.7 g) was dissolved in 20 mL of pyridine. To this, p-toluene sulfonyl chloride (6.0 g) was added and stirred at room temperature for 24 hours. Pyridine was removed by rotary evaporation; the polymer was dissolved in 0.1 N HCl and dialyzed overnight. The polymer was isolated by freeze drying. HPG-PEG-Tos-16K (2 g; polymer from the previous step) and tris(2-aminoethylamine) (6 mL) were dissolved in 1,4-dioxane (25 mL) and refluxed for 24 hours. Dioxane was removed under vacuum; the polymer was dissolved in minimum amount of methanol and precipitated twice from diethyl ether. Polymer was dissolved in water and dialyzed against water using MWCO-1000 membrane for 2 days.

The above polymer solution was added to a mixture of formaldehyde (6 mL) and formic acid (6 mL) at 0° C. The reaction mixture was refluxed overnight. After cooling to room temperature, the pH of the solution was adjusted to 10 using NaOH and the polymer was extracted with dichloromethane. Dichloromethane was removed under vacuum; the polymer dissolved in water and dialyzed using MWCO-1000 membrane for 3 days. The yield was 1.3 g and the amine content (by conductometric titration) was 19.62 mol %.

Example 10

Binding Studies with Heparin and Heparin Derivatives

To demonstrate the utility and performance of HBSPCMs for neutralizing heparin, binding studies were performed with both unfractionated heparin (UFH) and low molecular weight heparin (LMWH) in in vitro human blood studies and in rats. HBSPCMs were also characterized for their ability to induce anticoagulation and clots in blood.

UFH and LMWHs are neutralized significantly more efficiently with the HBSPCMs than with protamine. Furthermore, HBSPCMs do not show any adverse effects on blood coagulation, platelet activity, complement activation, hemolysis and cytotoxicity while protamine and other cationic macromolecules do have adverse side effects.

Table 4 demonstrates a comparison of two embodiments of the polymer (JNK-1 and JNK-2) in terms of their ability to neutralize unfractionated heparin and low molecular weight heparin (LMWH), and shows a comparison with equivalent values for protamine. Both JNK-1 and JNK-2 result in greater neutralization of unfractionated heparin at two doses (50 and 100 μg/ml), Tinzaparin (LMWH) and Enoxaparin (LMWH).

TABLE 4

NEUTRALIZATION EFFECT OF JNK-1 AND JNK-2 POLYMERS

| Sample | Anti Xa Neutralization (%) of UFH at 100 μg/ml [1] | Anti Xa Neutralization (%) of Tinzaparin at 100 μg/ml [1] | Anti Xa Neutralization (%) of Enoxaparin at 100 μg/ml [1] | Anti Xa Neutralization (%) of UFH at 50 μg/ml [1] |
|---|---|---|---|---|
| JNK-1 | 89 ± 3 | 90 ± 2 | 81 ± 3 | 86 |
| JNK-2 | 90 ± 2 | 92 ± 4 | 89 ± 3 | 90 |
| Protamine | 85 ± 0 | 77 ± 1 | 73 ± 4 | 84 |

UFH = unfractionated heparin.
[1] One IU UFH or LMWH (Enoxaparin or Tinzaparin) per ml in platelet poor plasma.

Example 11

JNK-1 Neutralization of UFH

Figure 4A:
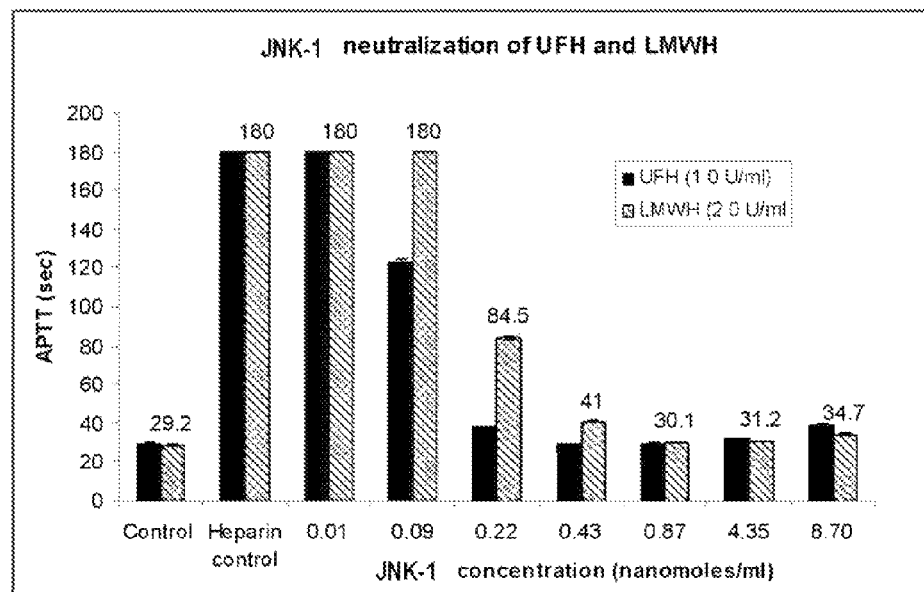
FIGS. 4A and 4B are graphs demonstrating heparin binding synthetic polyvalent cationic macromolecule JNK-1 neutralization of A) unfractionated heparin (UFH) B) LMWH (Tinzaparin) in human blood under in vitro conditions. Protamine neutralization is given as a comparison.
Figure 4B:
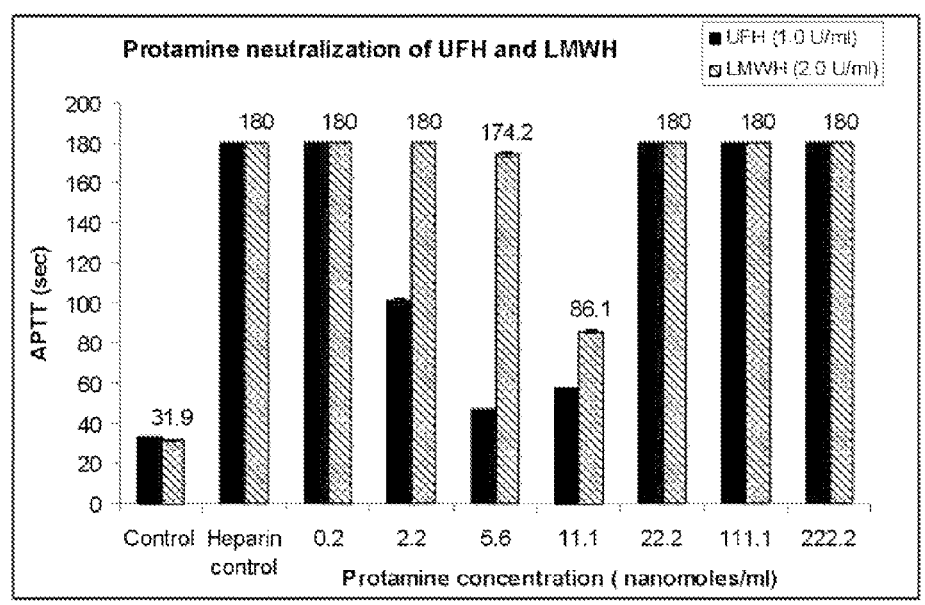

In one example, a heparin binding synthetic polyvalent cationic macromolecule JNK-1 can neutralize UFH in human blood under in vitro conditions (FIGS. 4A and 4B). Citrate plasma was anti-coagulated with 1.0 U/ml UFH (UFH control) and was titrated with different concentrations of JNK-1 polymers (0.009 to 8.69 nanomoles/ml) and protamine (0.2 to 222.2 nanomoles/ml). The activated partial thromboplastin time (APTT) was measured for each sample and is shown in FIGS. 4A and B. These results show that JNK-1 polymers effectively neutralized UFH (FIG. 4A) and do not cause anticoagulant effect even at high concentration, unlike protamine (FIG. 4B). JNK-1 polymers showed greater UFH neutralization capacity as compared to protamine.

Example 12

JNK-1 Neutralization of LMWH Tinzaparin

The present example demonstrates that JNK-1 polymers can neutralize LMWH Tinzaparin in human blood in vitro (FIGS. 4A and 4B). Citrate plasma was anti-coagulated with 2.0 U/ml LMWH (LMWH control) and was titrated with different concentrations of JNK-1 polymers (0.009 to 8.69 nanomoles/ml) (FIG. 4A) and protamine (0.2 to 222.2 nanomoles/ml) (FIG. 4B). The activated partial thromboplastin time (APTT) was measured for each sample, as shown in FIGS. 4A and 4B. Results show that JNK-1 effectively neutralizes Tinzaparin and does not cause any anticoagulant effect at even higher concentration, unlike protamine. Unlike protamine, JNK-1 polymers completely neutralized the anticoagulation of LMWH and showed greater efficiency.

Example 13

Percentage of UFH and LMWH Tinzparin Neutralization

Figure 5:
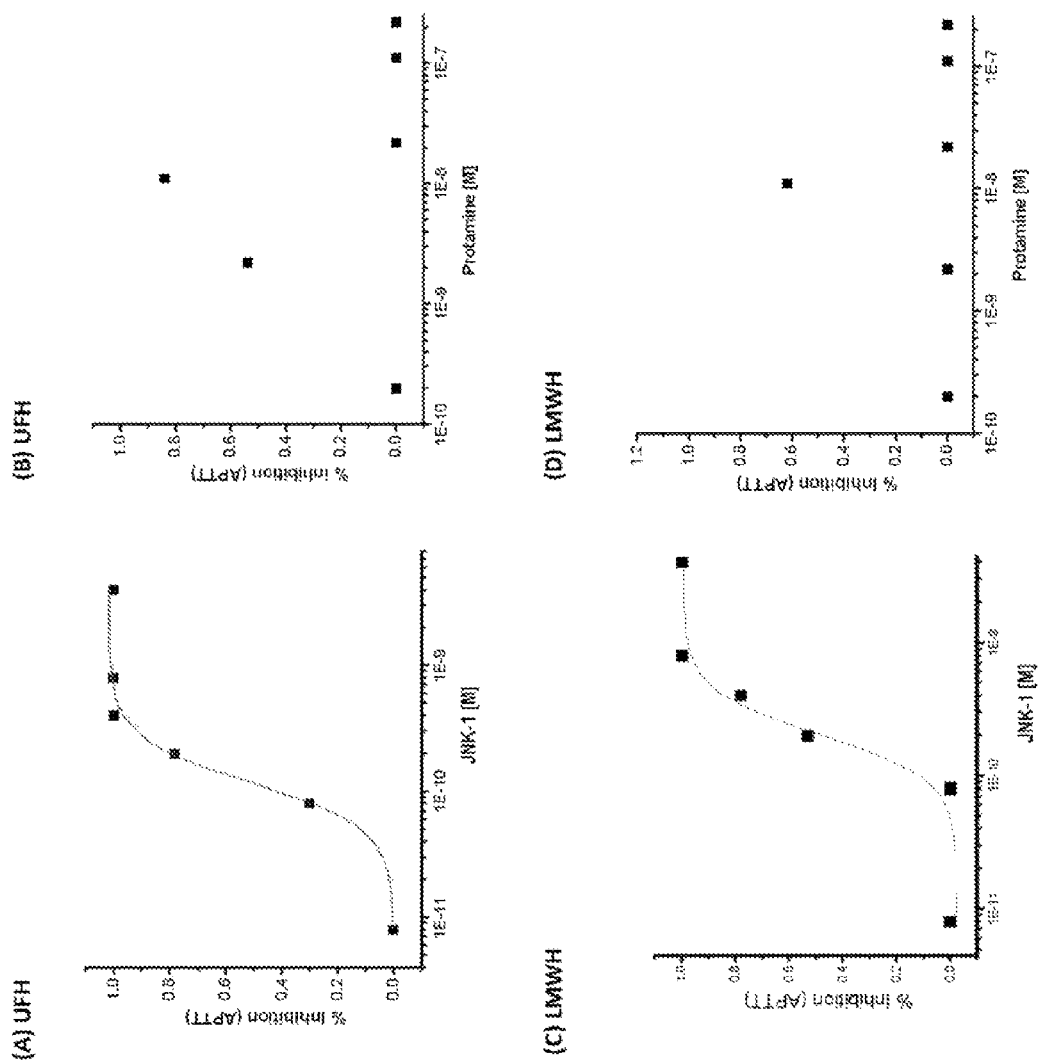
FIGS. 5A-5D are graphs depicting the percentage of unfractionated heparin (UFH) and low molecular weight heparin (LMWH) neutralization calculated from an activated partial thromboplastin time (APTT) assay by heparin binding synthetic polyvalent cationic macromolecule JNK-1 and protamine.

The present example demonstrates the percentage of UFH and LMWH Tinzparin neutralization calculated from an activated partial thromboplastin time (APTT) assay by JNK-1 or protamine. FIG. 5A shows the JNK-1 polymer neutralization of UFH. FIG. 5B shows the protamine neutralization of UFH. FIG. 5C shows the JNK-1 polymer neutralization of LMWH. FIG. 5D shows the protamine neutralization of LMWH. The $IC_{50}$ of UFH neutralization by JNK-1 polymers is 0.1 nanomoles and of Tinzaparin is 0.2 nanomoles, which is a few orders lower (more efficient) than protamine. JNK-1 completely neutralizes UFH and Tinzaparin.

Example 14

Thromboelastography in the Presence of Various Heparin Binders

This example examines thromboelastography in the presence of various heparin binders. Thromboelastography (TEG) provides an in vitro method for monitoring of the evolution of the viscoelastic properties and coagulation kinetics of blood as clotting proceeds. The principle components of the TEG are a cylindrical cup and a bob suspended in the cup from a weak torsion wire. The warmed cup oscillates over a 10 second period through an angle of 4° 45'. Blood is added and a torque is transmitted to the bob as the gel forms. The rate of clot formation, the strength of the clot, and the rate of clot lysis are reflected in the shape traced out by the maxima in the bob oscillation as a function of time (the trace of the TEG). The clot's physical properties, i.e. rate of clot formation, clot strength, and stability are dependent on the interaction of fibrinogen, platelets, and plasma proteins. TEG studies yield the cumulative effect of several components of coagulation (global homeostasis) as a function of time.

To carry out TEG experiments, citrate anti-coagulated whole blood with heparin or heparin derivatives added are incubated with buffered HBSPCM polymers (sodium citrate or saline) for 1 minute before recalcification at 37° C. Clot formation kinetics are monitored in a TEG machine (350 µl whole blood+35 µl polymer or control solution) at 37° C.

Figure 6:
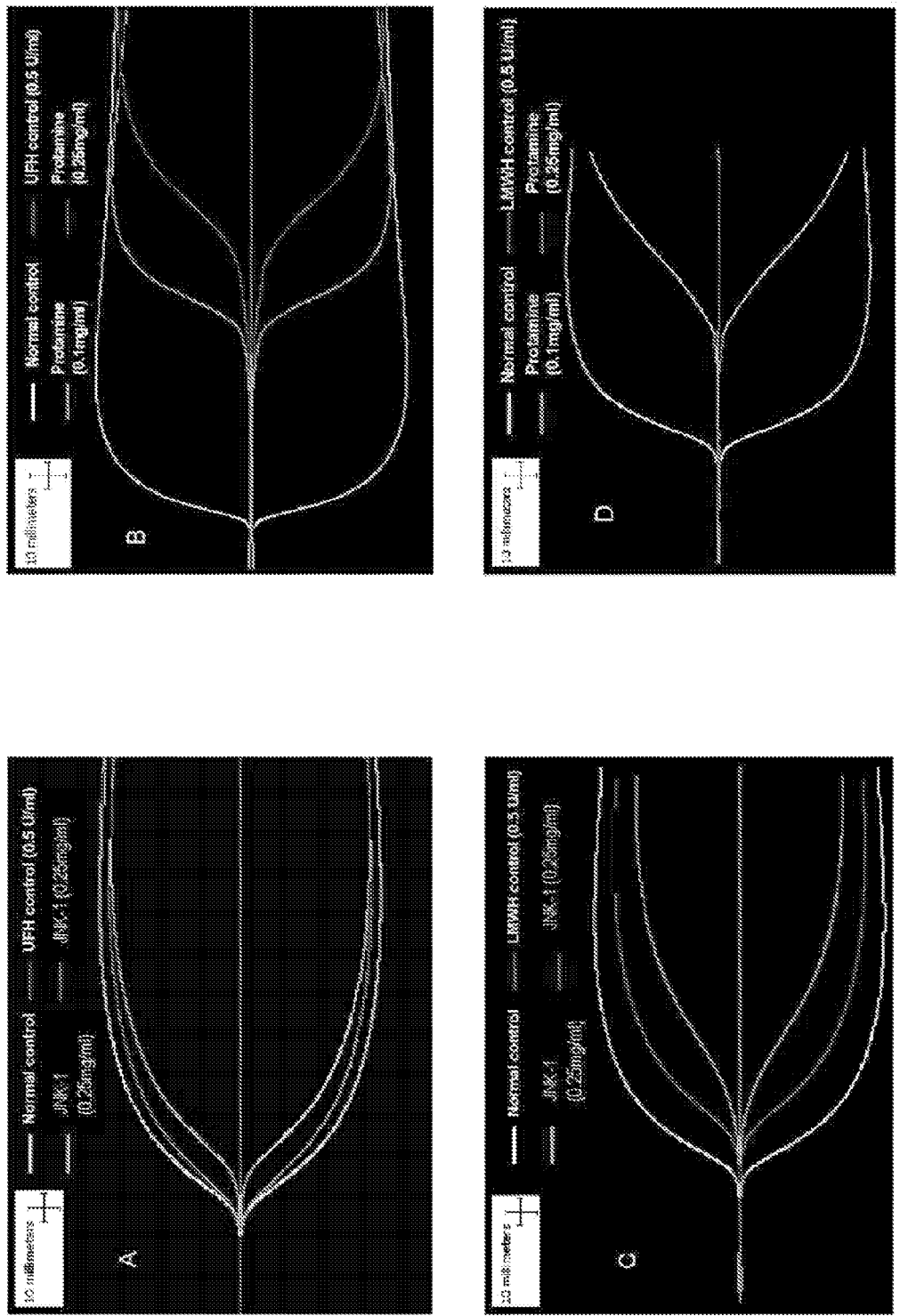
FIGS. 6A-6D are graphs depicting heparin binding synthetic polyvalent cationic macromolecule JNK-1 neutralization of unfractionated heparin (UFH) and low molecular weight heparin (LMWH) Tinzaparin using a thromboelastograph (TEG) as measured by a thromboelastograph in human whole blood.

JNK-1 polymers can neutralize UFH and LMWH Tinzaparin, as demonstrated by using a TEG measurement of human whole blood (FIG. 6). TEG traces of different experiments are given. JNK-1 polymer neutralization of UFH is shown in FIG. 6A. Protamine neutralization of UFH is shown in FIG. 6B. JNK-1 polymer neutralization of Tinzaparin is shown in FIG. 6C. Protamine neutralization of Tinzaparin is shown in FIG. 6D. The results demonstrate the ability of JNK-1 to neutralize UFH and Tinzaparin even at higher concentration, unlike protamine. There was no clot formation observed in presence of either UFH or Tinzaparin alone.

Example 15

JNK-1 Polymers can Neutralize UFH and LMWH Tinzaparin

Figure 7A:
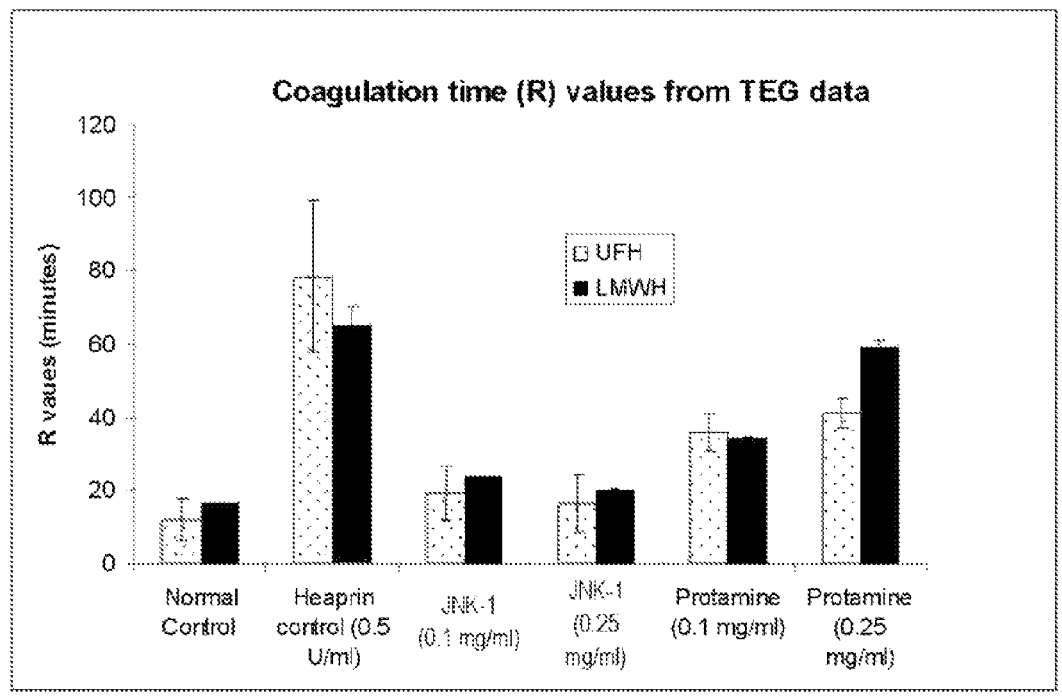
FIGS. 7A-7B are graphs depicting heparin binding synthetic polyvalent cationic macromolecule JNK-1 neutralization of unfractionated heparin (UFH) and low molecular weight heparin (LMWH) Tinzaparin using thromboelastograph (TEG) in terms of coagulation time and clot strength in human whole blood.
Figure 7B:
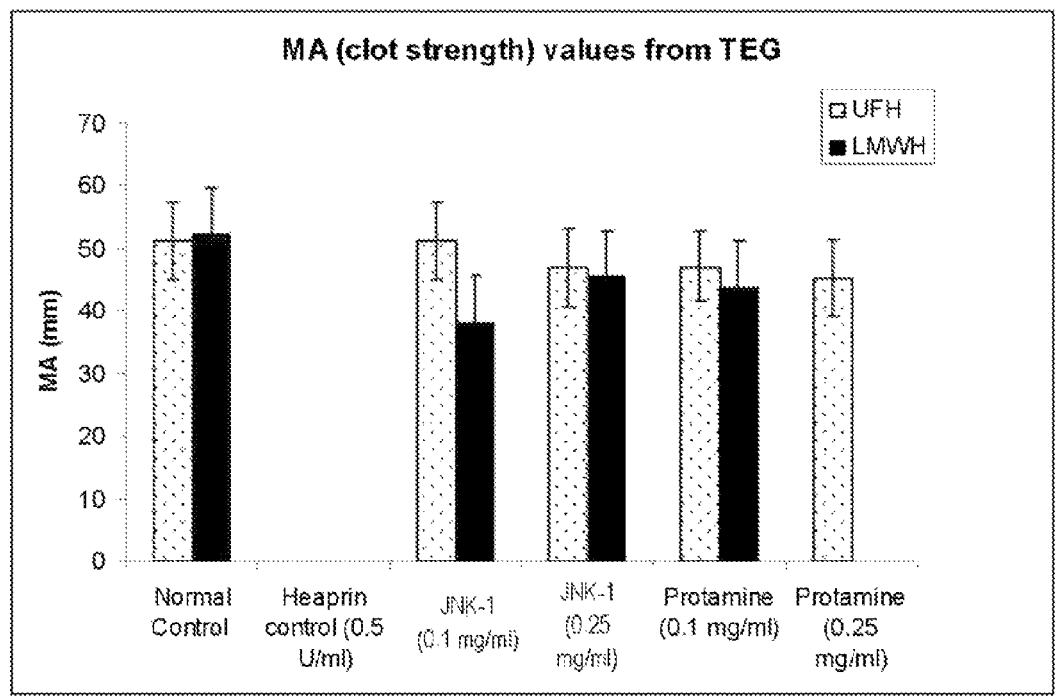

The present example demonstrates that JNK-1 polymers can neutralize UFH and LMWH Tinzaparin, as demonstrated by using a TEG measurement of human whole blood (FIGS. 7A and 7B). The coagulation time (FIG. 7A) and maximum clot strength, or maximum amplitude (MA) (FIG. 7B) are shown. Citrated whole blood was added to UFH or Tinzaparin (0.5 U/ml) and re-calcified at 37° C. in a TEG cup and monitored using a TEG machine. JNK-1 polymers or protamine at different concentrations were used as neutralizing agents.

The results demonstrate that JNK-1 polymers effectively neutralize anticoagulation effect of both UFH and Tinzaparin. Protamine at a higher concentration (0.25 mg/ml) did not form a stable clot (see maximum amplitude (MA) data) with Tinzaparin. There was no clot formation observed in presence of either UFH or Tinzaparin alone.

Example 16

Figure 9:
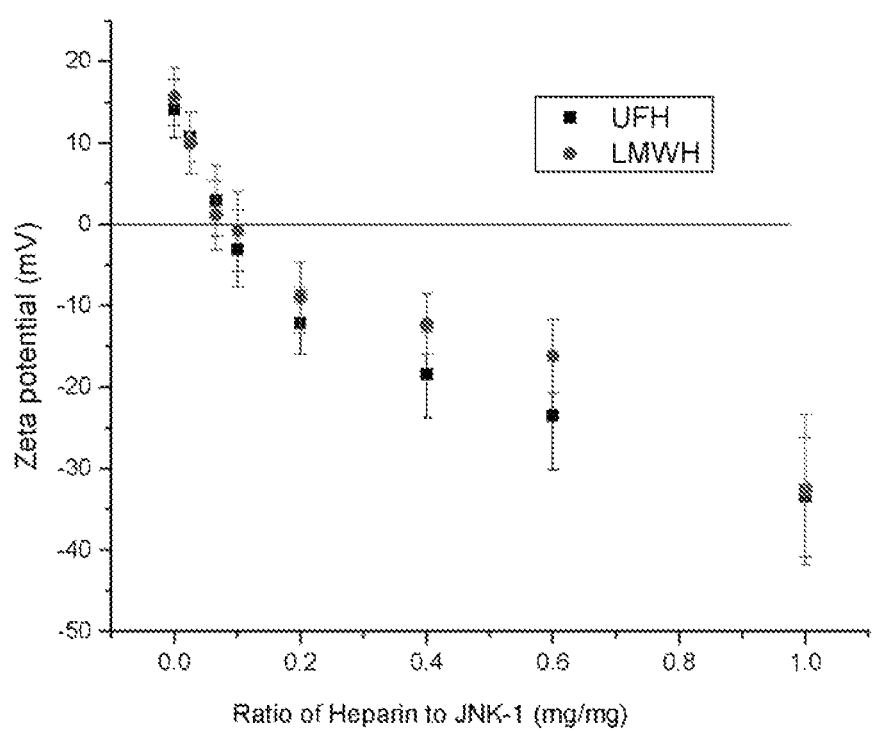
FIG. 9 is a graph depicting electrostatic charge neutralization of unfractionated heparin (UFH) and low molecular weight heparin (LMWH) by heparin binding synthetic polyvalent cationic macromolecule JNK-1.

Electrostatic Charge Neutralization of UFH and LMWH Tinzaparin by JNK-1 Polymers This example demonstrates the electrostatic charge neutralization of UFH and LMWH Tinzaparin by JNK-1 polymers (results shown in FIG. 9). The electrophoretic mobilities of heparin/JNK-1 complexes formed by mixing the different ratios of heparin and JNK-1 polymers were measured. JNK-1 polymers neutralize UFH and Tinzaparin at similar concentrations. The results are presented in FIG. 9.

Example 17

Complement Activation

The present example examines complement activation due to heparin binding polymers. Complement activation is one of the major adverse side effects associated with the clinical use of protamine in the reversal of anticoagulation in cardiopulmonary bypass and other surgical conditions (Shastri et al. 1997 Cardiovasc Surg. 114(3):482-8). Complement activation induced by various biomaterials has been studied (Lamba et al 1999. Biomaterials 21:89; Kidane et al 1999. J Biomed Mate Res 48:640; Lim et al 1993. Biomaterials 14:537; Payne et al 1987. J Biomed Mater Res 21:843; Jantova et al 1991. Complement and Inflammation 8:61). Examples of polymers which cause complement activation include dextran, regenerated cellulose, sephadex, nylon, poly(methylmethacrylate), poly(propylene), poly(acrylamide), poly(hydroxyethylmethacrylate), plasticised PVC. Complement activation is not a property of all polymers however. For example, poly(N-vinylpyrrolidone) does not cause complement activation (Beillat et al 1984. ASAIO J 7:57).

To assess complement activation, the activation of the complement component C3 was monitored by measuring the formation of its activation peptides using a commercial C3a enzyme immunoassay kit (Quidel, San Diego, Calif.), following manufacturer's instructions. The C3a concentrations (in ng/ml) were calculated using a standard curve with net absorbance values plotted on the y-axis for each C3a concentration indicated on the x-axis.

Figure 10A:
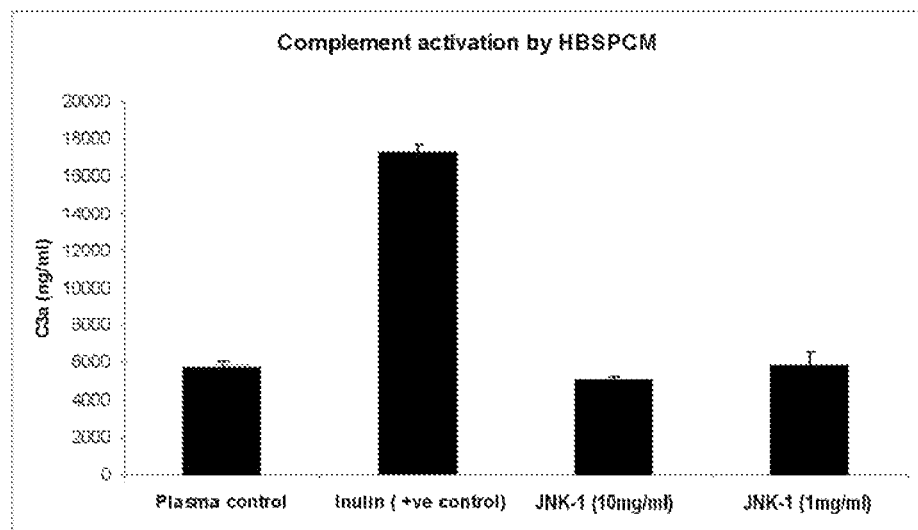
FIG. 10A is a bar graph depicting complement activation upon interaction of heparin binding synthetic polyvalent cationic macromolecule JNK-1 with platelet poor plasma.

Complement activation upon interaction of JNK-1 polymers with platelet poor plasma (10 mg/ml and 1 mg/ml) is shown in FIG. 10A at 37° C. for 1 hour at 9:1 dilution of platelet poor plasma. Plasma incubated with saline as a control and insulin (a potent complement activator) as positive control are also given. Results show that JNK-1 polymers do not initiate complement activation.

Figure 20:
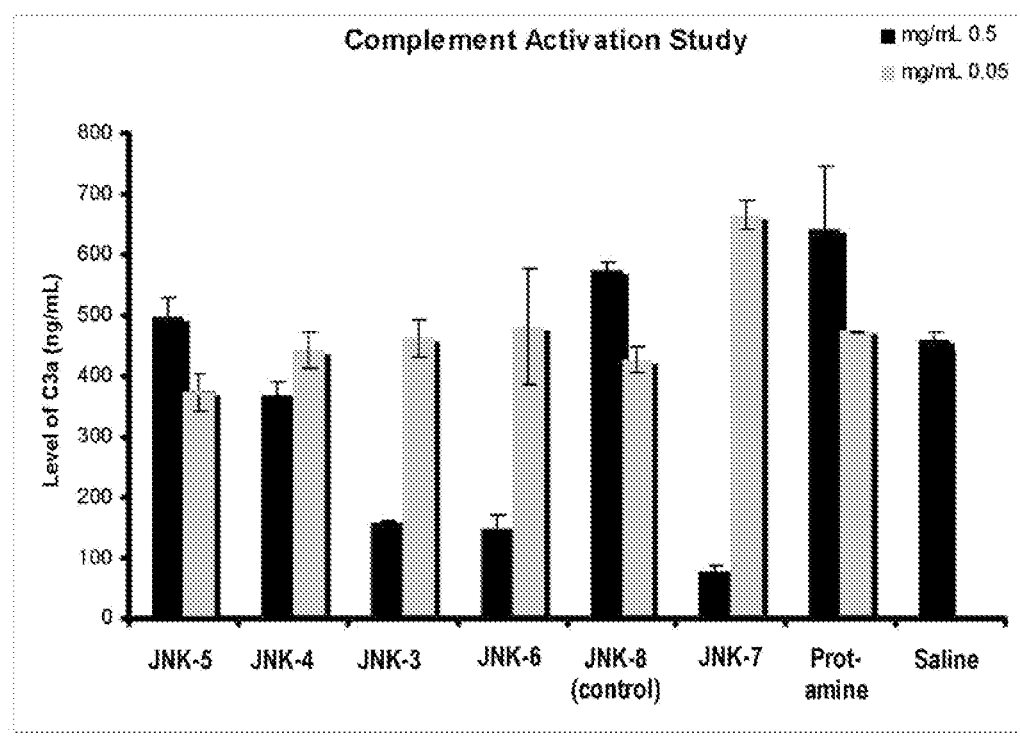
FIG. 20 is a bar chart depicting complement activation by the HBSPCM polymers JNK-3 to JNK-8 in comparison to protamine and saline.

FIG. 20 demonstrates the complement activation by the HBSPCM polymers described in Table 2 (JNK-3, JNK-4, JNK-5, JNK-6, JNK-7 and JNK-8-control) in comparison to protamine and a saline control. Complement activation is shown upon interaction of the HBSPCM polymers in platelet poor plasma (PPP) at 37° C. for 1 hour at a 9:1 dilution of PPP. At 0.5 mg/mL, the HBSPCM polymers all had reduced complement activation as compared to protamine. At 0.05 mg/mL, all but one HBSPCM polymer (JNK-7) had reduced complement activation as compared to protamine and similar activation to saline.

Example 18

Platelet Activation

The present example examines platelet activation in the presence of heparin binding polymers. Platelet activation leads to aggregation, which can cause adverse effects such as thrombotic complications or arterial embolization. To measure platelet activation, blood was collected in sodium citrate anticoagulant and the platelet rich plasma (PRP) isolated by centrifugation. Plasma was then incubated at 37° C. with JNK-1 at 10 mg/mL (9:1 dilution), polyethyleneimine (PEI) at 1 mg/ml, insulin (a potent complement activator) as a positive control, saline, or PRP incubated with adenosine diphosphate and thrombin as a positive control for 30 minutes. Aliquots of the incubation were assessed for activation state of the platelets using fluorescence flow cytometry. Expression of the platelet activation marker CD62P was detected using a Coulter Epics-XL (Miami, Fla.). Briefly, the post-incubation polymer/platelet mix was diluted and incubated with the monoclonal anti-CD 62P-FITC antibody. Data is reported as the percentage of platelets positive (activated) for CD62.

Figure 10B:
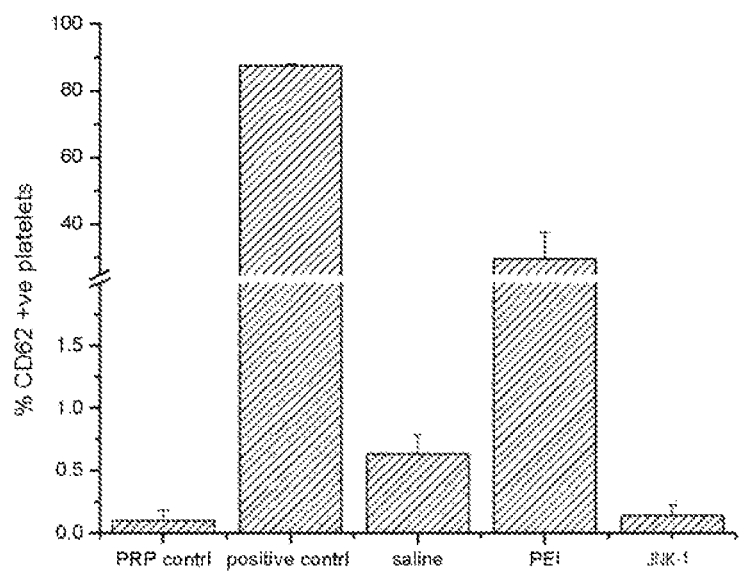
FIG. 10B is a bar graph depicting platelet activation upon interaction of JNK-1 with platelet rich plasma at 37 C.

FIG. 10B demonstrates the platelet activation upon interaction with JNK-1 polymers and controls. Results show that JNK-1 does not induce platelet activation as compared to known activators (PEI and positive control). JNK-1 polymers induced activation that was no greater than that seen with saline alone; thus, the low level CD62 expression seen for JNK-1 polymers can be attributed to the choice of suspending medium for the polymer.

Example 19

Blood Coagulation

The present example examines blood coagulation in the presence of a heparin binding polymer. JNK-1 polymers were tested for blood compatibility using the activated partial thromboplastin time (APTT) and the prothrombin time (PT) in fresh human plasma. PT can be used to evaluate the extrinsic and common coagulation pathway and the results are expressed in seconds required for a fibrin clot to form after tissue thromboplastin (innovin) has been added to the blood sample. APTT is used to evaluate the intrinsic and common coagulation pathway. The results are expressed in seconds required for a fibrin clot to form in the plasma sample after a partial thromboplastin reagent (actin) and calcium chloride have been added to the sample. Blood was mixed with a measured amount of citrate and the plasma was obtained by centrifugation, using methods known in the art.

Figure 11A:
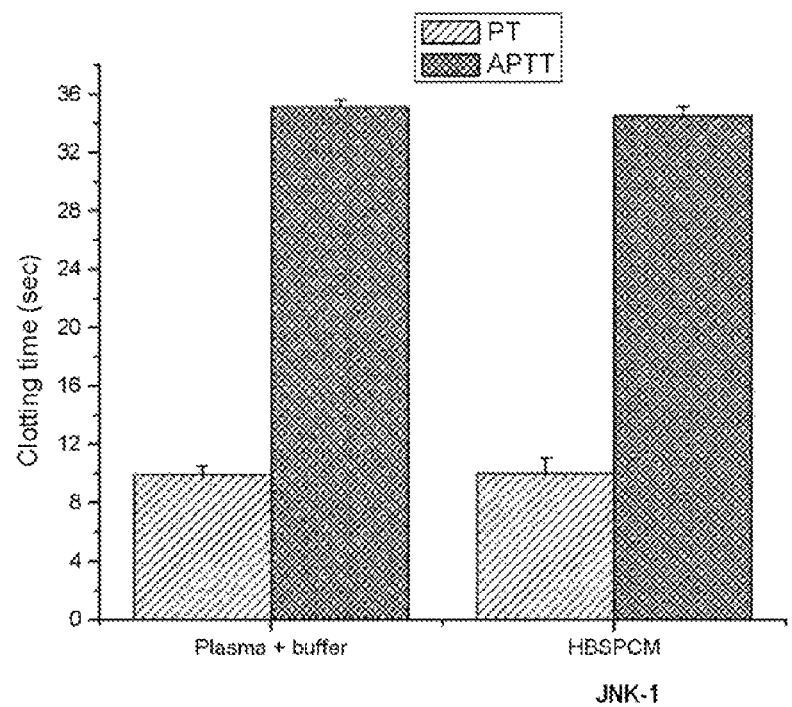
FIG. 11A and FIG. 11B are bar graphs depicting the effect of heparin binding synthetic polyvalent cationic macromolecule JNK-1 on prothrombin time (PT) and activated partial thromboplastin time (APTT) in platelet poor plasma (PPP).

The effect of JNK-1 polymers on PT and APTT in platelet poor plasma is shown in FIG. 11A. A final JNK-1 concentration of 10 mg/ml is used at in a 9:1 dilution of plasma at 37° C. Control experiments were done adding identical volumes of saline solution. JNK-1 polymer solutions were incubated with platelet poor plasma for 5 minutes at 37° C. before adding PT and APTT reagents. The results show that JNK-1 polymers do not influence blood coagulation on their own as there was no significant difference between the JNK-1 polymers and the saline control.

Figure 11B:
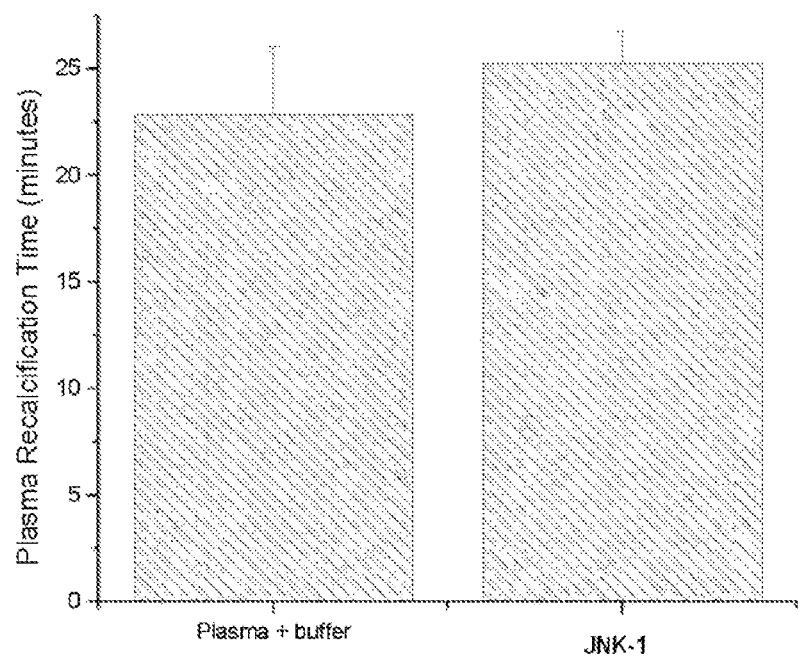

Plasma re-calcification time can be calculated as the time it takes to detect a clot after the addition of calcium ions. FIG. 11B shows the effect of JNK-1 polymers on plasma re-calcification time in platelet poor plasma. A final JNK-1 polymer concentration of 10 mg/ml was used in a 9:1 dilution of plasma at 37° C. Control experiments were done adding identical volumes of saline solution. In this experiment no additional agent is added to induce the coagulation except the calcium chloride solution (recalcification). There was no significant difference between the JNK-1 and plasma control. The results show that JNK-1 polymers do not influence the coagulation on their own.

Figure 12:
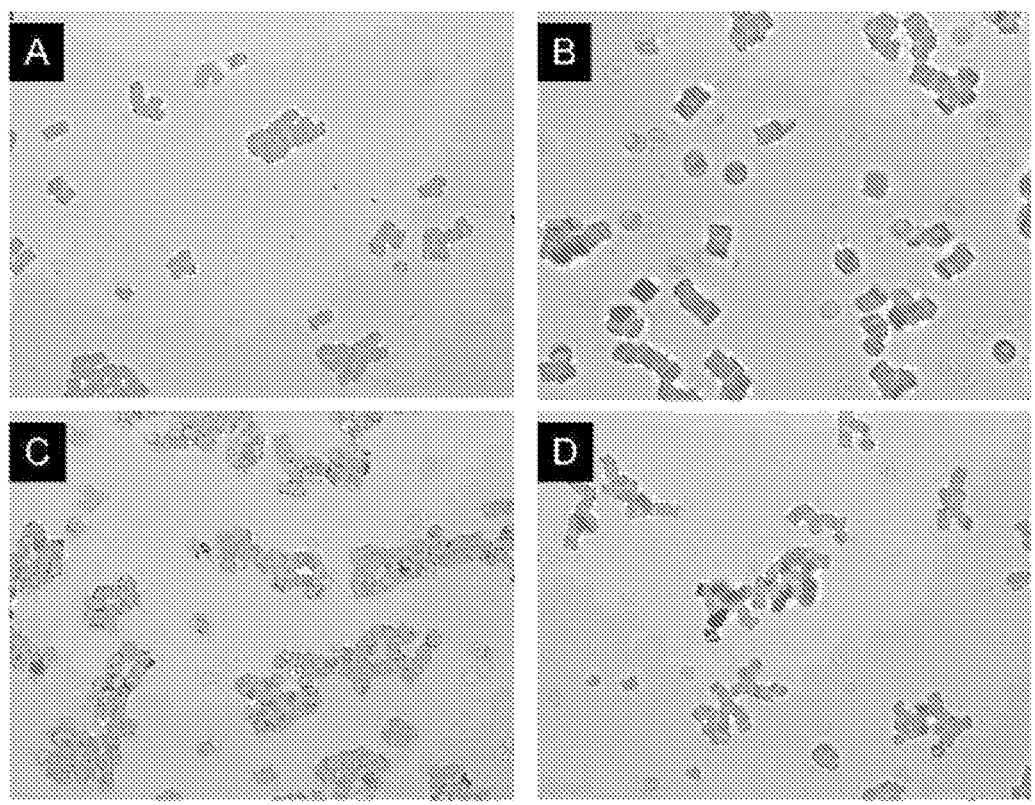
FIGS. 12A-12D depict optical micrographs of human red blood cells after 1 hour incubation with heparin binding synthetic polyvalent cationic macromolecule JNK-1 at different concentrations in whole blood at 37° C.

Optical micrographs are shown in FIGS. 12A-12D of human red blood cells after one-hour incubation with JNK-1 polymers at different concentrations in whole blood (9:1 dilution) at 37° C. All images are at 400× magnification. FIG. 12A is an incubation of JNK-1 polymers (10 mg/ml). FIG. 12B is an incubation of JNK-1 polymers (1 mg/ml). FIG. 12C is an incubation of polyethyleneimine (PEI) (1 mg/ml). FIG. 12D is an incubation of saline control. Results show that JNK-1 polymers do not induce adverse effects such as red cell aggregation or hemolysis, unlike cationic polymers such as PEI (FIG. 12C).

Example 20

Heparin and Heparin Derivative Neutralization in Human Blood

Human plasma treated with sodium citrate was anti-coagulated with unfractionated heparin (UFH) or low molecular weight (LMWH) Tinzaparin. Samples subsequently mixed with JNK-1 and JNK-2 polymers showed complete neutralization for both UFH and Tinzaparin and did not show anticoagulation at high doses.

Conversely, for protamine treated samples, complete neutralization occurred at a higher dosage of protamine for UFH and not at all for Tinzaparin. Furthermore, at high doses protamine had an anticoagulant effect and was not an effective antidote.

These results were confirmed by analysis of the activated partial thromboplastin time (APTT), which showed that JNK-1 polymers were capable of complete neutralization of UFH and LMWH but that protamine was incapable of neutralizing LMWH and acted with less efficiency for UFH within a smaller dose window. Overall, JNK-1 polymers showed greater UFH and LMWH neutralization capacity as compared to protamine in citrated plasma.

JNK-1 and JNK-2 polymers were also tested with human whole blood for efficacy in neutralizing UFH and LMWH. Thromboelastography measurements showed that human whole blood containing UFH or LMWH was efficiently neutralized by the polymers JNK-1 and JNK-2. Conversely, protamine was not effective at neutralizing UFH or LMWH Tinzaparin and Enoxaparin in terms of the time to clot formation in human whole blood. Although protamine was able to allow UFH treated blood to regain the same clot strength, it only capable of enabling LMWH Tinzaparin treated blood to regain the same clot strength at a lower dose and not at all at a high dose.

This study in human citrated plasma and whole blood indicates that the JNK-1 and JNK-2 polymers are effective for human samples with UFH and LMWH. Furthermore, these studies provide evidence that JNK-1 and JNK-2 polymers display properties that are consistent with being useful for human clinical use.

Figure 18A:
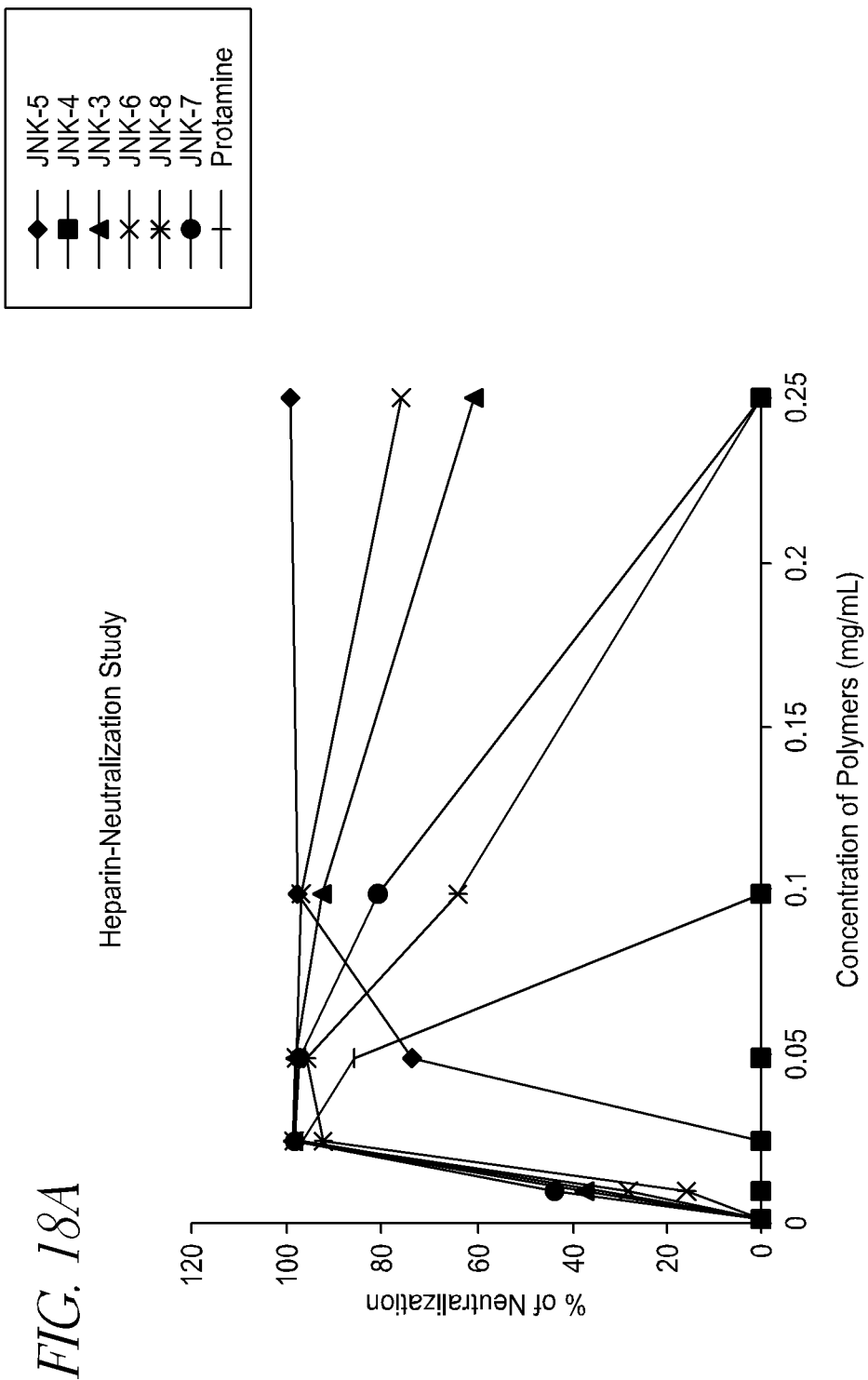
FIGS. 18A-18C are graphs depicting the neutralization of unfractionated heparin (FIG. 18A), Tinzaparin (FIG. 18B) and Enoxaparin (FIG. 18C) by HBSPCM polymers JNK-1 through JNK-8 as compared to protamine in human blood in vitro.
Figure 18B:
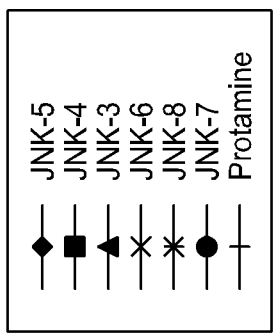
Figure 18B:
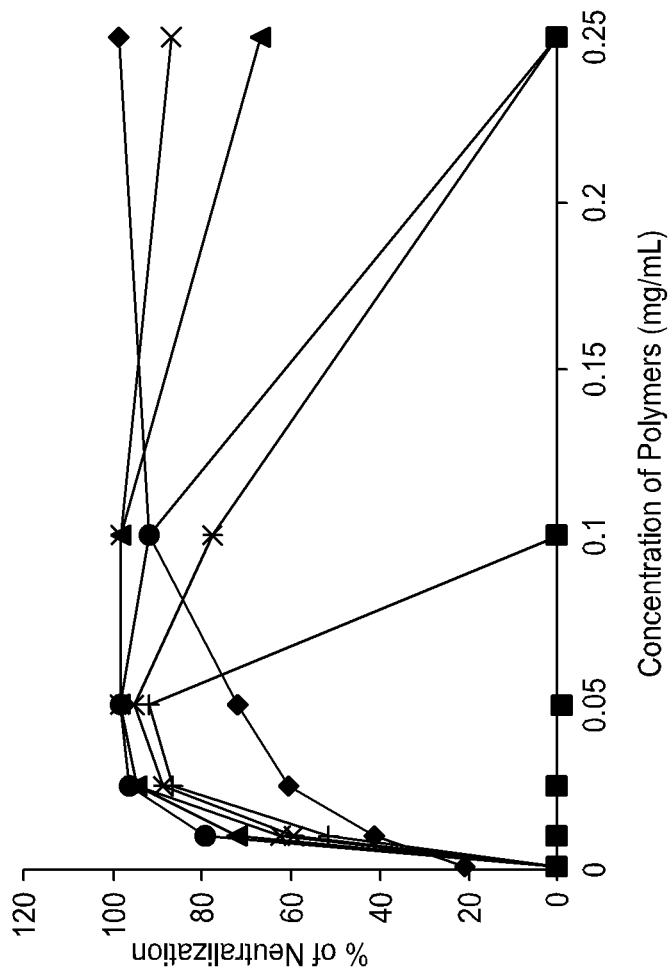
Figure 18C:
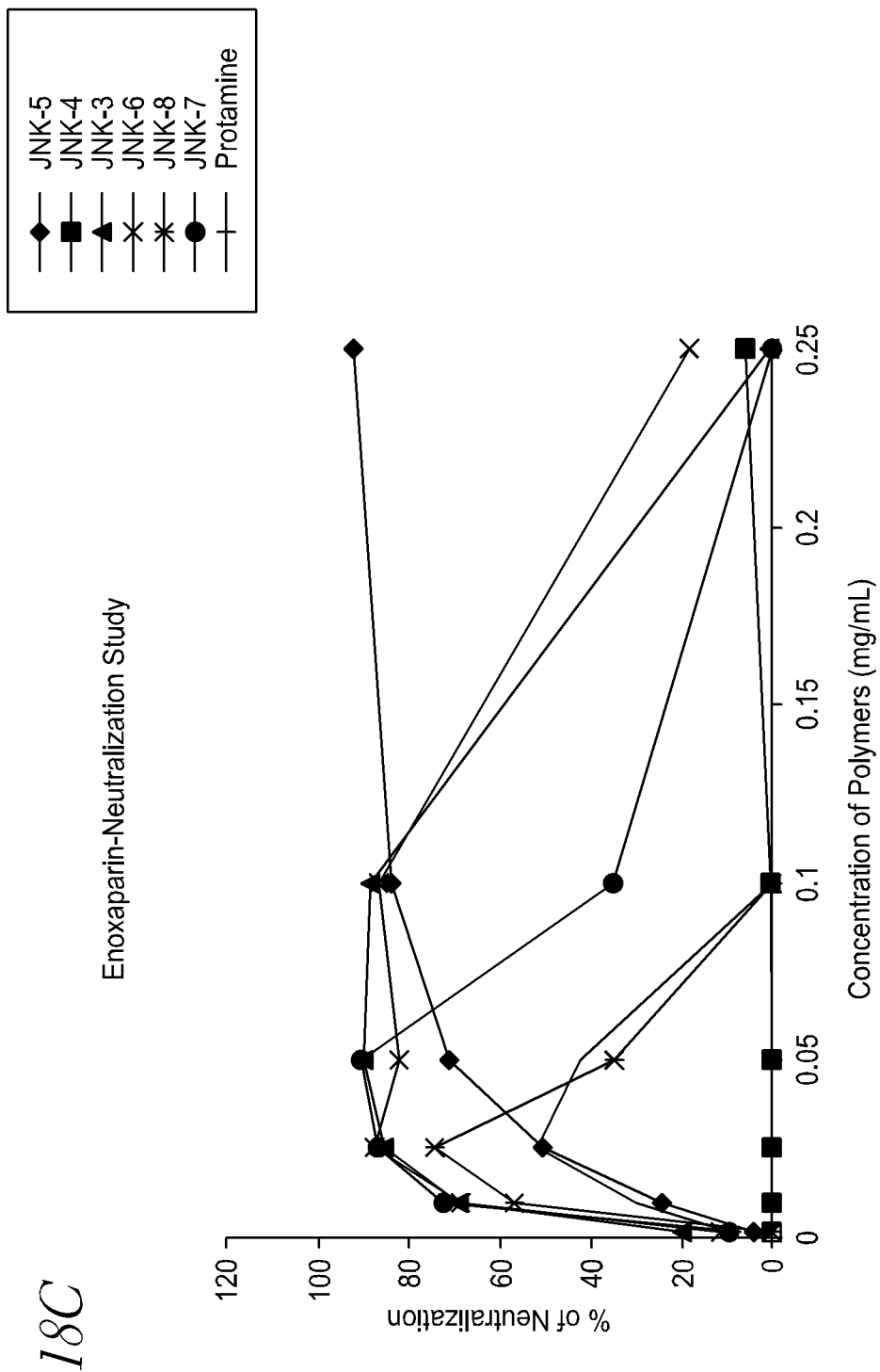

The results in FIGS. 18A-18C demonstrate the neutralization of different heparins: FIG. 18A: unfractionated heparin (UFH); FIG. 18B: LMWH Tinzaparin; and FIG. 18C: LMWH Enoxaparin by the HBSPCM polymers described in Table 2 (JNK-3 to JNK-8) in comparison to protamine in human blood in vitro.

Citrate plasma was anticoagulated with 2.0 U/ml UFH, Enoxaparin and Tinzaparin and was treated with different concentrations of the HBSPCM polymers and protamine (0.001 to 0.25 mg/ml). The APTT was measured for each sample. Results show that the HBSPCM polymers, unlike protamine, effectively neutralize UFH and LMWH (Tinzaparin and Enoxaparin) and do not cause any anticoagulant effect at even higher concentration. HBSPCM polymers can almost completely neutralize the anticoagulation of LMWH (Tinzaparin and Enoxaparin) at certain doses and showed greater efficiency.

Figure 19:
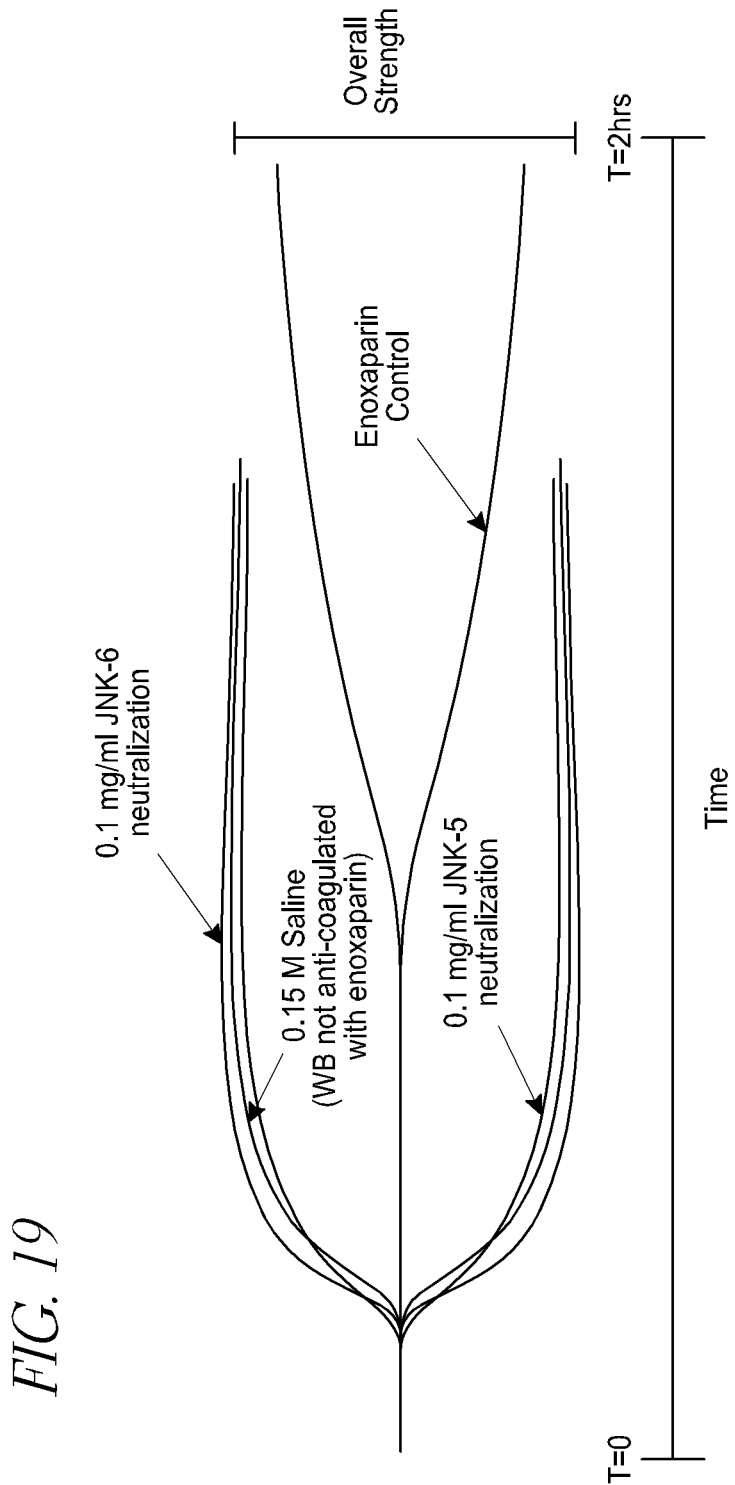
FIG. 19 is a graph depicting the neutralization of low molecular weight heparin using a thromboelastograph (TEG) in human whole blood by HBSCPM polymers JNK-5 and JNK-6.

The results in FIG. 19 also demonstrate that HBSPCM polymers can effectively neutralize LMWH using a thromboelastograph (TEG) in human whole blood. HBSCPM polymers JNK-5 and JNK-6 (0.1 mg/ml) were added to the anticoagulated blood and compared to a control with no Enoxaparin added (no anti-coagulation with Enoxaparin) and no neutralization (Enoxaparin control). The results demonstrate the ability of JNK-5 and JNK-6 to neutralize. Enoxaparin in terms of the TEG strength. The TEG trace of the enoxaparin neutralized blood is almost identical to saline control, which was not coagulated. Together with FIG. 18, these data demonstrate the efficiency of HBSPCM polymers such as JNK-5 and JNK-6 to neutralize LMWH under in vitro conditions.

Figure 24A:
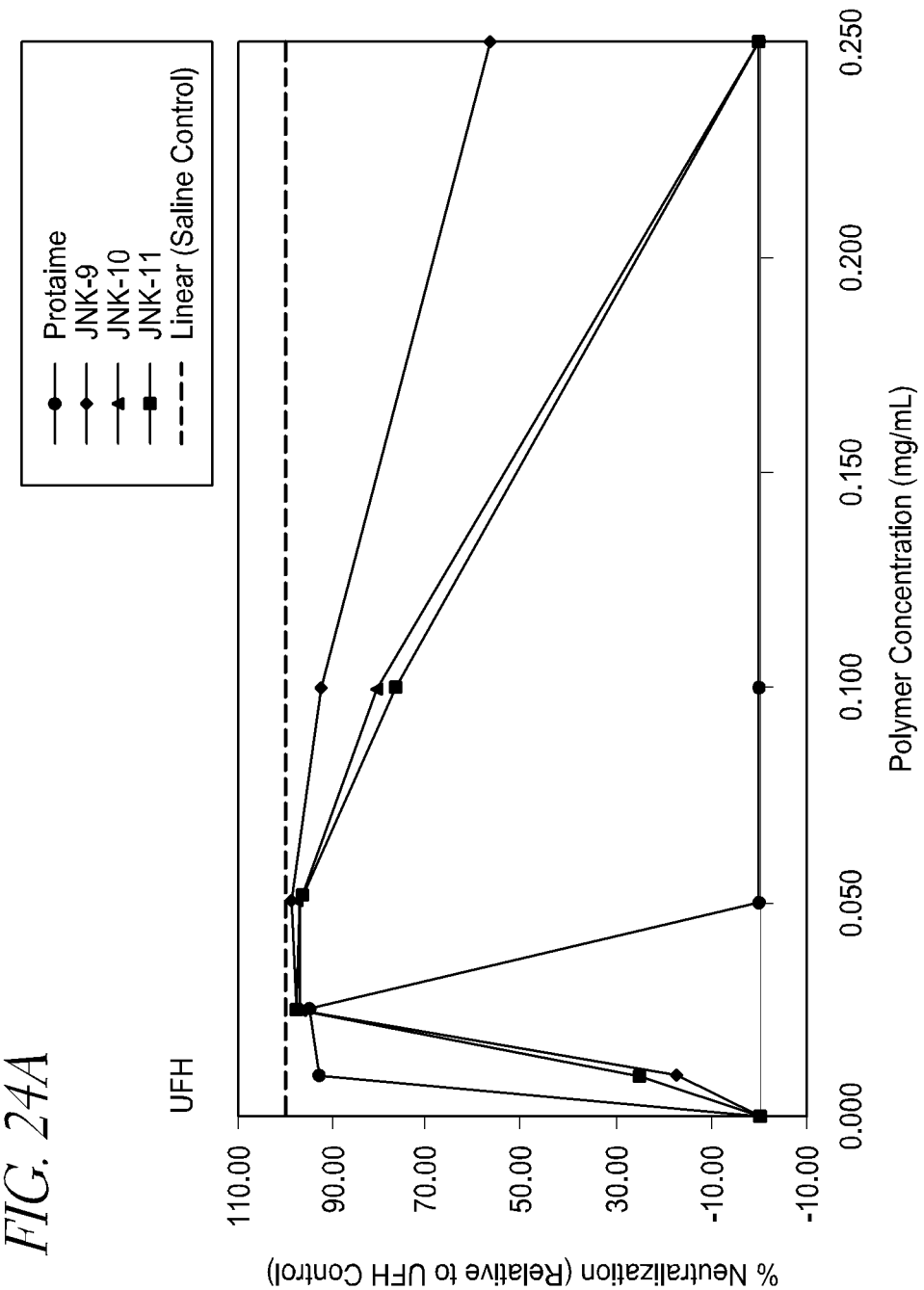
FIGS. 24A-24C are graphs depicting neutralization of unfractionated heparin (UFH) (FIG. 24A), Tinzaparin (FIG. 24B) and Enoxaparin (FIG. 24C) by HBSPCM polymers JNK-9, JNK-10 and JNK-11 as compared to protamine in human plasma in vitro.
Figure 24B:
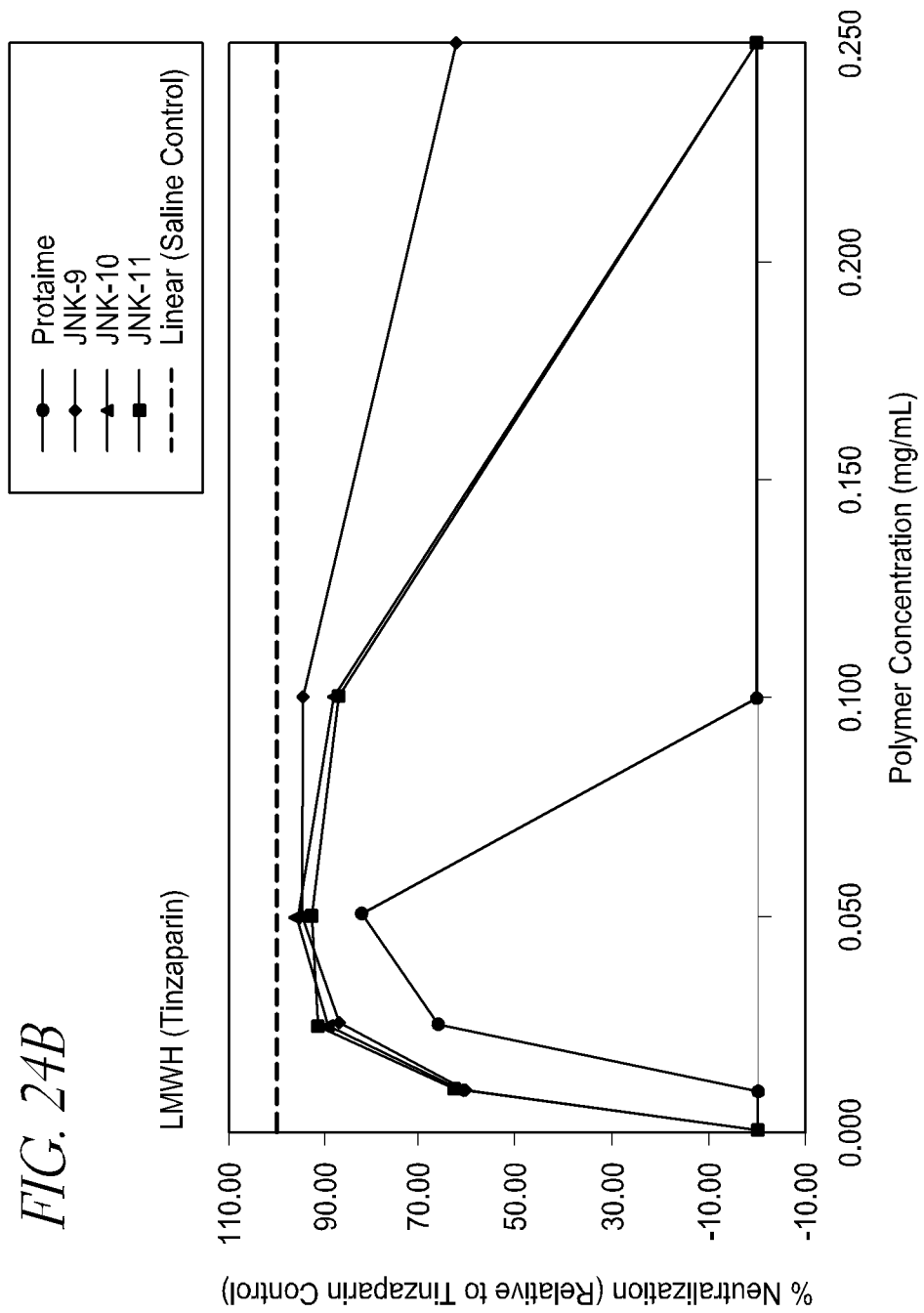
Figure 24C:
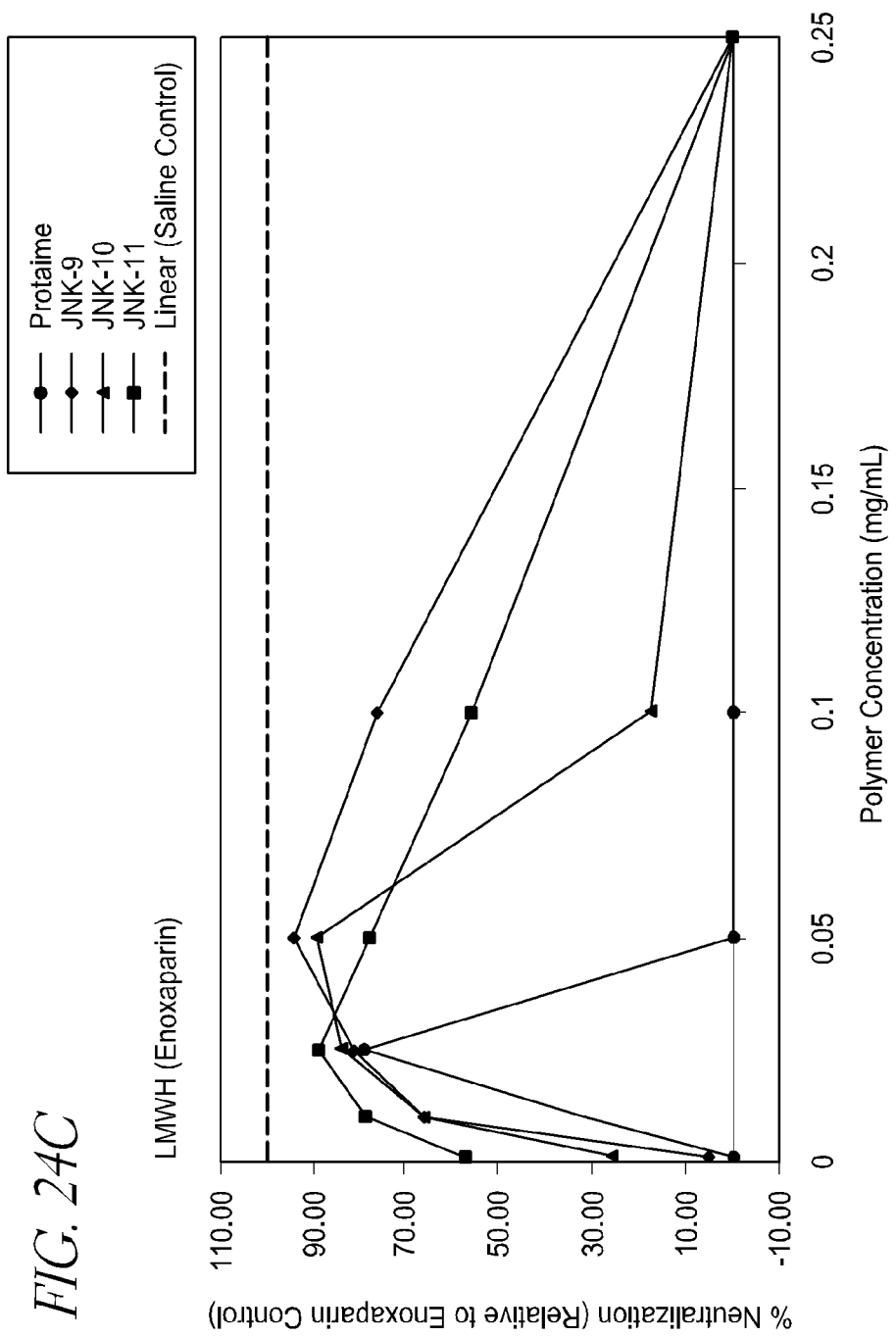

The data in FIGS. 24A-24C demonstrate the neutralization of different heparins ((FIG. 24A): unfractionated heparin (UFH); (FIG. 24B): LMWH Tinzaparin; and (FIG. 24C): LMWH Enoxaparin) by the HBSPCM polymers described in Table 3 (JNK-9, JNK-10, JNK-11) in comparison to protamine in human plasma in vitro. Citrate plasma was anticoagulated with UFH (2.0 IU/mL), Enoxaparin (2.0 IU/mL) and Tinzaparin (1.14 IU/mL) and was titrated with different concentrations of the HBSPCM polymers and protamine (0.001 to 0.25 mg/ml). The APTT was measured for each sample. Results show that the HBSPCM polymers, unlike protamine, effectively neutralize UFH and LMWH (Tinzaparin and Enoxaparin) and do not cause any anticoagulant effect at higher concentrations than protamine. The HBSPCM polymers JNK-9, JNK-10 and JNK-11 can almost completely neutralize the anticoagulation of LMWH (Tinzaparin and Enoxaparin) at certain doses and showed greater efficiency.

Example 21

High Binding Affinity of Heparin to HBSPCM Polymer JNK-2

The present example examines the binding affinity of a heparin binding polymer to heparin. The HBSPCM polymer JNK-2 was tested for UFH, LWMH and fondaprinux binding by isothermal titration calorimetry. Isothermal titration calorimetry (ITC) was performed using a VP-ITC (MicroCal, Inc., Northampton Mass.). Samples were in PBS buffer pH 7.2. Titrations were performed by injecting consecutive 5-10 µl aliquots of JNK-2 solution into the ITC cell (volume=1.4 mL) containing heparin or heparin derivatives. The ITC data were corrected for the heat of dilution of the titrant by subtracting mixing enthalpies for 5-10 µL injections of JNK-2 solution into heparin- and heparin derivative-free buffer. At least two independent titration experiments were performed for each system at 25° C. to determine the binding constant of HBSPCM to heparin derivatives. Binding stoichiometry, N, enthalpy, $\Delta H_b$, entropy, $\Delta S$, and equilibrium association constants, $K_a$, were determined by fitting the corrected data to a bimolecular interaction model. This study demonstrated high binding affinity and enthalpy of interaction of JNK-2 molecules to heparin derivatives. Table 5 shows the summary of isothermal titration calorimetry (ITC) results for JNK-2 titrations with unfractionated heparin, Enoxoparin and Fondaparinux.

TABLE 5

SUMMARY OF JNK-2 TITRATIONS

| Macromolecule | N[1] | $K_a$ (M$^{-1}$) | $\Delta G$ (kcal/mol) | $\Delta H$ (kcal/mol) | T$\Delta S$ (kcal/mol) |
|---|---|---|---|---|---|
| Unfractionated heparin | 0.9 (±0.I) | 1A (±0.7) × 106 | −8.3 (±0.2) | −94 (±15) | −85 (±15) |
| LMWH (Enoxoparin) | 2.95 (±0.08) | 1.3 (±0.2) × 105 | −7.0 (±0.I) | −34.8 (±0.5) | −27.8 (±0A) |
| Fondaparinux | 2.3 (±0.0I) | 1.5 (±0.2) × 105 | −7.1 (±0.I) | −17.9 (±0.2) | −10.9 (±0.I) |

[1]N = number of heparin molecules that binds to one JNK-2 (molecular weight = 48 kDa). Experiments performed at 25° C. (errors represent the standard deviations of replicate experiments). ~G, ~H, T∆S are calculated per mole of macromolecule.

Example 22

Heparin and Heparin Derivative Neutralization in Living Rats

The present example examines heparin binding polymer effectiveness in vivo. HBSPCM polymers were tested for their ability to neutralize UFH and LMWH in living rats. Rats were first injected with heparin or heparin derivative, and then injected with the JNK-1 polymers, protamine or saline control to neutralize the previously administered heparin or heparin derivative. Neutralization was measured by detecting the percentage of factor Xa using an anti-Xa assay as a measure of anticoagulant activity.

Figure 8A:
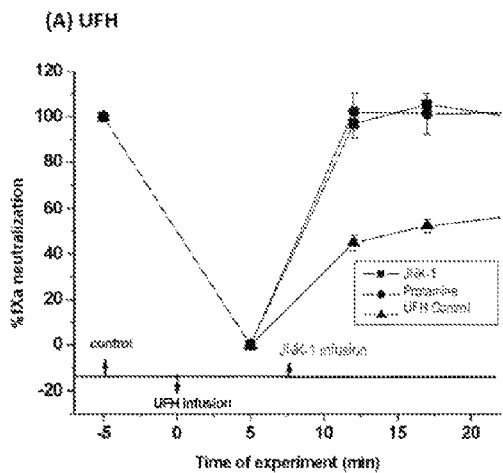
FIGS. 8A-8C are graphs depicting heparin binding synthetic polyvalent cationic macromolecule JNK-1 neutralization of unfractionated heparin (UFH) and low molecular weight heparin (LMWH) Tinzaparin in rats.
Figure 8B:
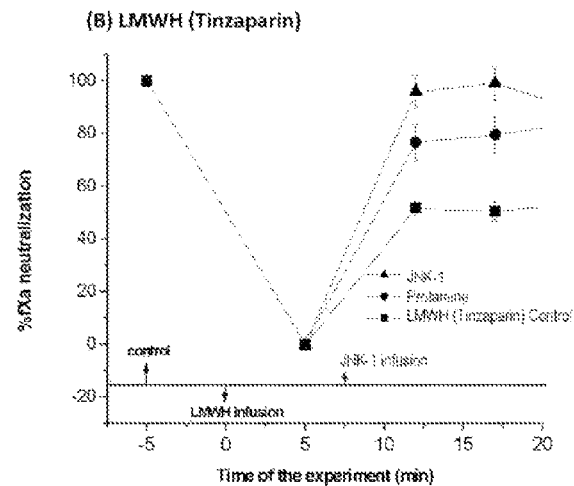
Figure 8C:
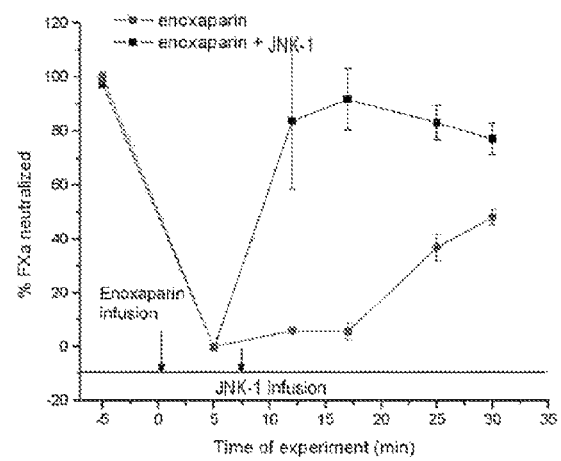

The results are shown in FIGS. 8A-8D. The data in FIG. 8A-8D demonstrates the ability of JNK-1 and JNK-5 (HBSPCM-3) polymers to neutralize UFH and LMWH (Tinzaparin and Exonaparin) in rats. FIG. 8A shows data for protamine+UFH and UFH alone and FIG. 8B shows data for protamine+Tinzaparin and Tinzaparin alone, were compared to JNK-1 polymers+UFH (FIG. 8A) and JNK-1 polymers+Tinzaparin (FIG. 8B), respectively. In addition, Enoxaparin alone and JNK-1 polymers+Enoxaparin were compared (FIG. 8C). An anti-Xa assay was used to measure heparin activity in rat blood. In this pilot study, rats were injected with 25 U of UFH, Tinzaparin or Enoxaparin (0 minutes). Blood was collected after UFH, Tinzaparin, or Enoxaparin infusion (5 minutes). Approximately 1 mg of JNK-1 polymers or protamine (dose was 3 mg/kg) was injected at 7 minutes and the blood was collected at 12 minutes after UFH/Tinzaparin/Enoxaparin infusion (5 minutes after JNK-1 infusion), and 17 minutes (10 minutes after JNK-1 polymer infusion). For subjects receiving Enoxaparin, blood was collected at additional time points (25 minutes and 30 minutes). Blood samples collected before the UFH, Enoxaparin or Tinzaparin infusion were used as a base control. JNK-1 polymers fully neutralize the anticoagulant activity of UFH, Enoxaparin and Tinzaparin and factor Xa levels reach almost to control levels after JNK-1 polymer infusion. Each data point shown reflects an average and standard deviation from five rats. The chronological order of events during the experiment is given on the bottom portion of the graphs in FIGS. 8A-8C; arrows indicate the time points.

The data in FIG. 8A show that for unfractionated heparin (UFH), the JNK-1 polymers can completely neutralize the UFH within at most five minutes after infusion, performed equally well as protamine and outperformed the control. The data in FIG. 8B shows that for low molecular weight heparin (LMWH), the JNK-1 polymers can completely neutralize the LMWH within at most five minutes after infusion, outperforming both protamine and the control, which could not completely neutralize the LMWH.

Figure 8D:
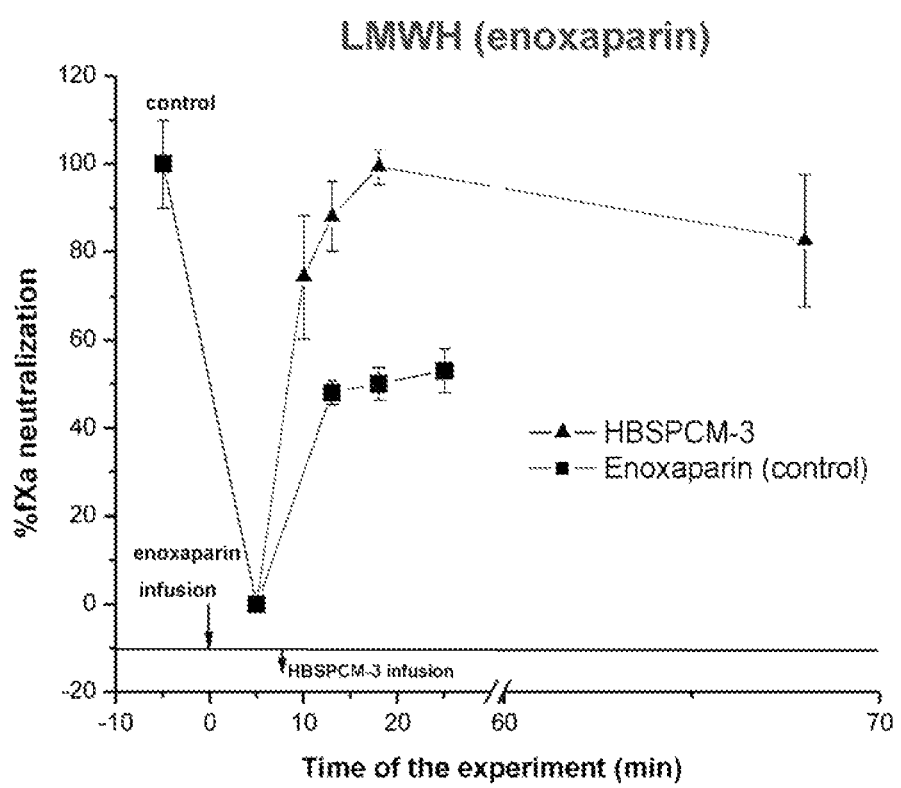
FIG. 8D is a graph depicting in vivo UFH and LMWH (by HBSPCM-3) neutralization in rats.

The data in FIG. 8D shows the ability of JNK-5 polymer to neutralize LMWH enoxaparin in rats. Rats were injected with 25 U of Enoxaparin (0 minutes). Blood was collected after enoxaparin infusion (5 minutes). Approximately 1 mg of JNK-5 polymers or protamine (dose was 3 mg/kg) was injected at 7 minutes and the blood was collected at 12 minutes after enoxaparin infusion (5 minutes after JNK-5 infusion), 17 minutes (10 minutes after JNK-5 polymer infusion) and 65 minutes (one hour after JNK-5 polymer infusion). For subjects receiving enoxaparin, blood was collected at additional time point (25 minutes). Blood samples collected before the enoxaparin infusion were used as a base control. JNK-5 polymers fully neutralize the anticoagulant activity of enoxaparin and factor Xa levels reach almost to control levels after JNK-5 polymer infusion. Each data point shown reflects an average and standard deviation from five rats. The chronological order of events during the experiment is given on the bottom portion of the graphs in FIG. 8D; arrows indicate the time points.

Example 23

Heparin and Heparin Derivative Neutralization in Living Rats

Figure 21A:
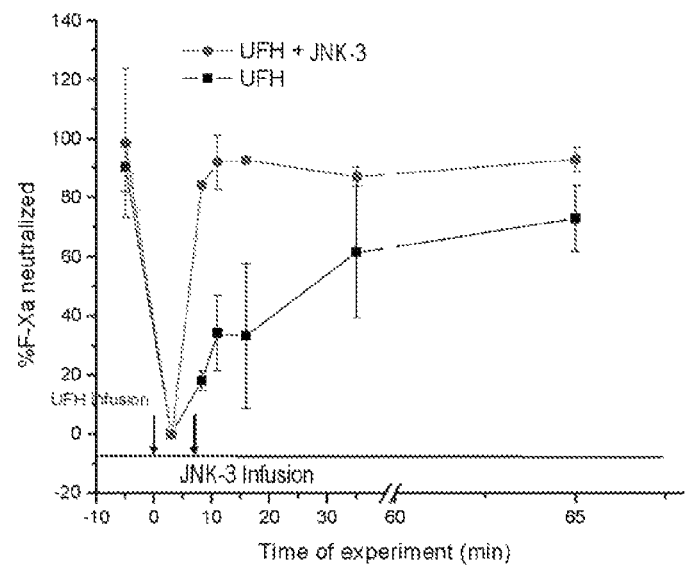
FIG. 21A and FIG. 21B are graphs depicting the ability of HBSPCM polymer JNK-3 to neutralize unfractionated heparin (FIG. 21A) and Exonaparin (FIG. 21B) in living rats.
Figure 21B:
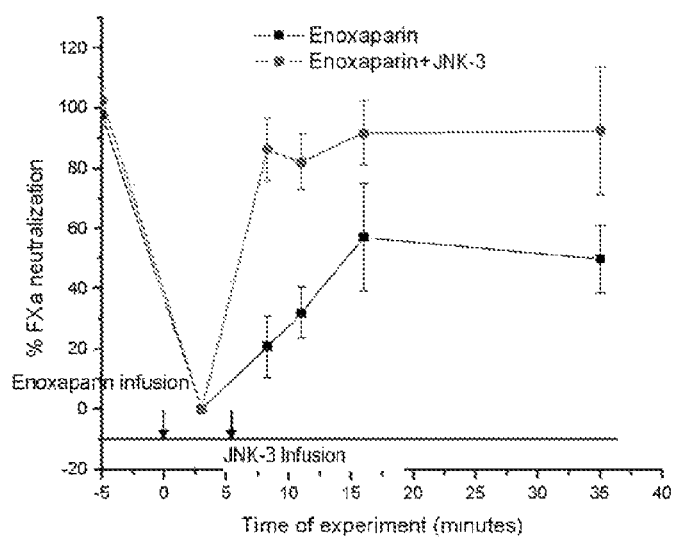

The data in FIGS. 21A and 21B demonstrate the ability of another embodiment, JNK-3 polymers, to neutralize UFH and LMWH Enoxaparin in living rats. Unfractionated heparin (UFH) alone and JNK-3 polymers+UFH were compared (FIG. 21A). Enoxaparin alone and JNK-3 polymers+Enoxaparin were compared (FIG. 21B). An anti-Xa assay was used to measure heparin activity in rat blood.

In this study, rats were injected with 25 U of UFH or Enoxaparin (0 minutes). Blood was collected after UFH or Enoxaparin infusion (3 minutes). 1 mg of JNK-3 polymers was injected at 5 minutes and the blood was collected at 7, 10, 15 and 35 minutes after UFH/Enoxaparin infusion. For subjects receiving UFH infusion, blood was also collected at 65 minutes. Blood samples collected before the UFH or Enoxaparin infusion were used as a base control. JNK-3 polymers fully neutralize the anticoagulant activity of UFH and Enoxaparin and factor Xa levels reach almost to control levels. The chronological order of event during the experiment is given on the bottom portion of the graphs in FIG. 21; arrows indicate the time points.

These in vivo studies indicate that heparin binding polymers, including both JNK-1 and JNK-3 polymers, work effectively on both UFH and LMWH in the intact living system of rat model, providing evidence that the findings may be extrapolated to systemic human use.

Example 24

Heparin and Heparin Derivative Neutralization in an Extracorporeal Device

The present example is directed to an extracorporeal device that can be used to remove and/or reduce heparin and derivatives thereof. The blood from a subject previously administered with heparin or heparin derivatives is directed into an extracorporeal circuit bypass of a circulation system is filtered for the removal of heparin or heparin derivatives for reuse by the subject.

The extracorporeal device can include a structure including, but not limited to, a cylindrical cartridge, hollow tubing, a rigid or flexible vesicle, and the like. HBSPCM polymers are attached to some the part of the extracorporeal device coming into contact with blood and are attached either directly, or through a means of tethering. Tethering can include, but is not limited to, polymer brushes or surface functionalities or by non-covalent complexation (electrostatic).

As blood is moved through the extracorporeal device, after it leaves the subject and before it is returned to the subject, HBSPCM polymers attached to the device neutralize heparin or heparin derivatives in the blood.

Example 25

Blood Compatibility Analysis

Blood compatibility of the polymers was assessed by several methods (blood coagulation, platelet activation, complement activation, red cell hemolysis and aggregation. The change in activated partial thromboplastin time (APTT) was evaluated in comparison to a saline control. A significant change in the APTT shown by the heparin binding polymers as compared to a saline control suggests that the HBSPCM polymers are not interfering with blood coagulation proteins such as tissue factor and other coagulation factors.

Figure 15:
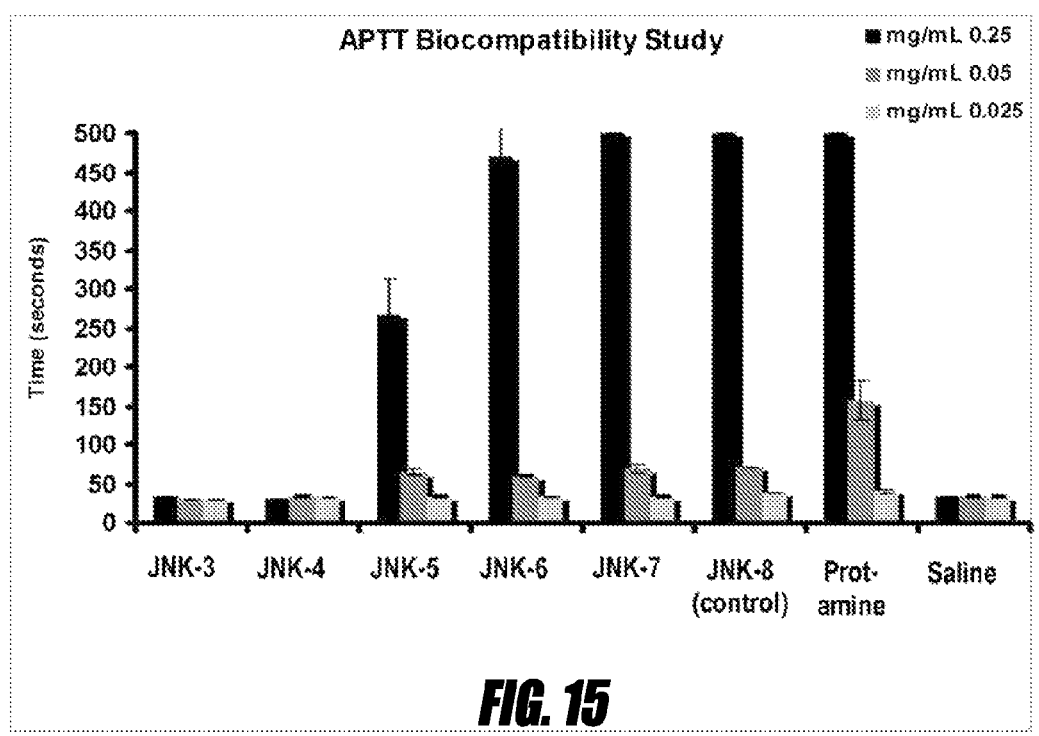
FIG. 15 is a bar graph depicting a blood compatibility analysis (activated partial thromboplastin time (APTT) biocompatibility) of HBSPCM polymers JNK-3 through JNK-8-control as compared to protamine and saline.

FIG. 15 shows an analysis of blood compatibility by demonstrating the activated partial thromboplastin time (APTT) assay by the HBSPCM polymers described in Table 2. Blood coagulation is measured using APTT. The amine content changed the APTT and protamine resulted in a different blood coagulation profile.

Figure 16:
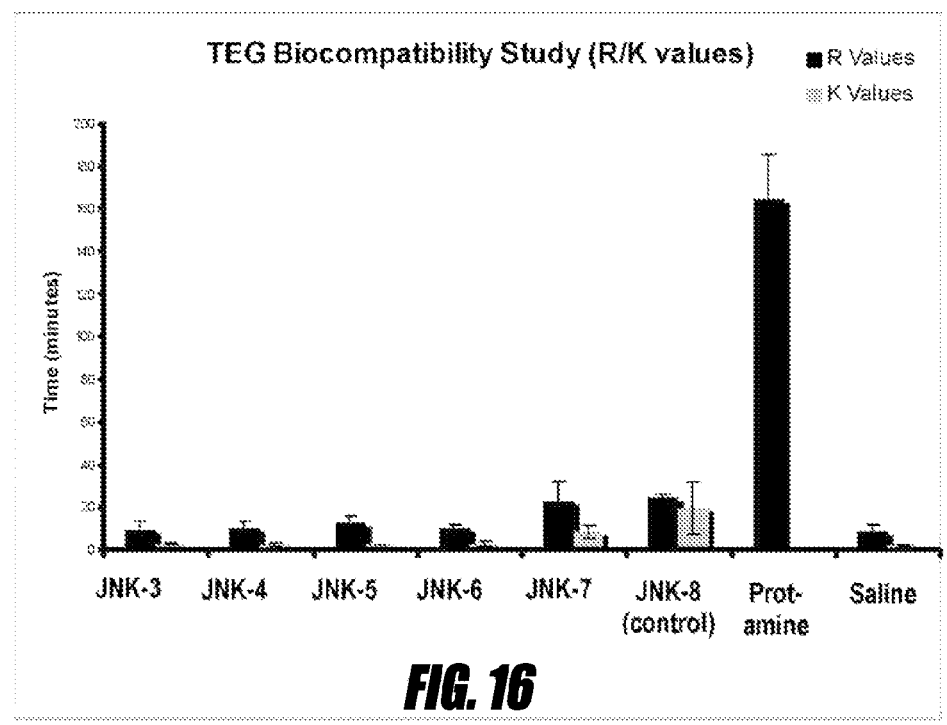
FIG. 16 is a graph depicting blood compatibility analysis using thromboelastograph (TEG) in terms of coagulation time and kinetics parameter of HBSPCM polymers JNK-3 through JNK-8-control as compared to protamine and saline.

FIG. 16 shows another analysis of blood compatibility using thromboelastograph (TEG) in terms of coagulation time (R) and kinetics parameter (K) at a polymer concentration of 0.5 mg/ml for the polymers described in Table 2. TEG studies yielded the cumulative effect of several components of coagulation (global homeostasis) as a function of time. The polymers with higher amine content and protamine resulted in a different blood coagulation profile.

Example 26

Rate of Red Blood Cell Lysis

This example examines the rate of red blood cell lysis in the presence of a heparin binding polymer.

Red blood aggregation in plasma/buffer is not easily disrupted by shear forces and can result in high blood viscosity and complications. Severe aggregation can cause cell damage and hemolysis, leading to a variety of complications including anemia and jaundice. Red blood cell hemolysis shows the toxicity of the compounds tested.

In the present example, the degree of hemolysis was observed by monitoring the degree of red color present in the supernatant plasma or buffer upon centrifugation of the red blood cells after incubation for 1 hour at 37° C. with heparin binding polymers. Red blood cell lysis was determined by measuring the amount of extracellular hemoglobin against the total hemoglobin concentration. Briefly, 50 microliters of red blood cell suspension and 100 microliters of red blood cell supernatant were mixed with Drabkin's reagent (1 ml each) and the absorbance was monitored at 540 nm running Drabkin's reagent as blank.

Figure 17A:
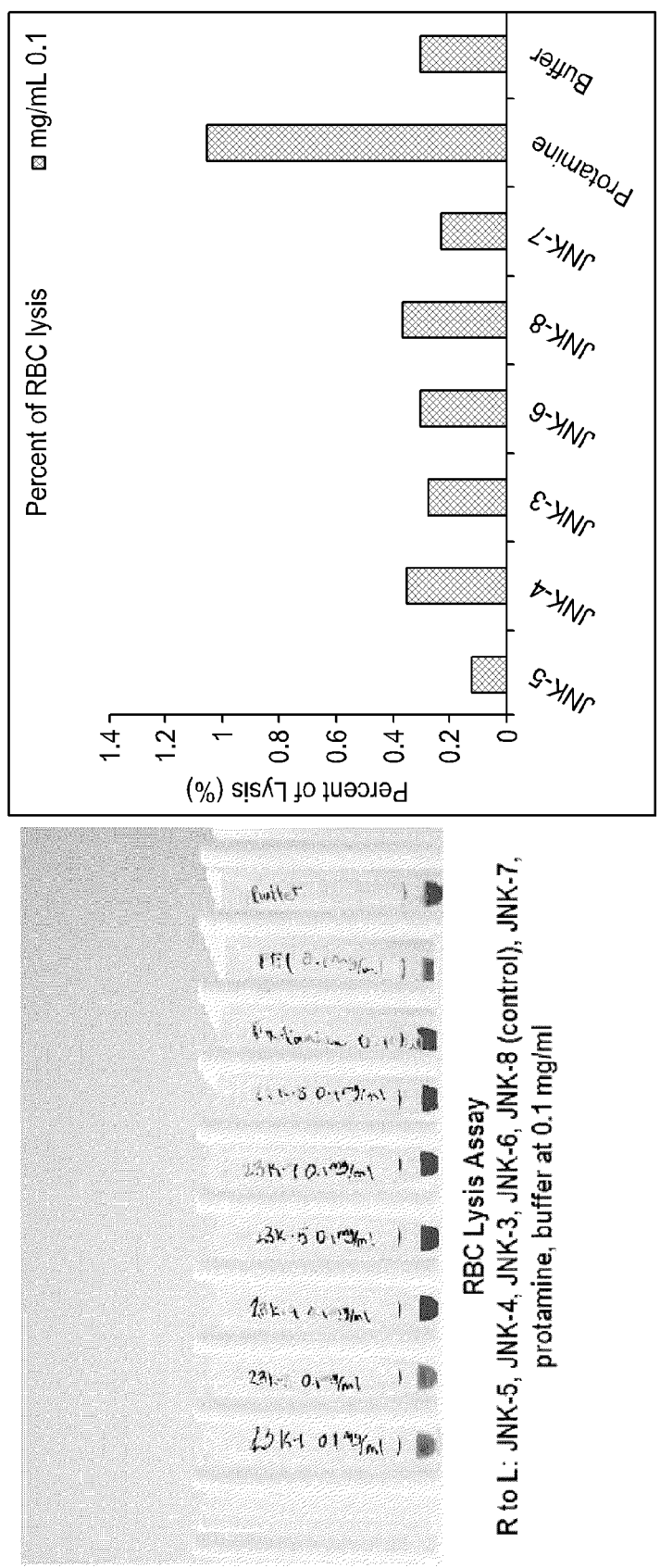
FIG. 17A and FIG. 17B are photos and bar charts depicting red blood cell lysis after incubation with HBSPCM polymers JNK-3 through JNK-8 as compared to protamine and saline.
Figure 17B:
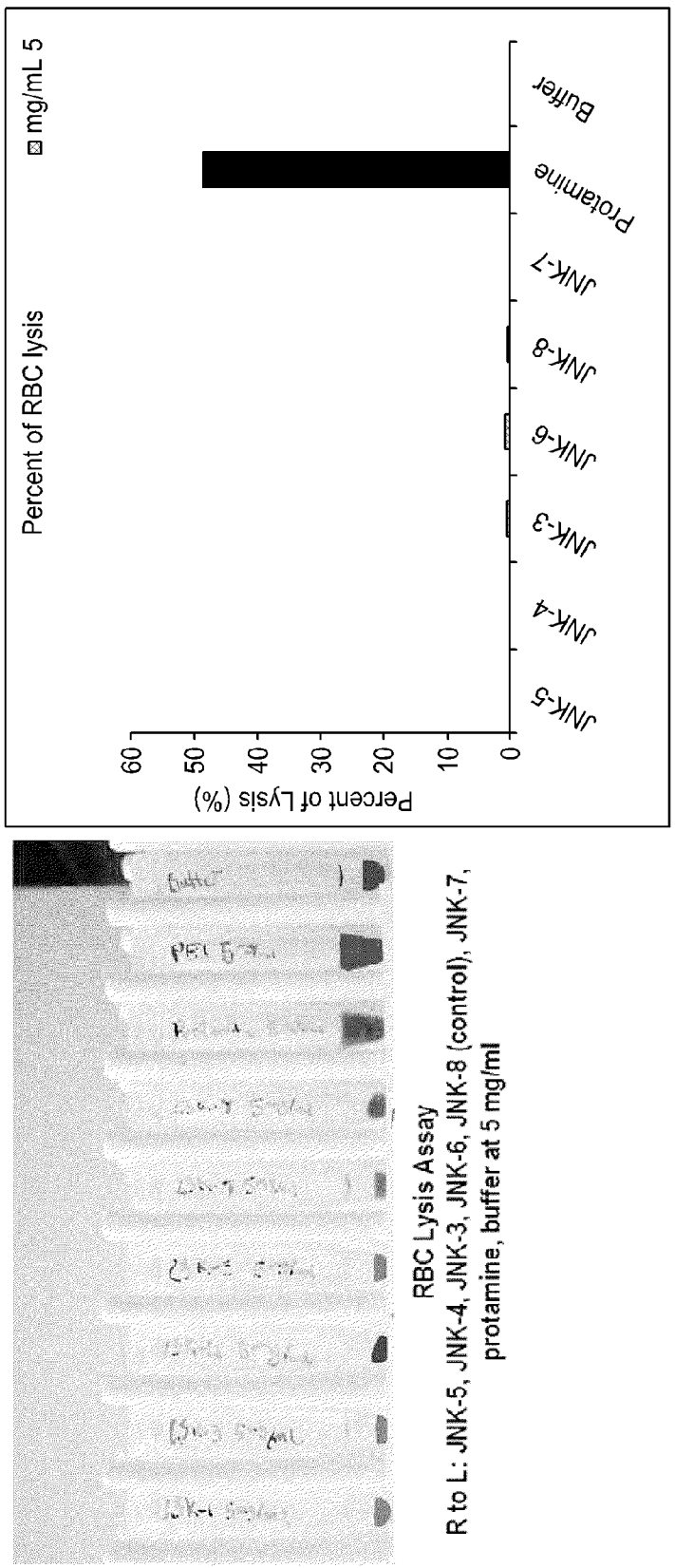

FIG. 17A and FIG. 17B demonstrate the results of a red blood cell lysis assay, which measured the percent of red blood cells that were lysed after incubating different HBSPCM polymers as described in Table 2 with red blood cells at 37° C. for 1 hour at two different concentrations: (FIG. 17A) 0.1 mg/ml; (FIG. 17B) 5 mg/ml. Shown on the left side of FIG. 17A and FIG. 17B are photographs of red blood cell suspensions centrifuged after incubation with the polymers.

Example 27

Tolerance of HBSPCM Polymers in Mice

The present example examines the degree of tolerance that animals have to various heparin binding polymers, and to HBSPCMs in particular.

Figure 22:
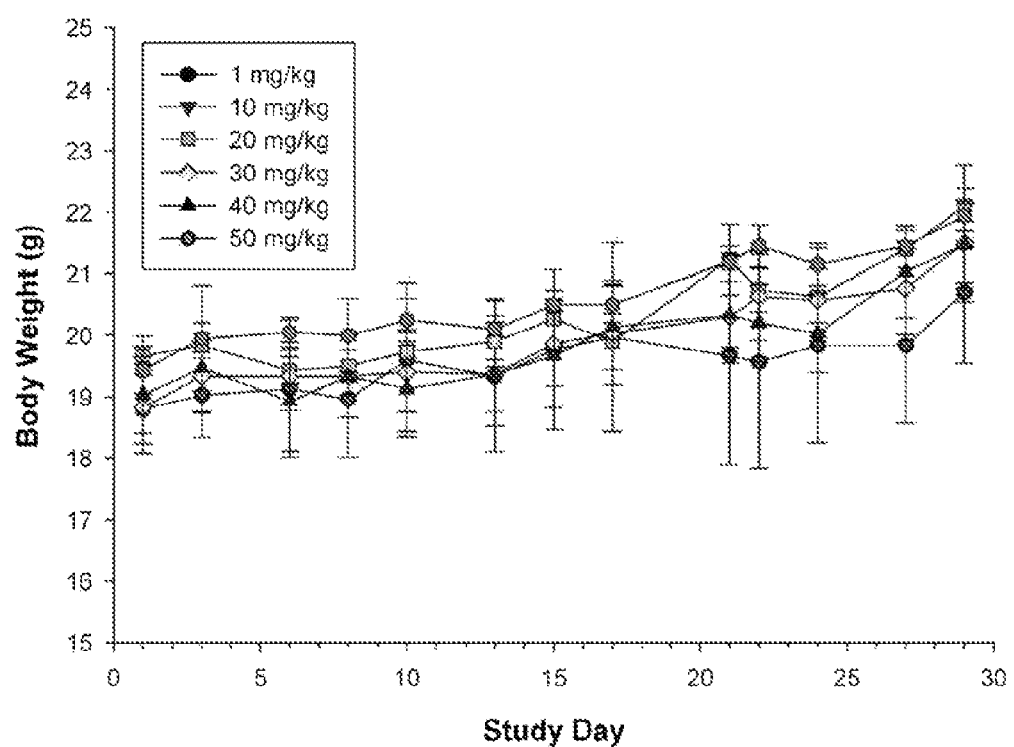
FIG. 22 is a graph plotting body weight over time (0 to 29 days post injection) of female BALB/c mice treated with HBSPCM polymer JNK-3 by bolus intravenous injection.

FIG. 22 shows the body weights over time (0 to 29 days post injection) of female BALB/c mice treated with JNK-3 polymers (23 kDa) by bolus intravenous injection of increasing concentration of JNK-3 polymers (1 mg/kg to 50 mg/kg). Mice were randomly assigned to dosing groups. All injections (200 μL of HBSPCM in saline) were performed as scheduled with no adverse reactions noted. No significant decreases in body weight or behavioral changes were noted following administration of JNK-3 polymers. All the mice were terminated as per study protocol on the $29^{th}$ day with no notation on necropsy.

The results show that JNK-3 polymers can be safely dosed by bolus intravenous administration in female BALB/c mice at a dose of up to 50 mg/kg (maximum dosage given). The tolerated dose is at least 16-fold higher as compared to protamine, which has a maximum tolerated dose of 3 mg/kg. The study was carried out in the Department of Advanced Therapeutics, British Columbia Cancer Agency, Vancouver, under an approved UBC animal ethics protocol.

Example 28

Cytotoxicity of HBSPCM Polymers

The present example examines the cytotoxicity of a heparin binding polymer. The lactate dehydrogenase (LDH) assay demonstrates the cytotoxicity present in a sample containing cells based on the activity of LDH released from damaged cells. The LDH assay was used to assess the cytotoxicity of a HBSPCM polymer, JNK-3.

Figure 23:
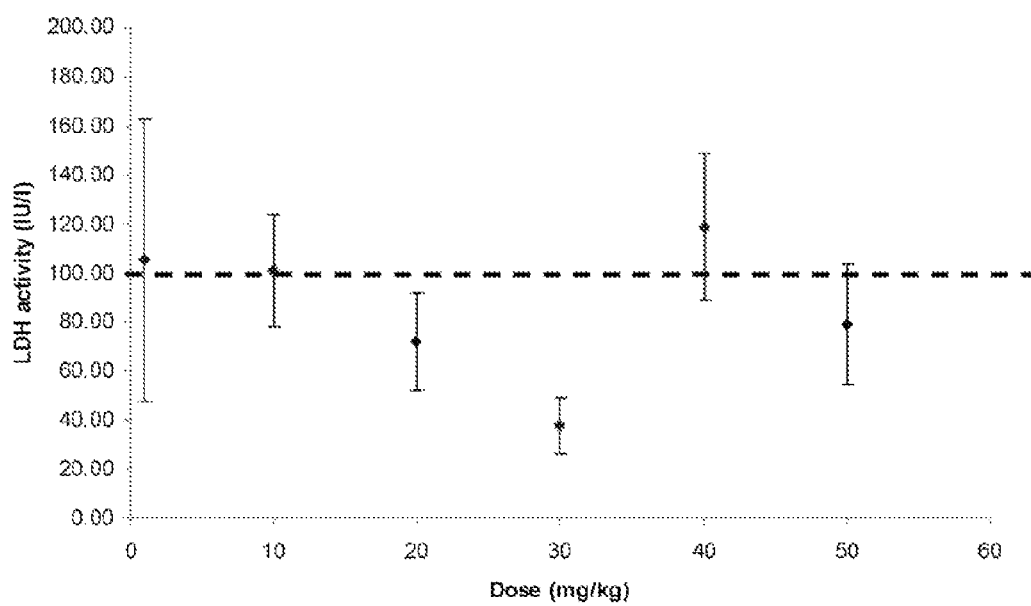
FIG. 23 is a graph depicting LDH activity in serum of female BALB/c mice treated with HBSPCM polymer JNK-3 after a bolus intravenous injection.

FIG. 23 demonstrates the LDH activity in serum of female BALB/c mice treated with JNK-3 polymers (23 kDa) after an intravenously applied bolus given on day 0 of increasing concentration (1 mg/kg to 50 mg/kg) as measured on the termination day ($29^{th}$ day of post injection). The results demonstrate that the LDH activity associated with all doses was either below or not dramatically greater than the control activity level. Results dramatically higher than the control activity level would have been indicative of liver and cell toxicity associated with the HBSPCM polymers (JNK-3). Base LDH activity levels for control mice were around 100 IU/I (dotted line in FIG. 23).

Example 29

The present example outlines a method of making HBSPCM polymers JNK-1 and JNK-2. The HBSPCM polymers JNK-1 and JNK-2 were synthesized using similar protocols to that of polymers JNK-3 to JNK-11. The average number of charge in JNK-1 and JNK-2 are 276 and 112 respectively. Synthetic procedure for JNK-1 is given below.

Synthesis of Polymer JNK-1 (116 kDa HBSPCM Polymer)

The synthesis steps include the following. Firstly, a HPG-PEG-116K precursor polymer was synthesized using the following steps. A three-necked round bottomed flask was cooled under vacuum and filled with argon. To this, 1,1,1-Tris (hydroxymethyl)propane (TMP, 0.120 g) and potassium methylate (25 wt % solution in methanol, 0.110 mL) were added and stirred for 30 minutes. Methanol was removed under vacuum for 4 hours. The flask was heated to 95° C. and glycidol (6 mL) was added over a period of 15 hours. After complete addition of monomer, the reaction mixture was stirred for additional 3 hours. MPEG-epoxide-400 (20 mL) was added over a period of 12 hours. The reaction mixture was stirred for additional 4 hours. The polymer was dissolved in methanol, passed through Amberlite IRC-50 resin to remove the potassium ions and twice precipitated from diethyl ether. The polymer was dissolved in water and dialyzed against water using MWCO-1000 membrane for 3 days with periodic changes in water.

The JNK-1 polymer was synthesized from the HPG-PEG-116K precursor polymer described in the previous paragraph as follows. HPG-PEG-116K (16 g) was dissolved in 100 mL of pyridine. To this, p-toluene sulfonyl chloride was added and stirred at room temperature for 24 hours. Pyridine was removed by rotary evaporation; the polymer was dissolved in 0.1 N HCl and dialyzed overnight. The polymer was isolated by freeze drying. The dried polymer and tris(2-aminoethylamine) (2 mL) were dissolved in 1,4-dioxane (100 mL) and refluxed for 24 hours. Dioxane was removed under vacuum. The polymer was dissolved in minimum amount of methanol and precipitated twice from diethyl ether. Polymer was dissolved in water and dialyzed against water using MWCO-1000 membrane for 2 days. The resulting polymer solution was added to a mixture of formaldehyde (15 mL) and formic acid (15 mL) at 0° C. The reaction mixture was refluxed overnight. After cooling to room temperature, the pH of the solution was adjusted to 10 using NaOH and the polymer was extracted with dichloromethane. Dichloromethane was removed under vacuum; the polymer dissolved in water and dialyzed using MWCO-1000 membrane for 3 days. The yield of JNK-1 polymer was 10 g, and the amine content (by conductometric titration) was 5.4 mol %.

Synthesis of JNK-2 Polymer (48 kDa HBSPCM Polymer)

JNK-2 polymer was synthesized using similar procedure as that for JNK-1. First, a HPG-PEG-48K precursor polymer was synthesized and a portion of the hydroxyl groups were converted into tertiary amino groups by a similar procedure. Amine content of the polymer (by conductometric titration) was 7.6 mol %.

Example 30

Comparative Analysis of UFH Embodiments Vs. Tinzaparin and Enoxaparin

This example was performed to present a comparative analysis of UFH embodiments vs. Tinzaparin and Enoxaparin.

FIGS. 24A-24C show the ability of HBSPCM polymers JNK-9, JNK-10 and JNK-11 to neutralize UFH and LMWH tinzaparin and enoxaparin in comparison to protamine and saline control as measured by activated partial thromboplastin time (APTT).

FIG. 24A shows the neutralization of UFH by JNK-9, JNK-10 and JNK-11.

FIG. 24B shows the neutralization of LMWH Tinzaparin by JNK-9, JNK-10 and JNK-11.

FIG. 24C shows the neutralization of LMWH Enoxaparin by JNK-9, JNK-10 and JNK-11.

Ability of HBSPCM polymers JNK-9, JNK-10 and JNK-11 was studied for the range of concentration from 0.01 to 0.25 mg/mL prepared in 0.15 M saline. Citrated blood was spun at 3000 RPM for 10 min to obtain platelet poor plasma (PPP). The PPP was then heparinized by adding 45 μL of heparin (UFH, LMWH etc.) to 2200 μL of PPP—final concentration of 2.0 IU/mL for UFH and Tinzaparin and 1.14 IU/mL for Enoxaparin. Normal control was prepared by adding 25 μL of 0.15 M saline to 250 μA of PPP. 25 μL of each antidote solution (polymer or protamine) was added to 225 uL of heparinized PPP. 250 μL of APTT reagent (actin FSL) was then added and samples were incubated for 3 min at 37° C. 250 μL of normal control was combined with 250 uL of APTT reagent and also incubated for 3 min. 50 μL of 0.025M $CaCl_2$ was added to 100 μL aliquots of normal control and sample (in triplicate). A heparinized control containing 225 uL of PPP and 25 μL of saline was also prepared and run similar to normal control. The results indicate that HBSPCM polymers JNK-9, JNK-10 and JNK-11 effectively neutralize UFH and LMWH tinzaparin and enoxaparin over a broader range of concentration, while protamine neutralizes UFH and LMWH only in the narrow concentration range, and at higher concentrations protamine possesses anticoagulant activity.

Example 31

Blood Compatibility of Various HBSPCMs

This example examined blood compatibility of various HBSPCMs, and in particular the effect of the charge on the polymer.

Figure 25:
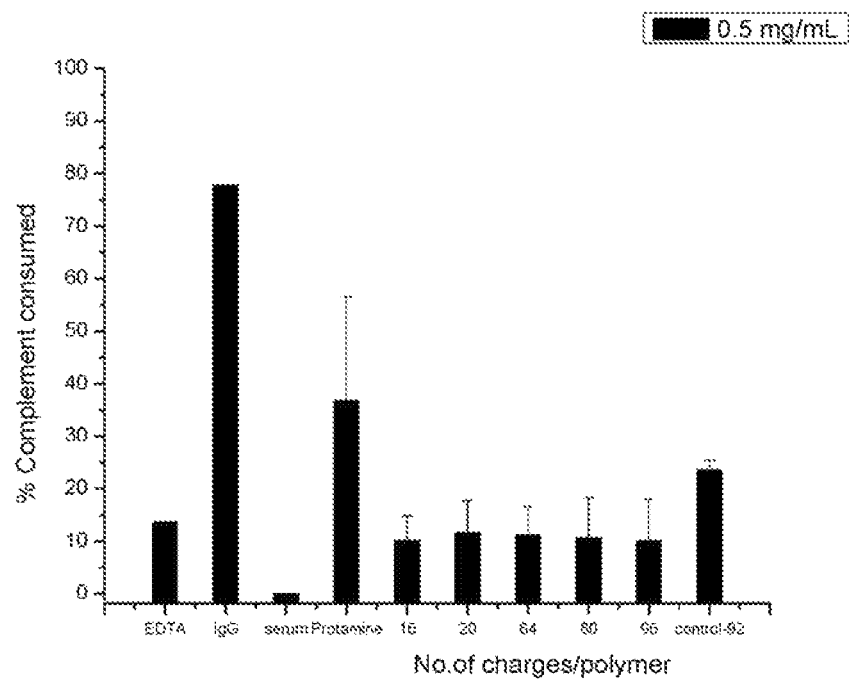
FIG. 25 is a bar graph depicting blood compatibility (complement activation) of HBSPCM and the effect of the number of charges on the polymer.

FIG. 25 shows the complement activation of HBSPCM polymer having a molecular weight of 23 kDa with different charge density (e.g., number of amine groups). The level of complement activation was measured by a CH50 sheep erythrocyte lysis assay. Ten microliter of each of the 0.5 and 5 mg/mL polymers or protamine was mixed with 90 μL of serum for 1 h at 37° C. The final concentration of polymer/protamine to serum was 0.05 and 0.5 mg/mL. One mg/mL heat-activated human IgG and 5 mM EDTA, after mixing with serum, were the positive and negative controls, respectively, for the study. 60 μL of post-incubation serum/polymer or protamine mixture was diluted by 120 μL of $GVB^{2+}$ (CompTech). Seventy-five microliter of $GVB^{2+}$ diluted serum/polymer or protamine mixture was incubated for 1 h at 37° C. with 75 μL of Ab-sensitized sheep erythrocyte (CompTech). The reaction was stopped by addition of 300 μL cold GVB-EDTA to each sample. The samples were centrifuged and the optical density of supernatant was measured at 540 nm. One hundred percent lysis of the sheep erythrocyte was done by $dH_2O$. The percentage of complement activation was calculated by 100-% lysis of sheep erythrocytes.

The results reveal that 23 kDa HBSPCM polymer with 16-96 charges per polymer molecular do not activate the complement system, whereas the polymer control sample with 92 charges (where the primary amino groups are not methylated) and protamine showed significant complement activation.

Figure 26:
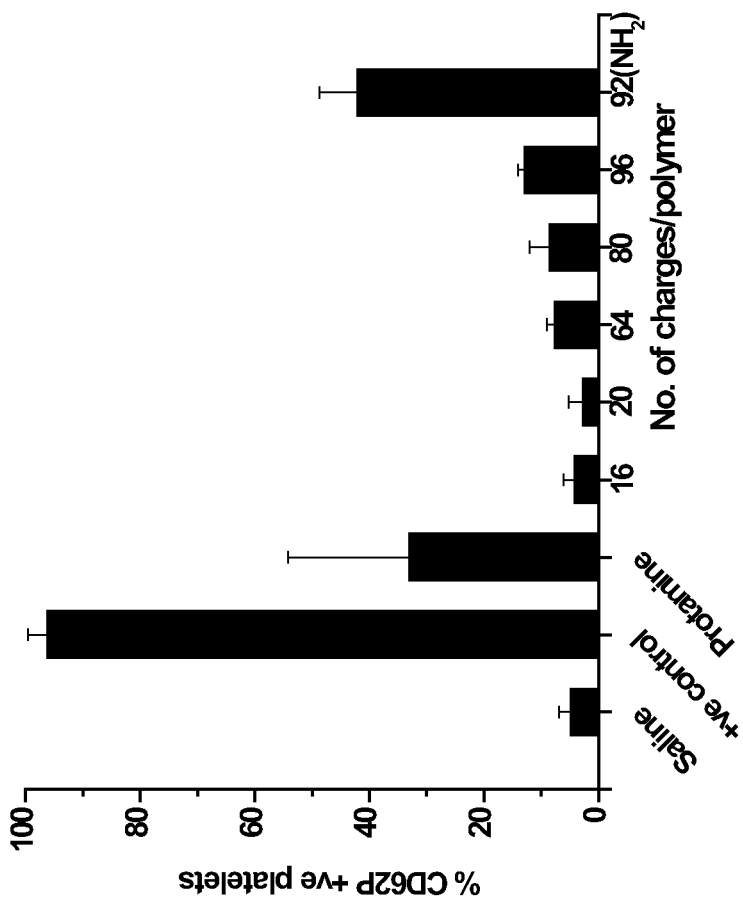
FIG. 26 is a bar graph depicting blood compatibility (platelet activation) of HBSPCM and the effect of the number of charges on the polymer.

FIG. 26 shows the platelet activation of 23 kDa HBSPCM polymers having a different number of amine groups per polymer molecule (16-80 amine groups/polymer molecule). The level of platelet activation was quantified by flow cytometry. Ninety microliter of PRP was incubated at 37° C. with 10 μL of 5 mg/mL of polymer or protamine (final concentration 0.5 mg/mL). After 1 h, aliquots of the incubation mixtures were removed for assessment of the platelet activation state. Five microliter of post-incubation platelet/polymer or protamine mixture, diluted in HEPES buffer, was incubated for 20 minutes in the dark with 5 μL of monoclonal anti-CD62-PE (Immunotech). The samples were then stopped with 0.5 mL of phosphate-buffered saline solution. The level of platelet activation was analyzed in a BD FACSCanto II flow cytometer (Becton Dickinson) by gating platelets specific events based on their FITC-CD42 fluorescence and light scattering profile. Activation of platelets was expressed as the percentage of platelet activation marker CD62-PE fluorescence detected in the 10,000 total events counted. Duplicate measurements were done, the mean of which was reported. Controls were done for the flow cytometric analysis. One U/ml of bovine thrombin (Sigma) was used as a positive control, and PE conjugated goat anti-mouse IgG polyclonal antibodies (Immunotech) was used as the non-specific binding control.

The results indicate that 23 kDa HBSPCM polymers with 16-80 number of charges per polymer molecule do not activate platelets, whereas protamine showed significant levels of platelet activation.

Example 32

Tolerance of HBSPCM Vs. Protamine

This example examined the tolerance of HBSPCM vs. protamine in mice.

Figure 27:
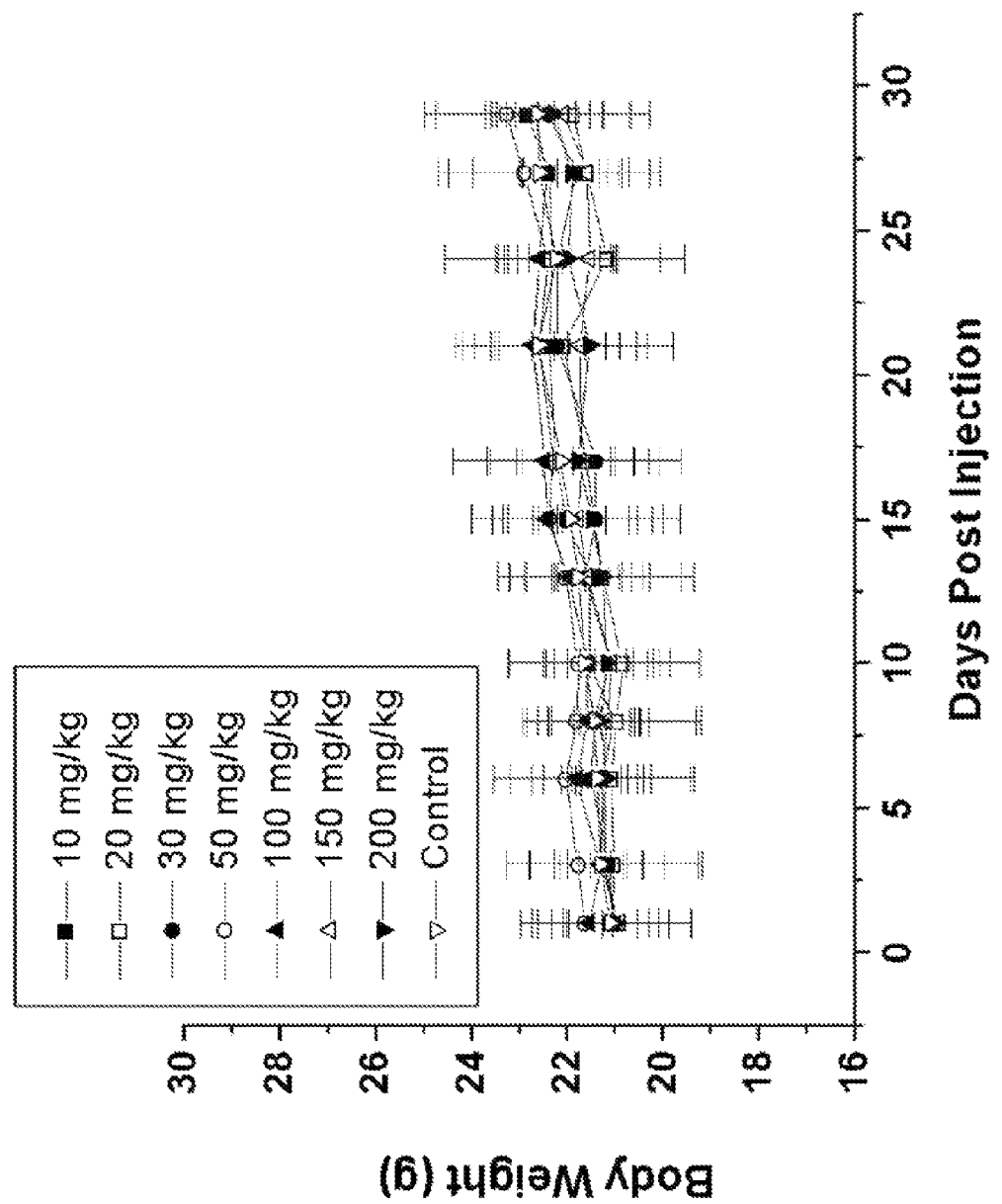
FIG. 27 is a graph depicting the tolerance of mice to HBSPCM (JNK-1)
Figure 28:
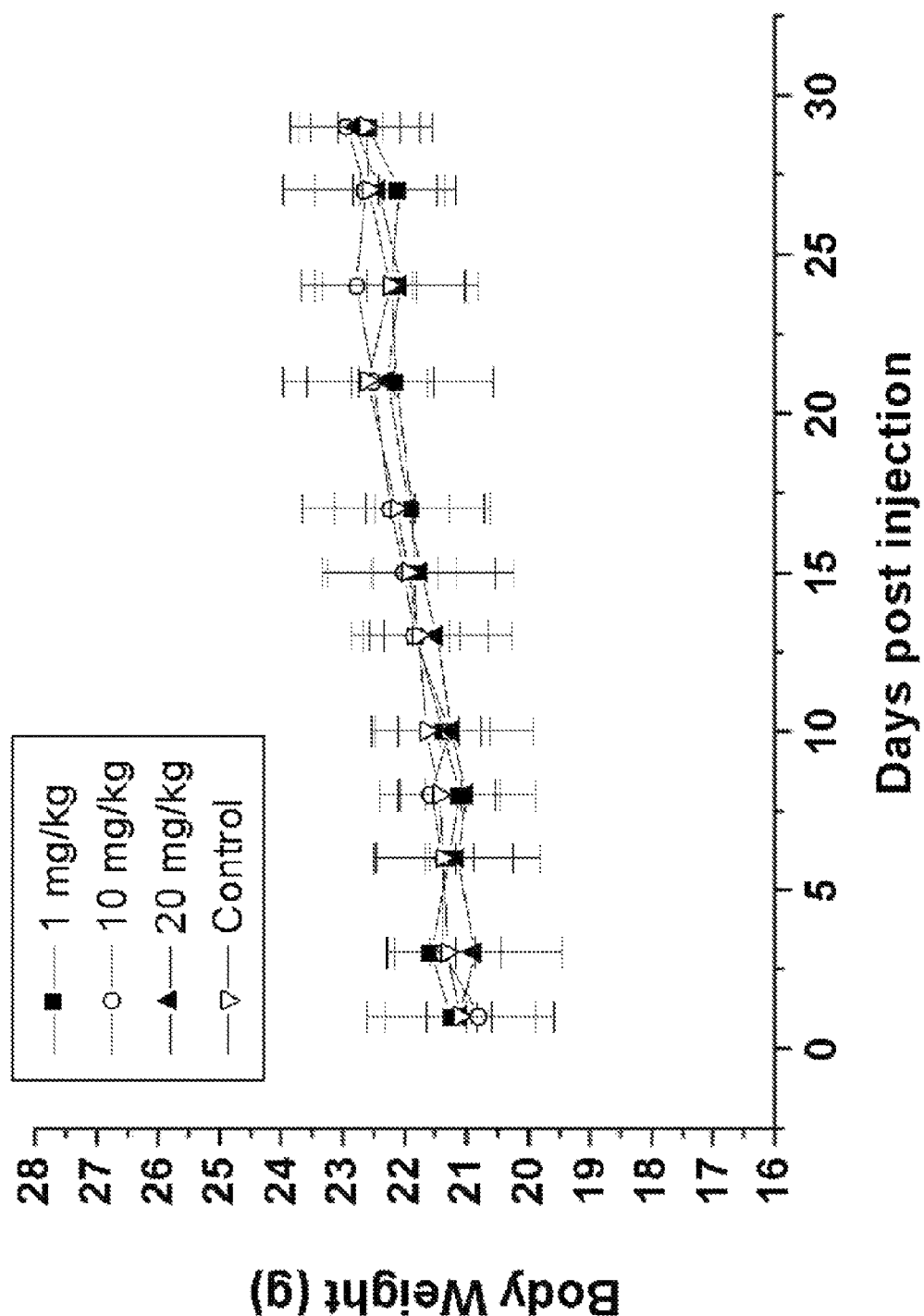
FIG. 28 is a graph depicting the tolerance of mice to protamine.

FIGS. 27 and 28 show the single dose tolerability of HBSPCM polymer JNK-1 and protamine respectively, compared to a vehicle control (saline) in female Balb/cJ mice.

For the study, the mice were individually weighed and injected with a prescribed dose (mg/Kg) based on their individual weights (200 µL/20 g) of JNK-1 (FIG. 27), protamine (FIG. 28) and control saline. Mice were continually monitored for acute signs of toxicity for the first two hours following administration and for additional toxicities 28 days post administration. Body weights of the mice were measured over a period of 29 days.

The results are shown in FIG. 27 (HBSPCM) and FIG. 28 (Protamine). As is clearly shown in FIG. 27, these heparin binding polymers are not toxic in mice up to the maximal dose studied (200 mg/Kg). In contrast, as shown in FIG. 28, the maximum dose of protamine tolerated in mice was 20 mg/kg, with mice dying at doses above 20 mg/kg.

Example 33

Biodistribution of HBSPCM-3

The biodistribution of HBSPCM-3 (23 kDa) was studied. The molecule was radio-labeled (tritium) and was intravenously injected into BALB/c mice. Radio-activity in different organs and plasma was measured.

Figure 29B:
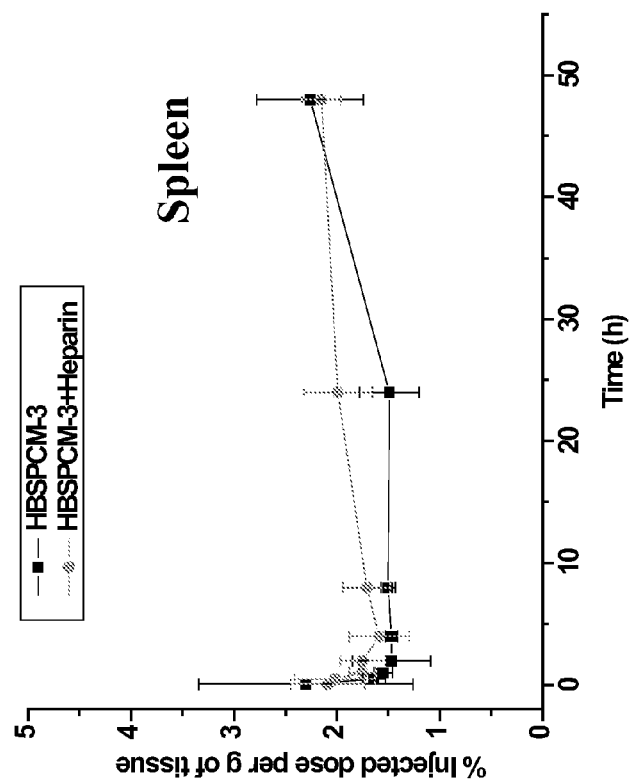
FIG. 29A and FIG. 29B are graphs depicting the bio-distribution and pharmacokinetics of HBSPCM-3 in BALB/c mice.
Figure 29A:
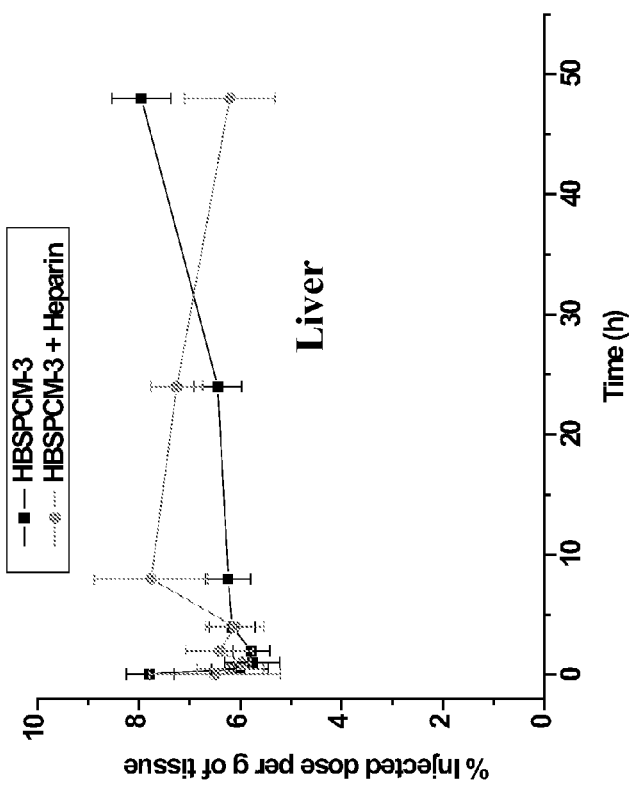

FIG. 29 and FIG. 30 show the results of the study conducted to determine the pharmacokinetics and biodistribution of HBSPCM-3 (23 kDa) polymer in female Balb/cJ mice following bolus intravenous injection.

32 female Balb/cJ mice were administered with HBSPCM-3 polymer at a dose of 20 mg/Kg. Blood was collected at 5 min, 30 min, 1 h, 2 h, 4 h, 8 h, 24 h and 48 h post intravenous single bolus injection. Four mice were terminated at each time point by $CO_2$ inhalation and blood was collected by cardiac puncture. 100 µL whole blood sample was placed in pre-weighed tubes and the remaining volume was processed for plasma. Upon termination, the liver, spleen, lung, kidney and heart were weighed and processed for scintillation counting. Livers were further processed by adding water to make a 20% homogenate solution.

As shown in the charts, there was no accumulation in the major organs such as liver, kidney and spleen suggesting non-toxic behavior of HBSPCM-3.

Example 34

Biodistribution of HBSPCM-1

Figure 32B:
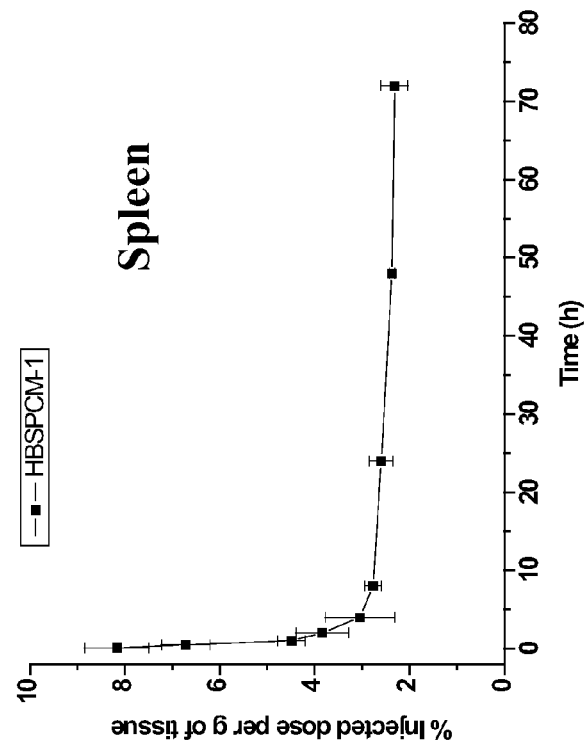
FIG. 32A and FIG. 32B are graphs depicting the bio-distribution and pharmacokinetics of HBSPCM-1 in BALB/c mice.
Figure 32A:
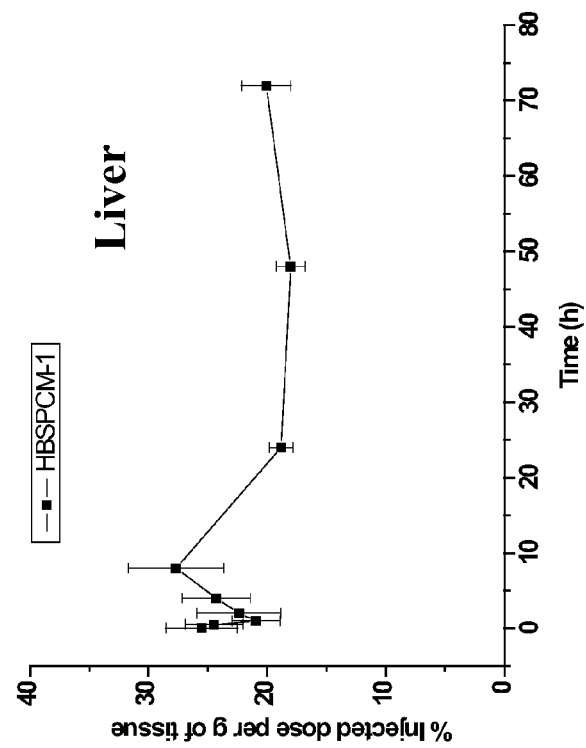

The biodistribution of HBSPCM-1 (116k) was studied. The molecule was radio-labeled (tritium) and was intravenously injected into BALB/c mice. Radio-activity in different organs and plasma was measured. FIG. 31 and FIG. 32 show the results of a study conducted to determine the pharmacokinetics and biodistribution of HBSPCM-1 (116 kDa) polymer in female Balb/cJ mice following bolus intravenous injection.

36 female Balb/cJ mice were administered with HBSPCM-1 polymer at a dose of 20 mg/kg. Blood was collected at 5 min, 30 min, 1 h, 2 h, 4 h, 8 h, 24 h, 48 h, and 72 h post intravenous single bolus injection. Four mice were terminated at each time point by $CO_2$ inhalation and blood was collected by cardiac puncture. 100 µL whole blood sample was placed in pre-weighed tubes and the remaining volume was processed for plasma. Upon termination, the liver, spleen, lung, kidney and heart were weighed and processed for scintillation counting. Livers were further processed by adding water to make a 20% homogenate solution The results are presented in FIGS. 31A, 31B, 31C, 31D, 32A, and 32B. As shown in the charts, there was no accumulation in the liver and spleen suggesting non-toxic behavior of HBSPCM.

Example 35

HBP to Reduce the Level of Effective Heparin

The present example outlines how a heparin binding polymer can be used to reduce the level of effective heparin in a subject.

A subject receiving treatment for a burn is administered an amount of heparin. The amount of heparin is deemed to be excessive at some point and the subject is then administered an adequate amount of HBSPCM-3, to counteract the amount excessive amount of heparin.

As will be appreciated by those of skill in the art, in light of the present disclosure, in some embodiments, the polymer-bound heparin can be cleared from the body depending on the molecular weight. In some embodiments, polymers of molecular weight less than 50 kDa can be cleared through the kidney, while the higher molecular weight polymers can be excreted through feces.

Example 36

Heparin Binding Polymer for Reducing Heparin Levels for a Subject Ex Vivo

The present example outlines how a heparin binding polymer can be used to reduce heparin levels for a subject ex vivo.

A subject receiving treatment for acute coronary syndrome is administered an amount of heparin. At some point, it is desired to reduce the amount of heparin in the subject, and thus, blood is taken from the subject and run through a filtering device that includes HBSPCM-1 immobilized on a support such that the blood passes over the HBSPCM-1. This allows the polymer to bind to and remove the heparin, thereby providing filtered blood. The filtered blood is then returned to the subject.

Example 37

Heparin Binding Polymer for Heparin Isolation

The present example outlines how a heparin binding polymer can be used to isolate heparin.

A solution containing heparin is provided. The solution can be the resulting mixture from a process of heparin preparation. A heparin binding polymer, which includes a polyglycerol core and polyvalent cationic groups, is immobilized on a surface. The solution is flowed across the surface at room temperature and the heparin is allowed to bind to the heparin binding polymer. The surface is then washed with water (in the alternative, a buffer solution (0.15 M NaCl or PBS or other similar solutions) can be used) and then the isolated heparin can be eluted from the polymer with a salt solution (1 to 3 M salt solution), which can be performed at room temperature, or alternatively, at body temperature. Some of the salt can then be removed from the solution to provide an isolated heparin composition in an osmotically physiological salt solution.

Example 38

HBSPCM Polymers for Drug Delivery Applications

The present example outlines the use of HBSPCM polymers for the delivery of anionic drugs such as methotrexate, phenoxymethyl penicillin, insulin, indomethacin, diclofenac etc. The cationic nature of HBSPCM polymers results in effective binding to these anionic drug molecules which could be released at a controlled rate once inside the body.

Other aspects and features various embodiments will become apparent to those ordinarily skilled in the art upon review of the following description of specific examples.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:
1. A method of counteracting heparin in a subject, the method comprising administering a heparin binding polymer to a subject, the heparin binding polymer comprising:
   a first dendritic polyol; and
   one or more cationic moieties attached to the first dendritic polyol, wherein the polymer comprises at least one of:
a) the structure of Formula (I):

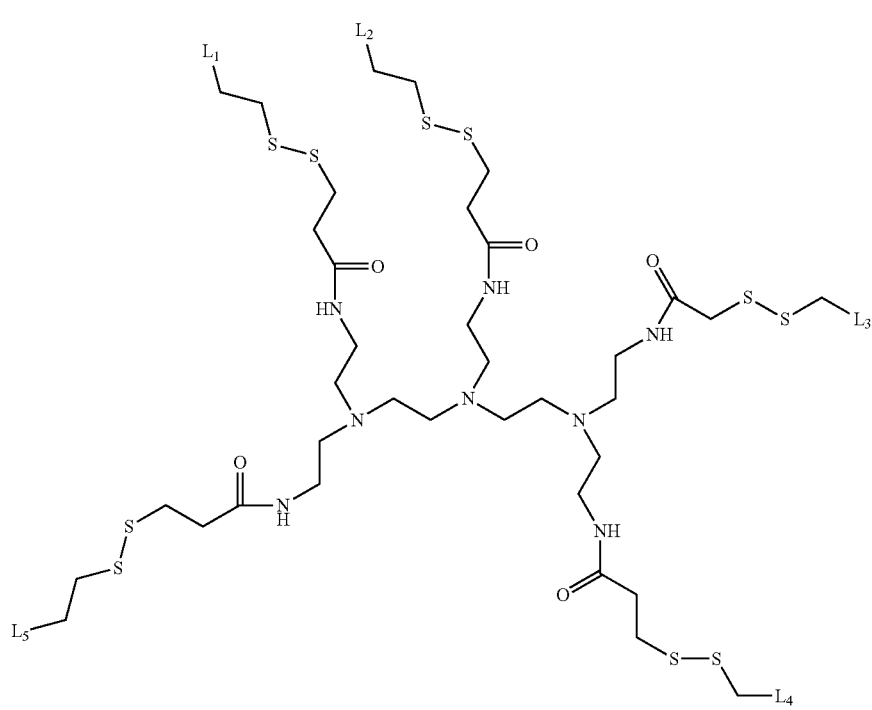

(I)

wherein $L_1$ is the first dendritic polyol, $L_2$ is a second dendritic polyol, $L_3$ is a third dendritic polyol, $L_4$ is a fourth dendritic polyol, and $L_5$ is a fifth dendritic polyol, or b) the structure of Formula (II):

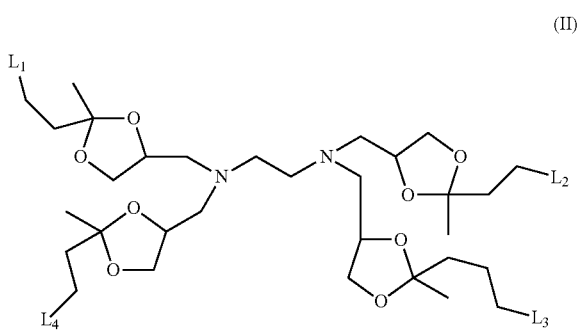

(II)

wherein $L_1$ is the first dendritic polyol and $L_2$ is a second dendritic polyol, and wherein $L_3$ is a third dendritic polyol, and $L_4$ is a fourth dendritic polyol, and wherein the heparin binding polymer binds to heparin and thereby counteracts heparin in the subject.

2. The method of claim 1, wherein the heparin binding polymer further comprises polyethylene glycol covalently attached to the heparin binding polymer.

3. The method of claim 2, wherein the cationic moiety is an amine group.

4. The method of claim 3, wherein the amine group is a tetra-amine group, a hexa-amine group, or a deca-amine group.

5. The method of claim 2, further comprising identifying a subject who has received an excess amount of heparin, wherein the identifying occurs before the heparin binding polymer is administered to the subject.

6. The method of claim 2, wherein an excess amount of heparin was administered to the subject.

7. The method of claim 6, wherein the excess amount of heparin was administered for the maintenance of an intravenous catheter.

8. The method of claim 6, wherein the excess amount of heparin was administered to treat one or more of the following: acute coronary syndrome, atrial fibrillation, cardiac bypass, extracorporeal membrane oxygenation, pancreatitis, hemofiltration, or burns.

9. The method of claim 1, further comprising identifying a subject that would benefit from reducing a level of exogenous heparin that is present in the subject's blood.

10. The method of claim 9, wherein the subject will benefit from an accelerated removal of exogenous heparin from the subject.

11. The method of claim 2, wherein the method is performed in vivo.

12. The method of claim 2, wherein the method is performed ex vivo.

13. The method of claim 1, wherein the subject is a human.

14. The method of claim 1, wherein the subject is a dog, a cat, a horse, a cow, a pig, a mouse, a rat, a rabbit, a monkey, or a guinea pig.

15. The method of claim 1, wherein the heparin binding polymer is administered subcutaneously.

16. The method of claim 1, wherein the heparin binding polymer is administered intravenously.

17. The method of claim 1, wherein the heparin binding polymer binds to heparin selected from at least one of: unfractionated heparin (UFH), low molecular weight heparin (LMWH), ultra low molecular weight heparin (ULMWH), fondaparinux, idraparinux enoxaparin, dalteparin, tinzaparin, semuloparin, or heparinoid.

18. The method of claim 17, wherein the heparin binding polymer binds to fondaparinux.

19. The method of claim 6, wherein the excess amount of heparin is selected from selected from at least one of: unfractionated heparin (UFH), low molecular weight heparin (LMWH), ultra low molecular weight heparin (ULMWH), fondaparinux, idraparinux enoxaparin, dalteparin, tinzaparin, semuloparin, or heparinoid.

20. The method of claim 19, wherein the excess amount of heparin is fondaparinux.

* * * * *

UNITED STATES PATENT AND TRADEMARK OFFICE
CERTIFICATE OF CORRECTION

| | | |
|---|---|---|
| PATENT NO. | : 8,637,008 B2 | Page 1 of 4 |
| APPLICATION NO. | : 13/458899 | |
| DATED | : January 28, 2014 | |
| INVENTOR(S) | : Kizhakkedathu et al. | |

It is certified that error appears in the above-identified patent and that said Letters Patent is hereby corrected as shown below:

On the Title Page, in Item (56), under "OTHER PUBLICATIONS", in Column 1, Line 1, delete "aPTT" and insert -- APTT --, therefor.

On the Title Page, in Item (56), under "OTHER PUBLICATIONS", in Column 2, Line 11, delete "et al," and insert -- et al., --, therefor.

On the Title Page, in Item (56), under "OTHER PUBLICATIONS", in Column 2, Line 21, delete "et al" and insert -- et al., --, therefor.

On the Title Page, in Item (56), under "OTHER PUBLICATIONS", in Column 2, Line 31, delete "et al" and insert -- et al., --, therefor.

On the Title Page, in Item (56), under "OTHER PUBLICATIONS", in Column 2, Line 36, delete "Dendridic" and insert -- Dendritic --, therefor.

On Title Page 2, in Item (56), under "OTHER PUBLICATIONS", in Column 1, Line 31, delete "coplymers," and insert -- copolymers, --, therefor.

On Title Page 2, in Item (56), under "OTHER PUBLICATIONS", in Column 2, Line 17, delete ""Hydrophovically" and insert -- "Hydrophobically --, therefor.

On Title Page 2, in Item (56), under "OTHER PUBLICATIONS", in Column 2, Line 26, delete ""Dendrtic" and insert -- "Dendritic --, therefor.

On Title Page 2, in Item (56), under "OTHER PUBLICATIONS", in Column 2, Line 28, delete "Hyerbranched" and insert -- Hyperbranched --, therefor.

Signed and Sealed this
Twentieth Day of May, 2014

Michelle K. Lee
*Deputy Director of the United States Patent and Trademark Office*

CERTIFICATE OF CORRECTION (continued)

In the Drawings

In Fig. 3, Sheet 9 of 50, delete "BARIER" and insert -- BARRIER --, therefor.

In Fig. 4A, Sheet 10 of 50, delete "LMWH (2.0 U/ml" and insert -- LMWH (2.0 U/ml) --, therefor.

In Fig. 7A, Sheet 13 of 50, delete "R vaues" and insert -- R values --, therefor.

In Fig. 7A, Sheet 13 of 50, delete "Heaprin control" and insert -- Heparin control --, therefor.

In Fig. 7B, Sheet 13 of 50, delete "Heaprin control" and insert -- Heparin control --, therefor.

In Fig. 10B, Sheet 17 of 50, delete "  " and insert -- 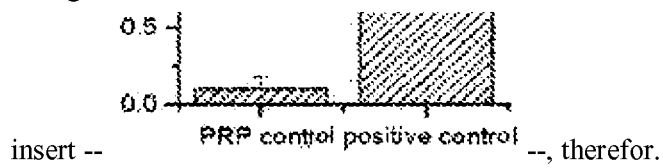 --, therefor.

In Fig. 24A, Sheet 38 of 50, delete "Protaime" and insert -- Protamine --, therefor.

In Fig. 24B, Sheet 39 of 50, delete "Protaime" and insert -- Protamine --, therefor.

In Fig. 24C, Sheet 40 of 50, delete "Protaime" and insert -- Protamine --, therefor.

Figure 30B:
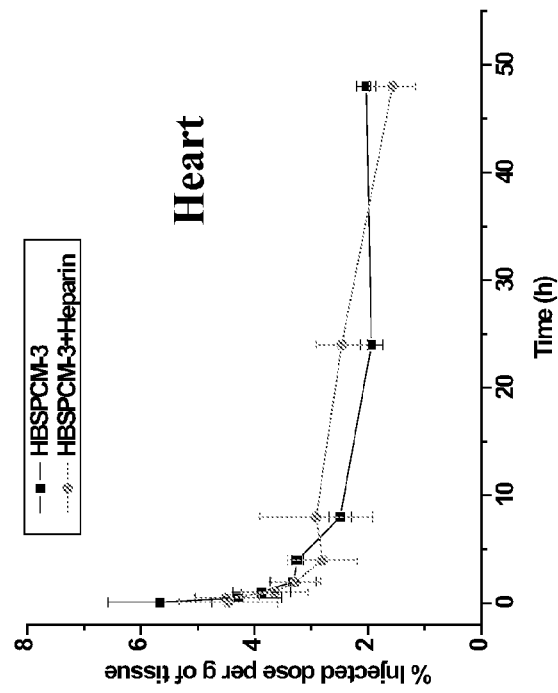
FIG. 30A, FIG. 30B, FIG. 30C, and FIG. 30D are graphs depicting the bio-distribution and pharmacokinetics of HBSPCM-3 in BALB/c mice.
Figure 30A:
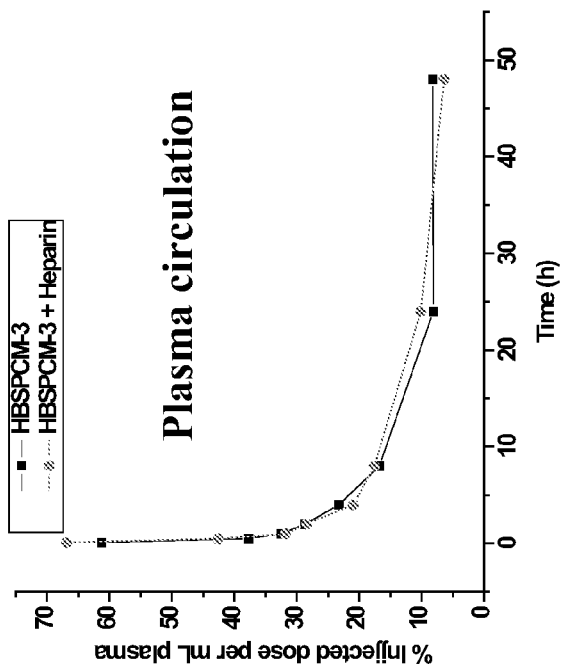
Figure 30D:
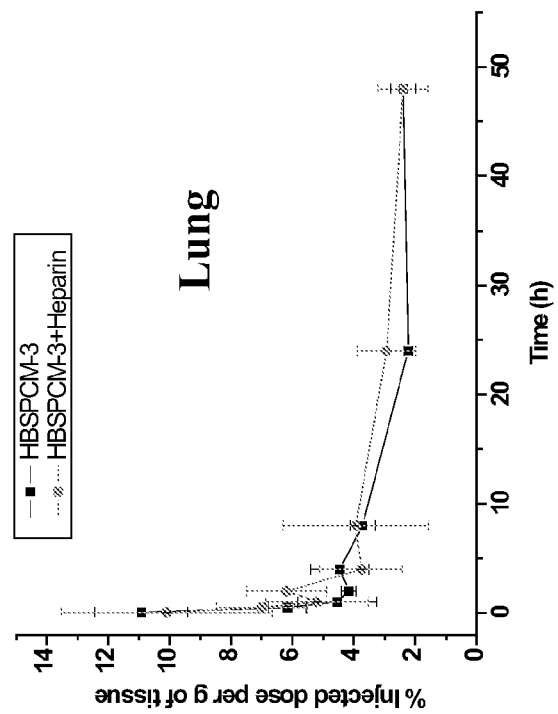
Figure 30C:
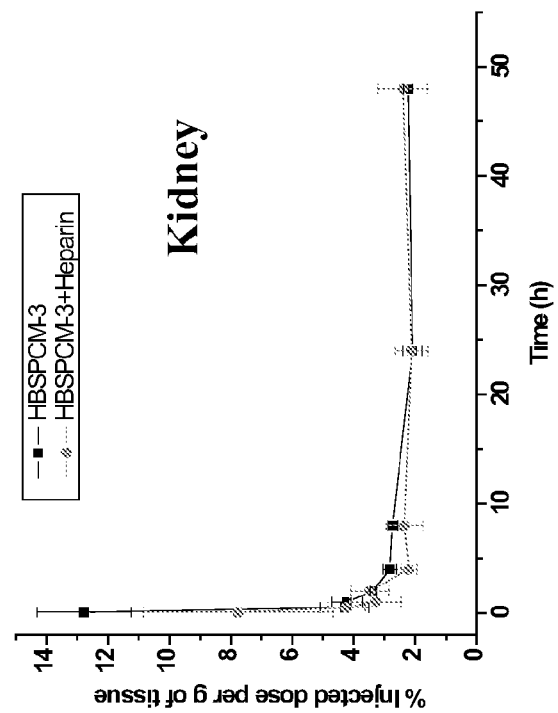
Figure 31B:
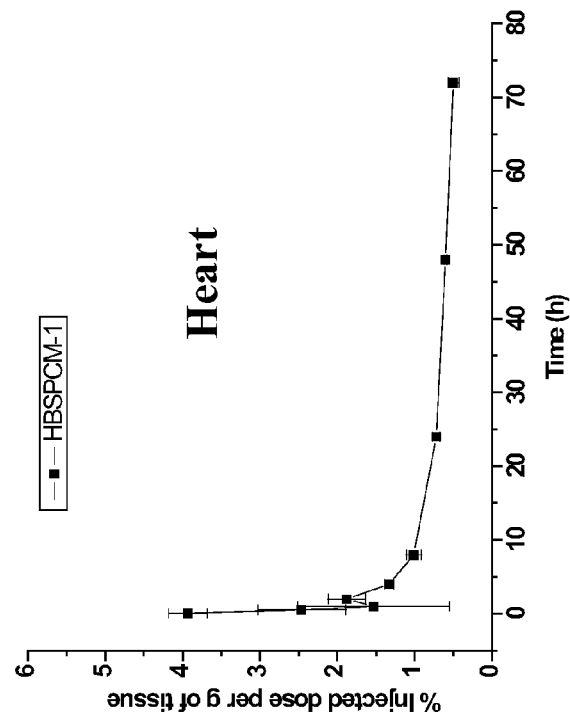
FIG. 31A, FIG. 31B, FIG. 31C, and FIG. 31D are graphs depicting the bio-distribution and pharmacokinetics of HBSPCM-1 in BALB/c mice.
Figure 31A:
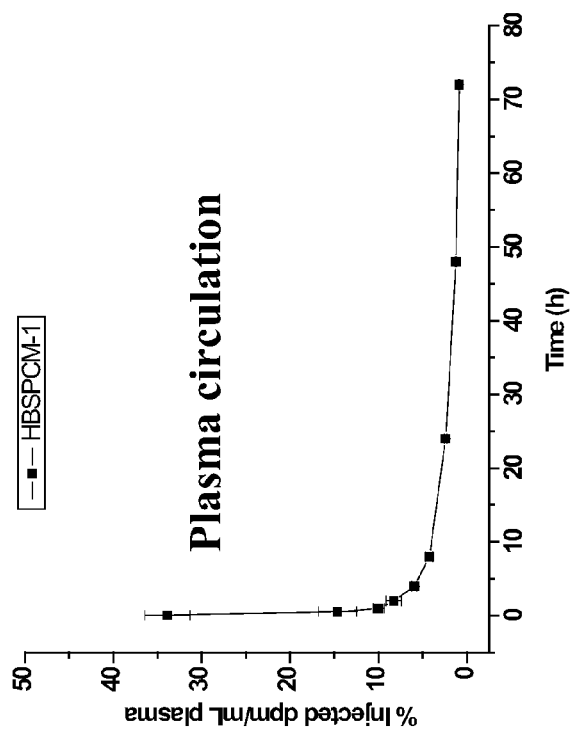
Figure 31D:
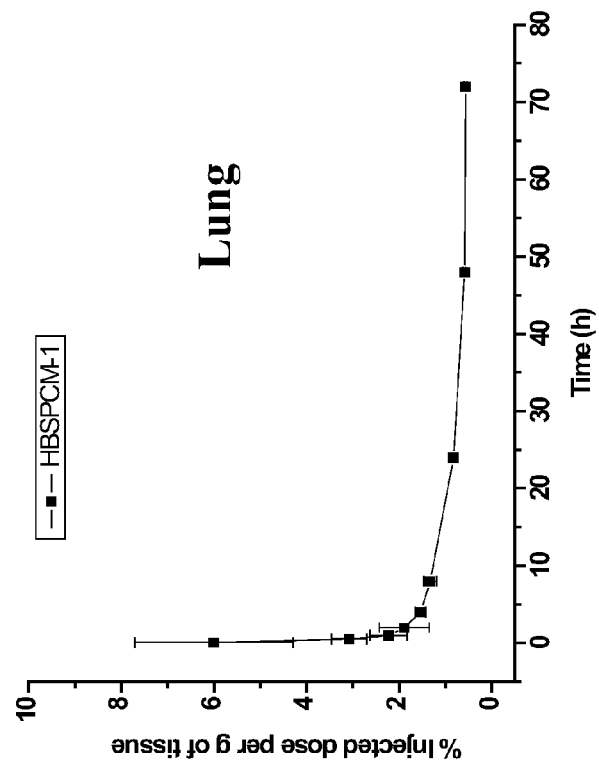
Figure 31C:
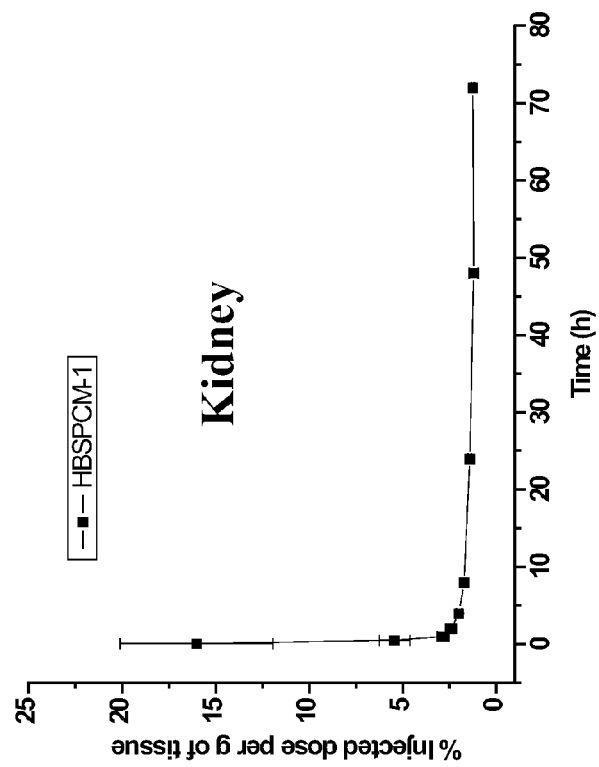

In Fig. 30A, Sheet 46 of 50, delete "% Injjected" and insert -- % Injected --, therefor.

In the Specification

In Column 1, Line 29, delete "pentasccharide" and insert -- pentasaccharide --, therefor.

In Column 1, Lines 29-30, delete "fondaparunix" and insert -- fondaparinux --, therefor.

In Column 2, Line 31, delete "polyglcidol" and insert -- polyglycidol --, therefor.

In Column 2, Line 45, delete "methatrexate" and insert -- methotrexate --, therefor.

In Column 4, Line 22, delete "HBSCPM" and insert -- HBSPCM --, therefor.

In Column 4, Line 29, delete "Exonaparin" and insert -- Enoxaparin --, therefor.

CERTIFICATE OF CORRECTION (continued)
U.S. Pat. No. 8,637,008 B2

In Column 4, Line 48, delete "(JNK-1)" and insert -- (JNK-1). --, therefor.

In Column 6, Line 29, delete "(PEGS)" and insert -- (PEGs) --, therefor.

In Column 8, Line 67, delete "pyrolidone," and insert -- pyrrolidone, --, therefor.

In Column 17, Line 31, delete "methetrexate," and insert -- methotrexate, --, therefor.

In Column 18, Line 51, delete "20 and" and insert -- 20° and --, therefor.

In Column 19, Lines 19-20, delete "polyethelene" and insert -- polyethylene --, therefor.

In Column 19, Line 22, delete "polyethelene" and insert -- polyethylene --, therefor.

In Column 19, Line 24, delete "polyethelene" and insert -- polyethylene --, therefor.

In Column 21, Lines 2-3, delete "Ma activity" and insert -- fXa activity --, therefor.

In Column 22, Line 15, delete "heparing" and insert -- heparin --, therefor.

In Column 22, Line 16, delete "heparing" and insert -- heparin --, therefor.

In Column 29, Line 13, delete "and B." and insert -- and 4B. --, therefor.

In Column 29, Line 39, delete "Tinzparin" and insert -- Tinzaparin --, therefor.

In Column 29, Line 43, delete "Tinzparin" and insert -- Tinzaparin --, therefor.

In Column 31, Line 63, delete "anti-CD 62P-FITC" and insert -- anti-CD62P-FITC --, therefor.

In Column 33, Line 51, delete "HBSCPM" and insert -- HBSPCM --, therefor.

In Column 34, Line 35, delete "LWMH and fondaprinux" and insert -- LMWH and fondaparinux --, therefor.

In Column 34, Line 54, delete "Enoxoparin" and insert -- Enoxaparin --, therefor.

In Columns 33 & 34, in Table 5, delete

"
| SUMMARY OF JNK-2 TITRATIONS | | | | | |
|---|---|---|---|---|---|
| Macromolecule | $N^1$ | $K_a (M^{-1})$ | ΔG (kcal/mol) | ΔH (kcal/mol) | TΔS (kcal/mol) |
| Unfractionated heparin | 0.9 (±0.1) | 1A (±0.7) × 106 | −8.3 (±0.2) | −94 (±15) | −85 (±15) |
| LMWH (Enoxoparin) | 2.95 (±0.08) | 1.3 (±0.2) × 105 | 7.0 (±0.1) | 34.8 (±0.5) | 27.8 (±0A) |
| Fondaparinux | 2.3 (±0.01) | 1.5 (±0.2) × 105 | −7.1 (±0.1) | −17.9 (±0.2) | −10.9 (±0.1) |

"

and insert

| SUMMARY OF JNK-2 TITRATIONS | | | | | |
|---|---|---|---|---|---|
| Macromolecule | $N^1$ | $K_a (M^{-1})$ | $\Delta G$ (kcal/mol) | $\Delta H$ (kcal/mol) | $T\Delta S$ (kcal/mol) |
| Unfractionated heparin | 0.9 (±0.1) | 1.4 (±0.7) × 106 | −8.3 (±0.2) | −94 (±15) | −85 (±15) |
| LMWH (Enoxaparin) | 2.95 (±0.08) | 1.3 (±0.2) × 105 | −7.0 (±0.1) | −34.8 (±0.5) | 27.8 (±0.4) |
| Fondaparinux | 2.3 (±0.01) | 1.5 (±0.2) × 105 | −7.1 (±0.1) | −17.9 (±0.2) | −10.9 (±0.1) | therefor.

In Column 35, Line 18, delete "Exonaparin)" and insert -- Enoxaparin) --, therefor.

In Column 39, Line 56, delete "250 μA" and insert -- 25 μL --, therefor.

In Column 42, Line 7, delete "solution" and insert -- solution. --, therefor.